(12) United States Patent
Kelleher et al.

(10) Patent No.: US 10,808,256 B2
(45) Date of Patent: Oct. 20, 2020

(54) SYSTEMS AND METHODS FOR UNTARGETED METABOLOMIC SCREENING

(71) Applicant: Northwestern University, Evanston, IL (US)

(72) Inventors: Neil L. Kelleher, Evanston, IL (US); Paul M. Thomas, Morton Grove, IL (US); Kenneth D. Clevenger, Chicago, IL (US); Matthew Thomas Robey, Chicago, IL (US)

(73) Assignee: Northwestern University, Evanston, IL (US)

( * ) Notice: Subject to any disclaimer, the term of this patent is extended or adjusted under 35 U.S.C. 154(b) by 0 days.

(21) Appl. No.: 15/602,917

(22) Filed: May 23, 2017

(65) Prior Publication Data

US 2017/0335335 A1 Nov. 23, 2017

Related U.S. Application Data

(60) Provisional application No. 62/340,116, filed on May 23, 2016.

(51) Int. Cl.
| | |
|---|---|
| *C12N 15/52* | (2006.01) |
| *C12N 15/80* | (2006.01) |
| *C07K 14/195* | (2006.01) |
| *C12N 15/09* | (2006.01) |
| *C12N 15/00* | (2006.01) |

(52) U.S. Cl.
CPC ............ *C12N 15/80* (2013.01); *C07K 14/195* (2013.01); *C12N 15/09* (2013.01); *C12N 15/52* (2013.01); *C12N 15/00* (2013.01)

(58) Field of Classification Search
CPC .................................. C12N 15/52; C12N 15/80
See application file for complete search history.

(56) References Cited

U.S. PATENT DOCUMENTS

| | | |
|---|---|---|
| 2003/0180766 A1 | 9/2003 | Farnet et al. |
| 2014/0011203 A1 | 1/2014 | Kobayashi et al. |
| 2015/0037862 A1 | 2/2015 | Keller |

FOREIGN PATENT DOCUMENTS

| | | |
|---|---|---|
| WO | WO 2014144583 A2 | 9/2014 |
| WO | WO 2016005049 A1 | 1/2016 |

OTHER PUBLICATIONS

Clevenger et al. Jan. 1, 2016; Reviving natural product and drug discovery pipelines with fungal artificial chromosome (FAC) technology. 10th Annual TechConnect World Innovation Conference and Expo, Held Jointly with the 19th Annual Nanotech Conference and Expo, and the 2016 National SBIR/STTR., pags. 1-2.*
Alberts et al., Mevinolin: a highly potent competitive inhibitor of hydroxymethylglutaryl-coenzyme A reductase and a cholesterol-lowering agent, PNAS, 1980;77(7):3957-3961.
Borel et al., Ciclosporin and its future. Prog Allergy. 1986;38:9-18.
Bok et al., Fungal artificial chromosomes for mining of the fungal secondary metabolome, BMC Genomics, 2015;16(343):1-10.
Brakhage, Molecular Regulation of β-Lactam Biosynthesis in Filamentous Fungi, Microbiol Mol Biol Rev, 1998;62(3):547-585.
Clevenger et al., A scalable platform to identify fungal secondary metabolites and their gene clusters. Nat Chem Biol. Aug. 2017;13(8):895-901.
Jensen et al., Beta-lactams. Biotechnology. 1995;28:239-68.
Luengo et al., Penicillin biosynthesis. Prog Ind Microbiol. 1994;29:603-38.
Nielsen et al., Heterologous Reconstitution of the Intact Geodin Gene Cluster in Aspergillus nidulans through a Simple and Versatile PCR Based Approach, PLoS One, 2013;8(8):e72871.
Wilm et al., Analytical Properties of the Nanoelectrospray Ion Source, Anal Chem, 1996;68(1):1-8.
International Search Report of related PCT/US2017/34023, dated Aug. 25, 2017, 11 pages.

* cited by examiner

*Primary Examiner* — Karen Cochrane Carlson
(74) *Attorney, Agent, or Firm* — Casimir Jones SC; David W. Staple

(57) ABSTRACT

Provided herein are systems and methods for untargeted screening of metabolite products of biosynthetic gene clusters. In particular, systems and methods are provided for the detection of secondary metabolites and the correlation off such metabolites to the biosynthetic gene clusters responsible for the biosynthesis thereof.

17 Claims, 37 Drawing Sheets

Specification includes a Sequence Listing.

Fungal compounds matching:
$C_{25}H_{36}O_2$, 368.2715 Da

Variecolin

Ophiobolin V

Ophiobolin U 21-hydroxy-Ophiobolin G

6-Epiophiobolin N

Ophiobolin in unknown compound molecular family: $C_{25}H_{38}O_3$, 386.2821 Da

Ophiobolin H

SEQUENCE LISTING

<160> NUMBER OF SEQ ID NOS: 8

<210> SEQ ID NO 1
<211> LENGTH: 3
<212> TYPE: DNA
<213> ORGANISM: Aspergillus terreus

<400> SEQUENCE: 1 atc                                                                         3

<210> SEQ ID NO 2
<211> LENGTH: 6
<212> TYPE: DNA
<213> ORGANISM: Aspergillus terreus

<400> SEQUENCE: 2 atcatc                                                                      6

<210> SEQ ID NO 3
<211> LENGTH: 7
<212> TYPE: DNA
<213> ORGANISM: Aspergillus terreus

<400> SEQUENCE: 3 catcatc                                                                     7

<210> SEQ ID NO 4
<211> LENGTH: 10
<212> TYPE: PRT
<213> ORGANISM: Aspergillus terreus

<400> SEQUENCE: 4

Gly Met Phe Ile Val Gly Leu Gly Met Lys
1               5                   10

<210> SEQ ID NO 5
<211> LENGTH: 10
<212> TYPE: PRT
<213> ORGANISM: Aspergillus terreus

<400> SEQUENCE: 5

Gly Ile Asn Phe Ile Gly Ala Gly Thr Lys
1               5                   10

<210> SEQ ID NO 6
<211> LENGTH: 10
<212> TYPE: PRT
<213> ORGANISM: Aspergillus terreus

<400> SEQUENCE: 6

Asp Met Asn Val Met Gly Gly Val Thr Lys
1               5                   10

```
<210> SEQ ID NO 7
<211> LENGTH: 10
<212> TYPE: PRT
<213> ORGANISM: Aspergillus terreus

<400> SEQUENCE: 7

Asp Ala Leu Leu Leu Gly Ile Thr Ile Lys
1               5                   10

<210> SEQ ID NO 8
<211> LENGTH: 10
<212> TYPE: PRT
<213> ORGANISM: Aspergillus terreus

<400> SEQUENCE: 8

Asp Leu Gly Phe Ser Gly Pro Ile Ile Lys
1               5                   10
```

SYSTEMS AND METHODS FOR UNTARGETED METABOLOMIC SCREENING

CROSS-REFERENCE TO RELATED APPLICATIONS

The present invention claims priority benefit of U.S. Provisional Patent Application 62/340,116, filed May 23, 2016, which is incorporated by reference in its entirety.

STATEMENT REGARDING FEDERAL FUNDING

This invention was made with government support under R44 AI094885 (Subcontract Intact Genomics No. Jul. 25, 2014/2R44AI094885-02 Intact Genomics) awarded by the National Institutes of Health. The government has certain rights in the invention.

FIELD

Provided herein are systems and methods for untargeted screening of metabolite products of biosynthetic gene clusters. In particular, systems and methods are provided for the detection of secondary metabolites (SMs) and the correlation of such metabolites to the biosynthetic gene clusters responsible for the biosynthesis thereof.

BACKGROUND

Secondary metabolite production by various fungi has been an extremely important source of a variety of therapeutically significant pharmaceuticals. Beta-lactam antibacterials such as penicillin and cephalosporin are produced by *Penicillium chrysogenum* and *Acremonium chrysogenum*, respectively, and these compounds are by far the most frequently used antibacterials (reviewed in Luengo and Penalva, Prog. Ind. Microbiol. 29: 603-38 (1994); Jensen and Demain, Biotechnology 28: 239-68 (1995); Brakhage, Microbiol. Mol. Biol. Rev. 62: 547-85 (1998); incorporated by reference in their entireties). Cyclosporin A, a member of a class of cyclic undecapeptides, is produced by *Tolypocladium inflatum*. Cyclosporin A dramatically reduces morbidity and increases survival rates in transplant patients (Borel, Prog. Allergy 38: 9-18 (1986); incorporated by reference in its entirety). In addition, several fungal secondary metabolites are cholesterol lowering drugs, including lovastatin that is made by *Aspergillus terreus* and several other fungi (Alberts et al., Proc. Natl. Acad. Sci. USA 77: 3957-3961 (1980); incorporated by reference in its entirety).

Filamentous fungal genomes contain 20-40 megabases of DNA and encode a vast array of secondary metabolites. It is estimated that over 100,000 filamentous fungal species (molds) exist on earth, each containing on the order of 50 BGCs. However, translating the vast biosynthetic potential of fungal genomes into defined and renewable chemical libraries has proven challenging largely due to cryptic expression and recalcitrant genetics of some species, with most progress being made in only a handful of fungal species.

What is needed is techniques for the untargeted analysis of metabolites and BGCs in order to identify new metabolites along with correlation to the BGCs responsible for their synthesis.

SUMMARY

Provided herein are systems and methods for untargeted screening of metabolite products of biosynthetic gene clusters. In particular, systems and methods are provided for the detection of secondary metabolites (SMs) and the correlation of such metabolites to the biosynthetic gene clusters responsible for the biosynthesis thereof.

In some embodiments, provided herein are methods comprising: (a) expressing a putative biosynthetic gene cluster (pBGC) in a host system; (b) screening metabolites produced by the host system by one or more bioanalytical techniques; and (c) scoring metabolites based on a combination of uniqueness and abundance.

In some embodiments, provided herein are methods comprising: (a) screening a sample a sample produced by expressing a putative biosynthetic gene cluster (pBGC) in a host system for metabolites, wherein the sample is screened by one or more bioanalytical techniques; and (b) scoring metabolites detected by the screen based on a combination of uniqueness and abundance.

In some embodiments, methods further comprise identifying the pBGC as a biosynthetic gene cluster (BGC) if the scoring identifies a particular metabolite as being highly unique and abundant relative to other scored metabolites. In some embodiments, methods further comprise identifying a particular metabolite as being produced by the pBGC if the scoring identifies the particular metabolite as being highly unique and abundant relative to other scored metabolites. In some embodiments, methods further comprise identifying (i) the pBGC as a biosynthetic gene cluster (BGC), and (ii) the particular metabolite as being produced by the pBGC, if the scoring identifies a particular metabolite as being highly unique and abundant relative to other scored metabolites.

In some embodiments, methods further comprise validating the identified BGC and/or metabolite repeating the screen with the pBGC comprising a deletion. In some embodiments, one or more genes are deleted (e.g., completely or substantially) from the pBGC. In some embodiments, the validation confirms that the pBGC is a BGC that produces the metabolite because the deletion reduces or eliminates production of the particular metabolite by the host system. In some embodiments, the validation is performed for multiple deletions within the pBGC (e.g., within multiple different genes within the pBGC). In some embodiments, the validation identifies the function within the metabolites biosynthetic pathway or the delected gene(s). In some embodiments the comparison of the metabolite from the pBGC with and without deletion specifically allows the function of the deleted DNA to be identified.

In some embodiments, the pBGC comprises a sequence derived from genomic DNA of a fungus of interest. In some embodiments, the pBGC comprises a sequence of modified or engineered genomic DNA of a fungus of interest. In some embodiments, the pBGC comprises a sequence derived from genomic DNA of a plant of bacteria of interest. In some embodiments, the pBGC has been inserted into a fungal artificial chromosome (FAC). In some embodiments the pBGC has been inserted into a bacterial artificial chromosome (BAC). In some embodiments the pBGC is inserted into a yeast artificial chromosome (YAC). In some embodiments the pBGC is an artificial chromosome. In some embodiments the pBGC is inserted into an expression plasmid. In some embodiments the pBGC is inserted into an expression vector. In some embodiments the pBGC is a FAC. In some embodiments the pBGC is a BAC. In some embodiments the pBGC is a YAC. In some embodiments the pBGC is an artificial chromosome. In some embodiments the pBGC is an expression plasmid. In some embodiments the pBGC is an expression vector.

In some embodiments, the host system is a fungal cell. In some embodiments, the fungal cell is selected from the group consisting of *Ashbya gossypii, Aspergillus nidulans, Coprinus cinereus, Cryptococcus neoformans, Neurospora crassa, Saccharomyces cerevisiae, Schizophyllum commune, Schizosaccharomyces pombe*, and *Ustilago maydis*. In some embodiments, the host system is a fungal lysate. In some embodiments, the host system is an in vitro expression system. In some embodiments the host system is a bacterial cell. In some embodiments the host system is a plant cell. In some embodiments the host system is an animal cell. In some embodiments, screening comprises subjecting the host system or test sample derived therefrom to the one or more bioanalytical techniques to identify bioanalytical features that correlate to metabolites produced by the host system expressing the pBGC. In some embodiments, scoring comprises calculating a numerical score or otherwise ranking the features obtained in the screening based on a combination of uniqueness and abundance. In some embodiments, abundance is a measure of the size of a feature and/or amount of a metabolite, relative to other features and/or metabolites produced by the host system expressing the pBGC. In some embodiments, uniqueness is a measure of the relative rarity of a feature and/or metabolite, relative to other features and/or metabolites produced by similar host systems expressing other BGCs or pBGCs. In some embodiments, the one or more bioanalytical techniques are selected from the group consisting of mass spectrometry (MS), tandem mass spectrometry (MS2), high performance liquid chromatography (HPLC), gas chromatography, ultra-performance liquid chromatography (UPLC), supercritical fluid chromatography, nuclear magnetic resonance (NMR), liquid chromatography-mass spectrometry (LC-MS), gas chromatography-mass spectrometry (GC-MS), liquid chromatography-diode array detection (LC-DAD), capillary electrophoresis-mass spectrometry (CE-MS), and liquid chromatography-tandem mass spectrometry (LC-MS2). In some embodiments, methods further comprise isolating the particular metabolite. In some embodiments, provided herein are compositions isolated by the methods herein. In some embodiments, methods further comprise identifying the particular metabolite. In some embodiments, provided herein are compositions identified by the methods herein.

DEFINITIONS

Figure 1:
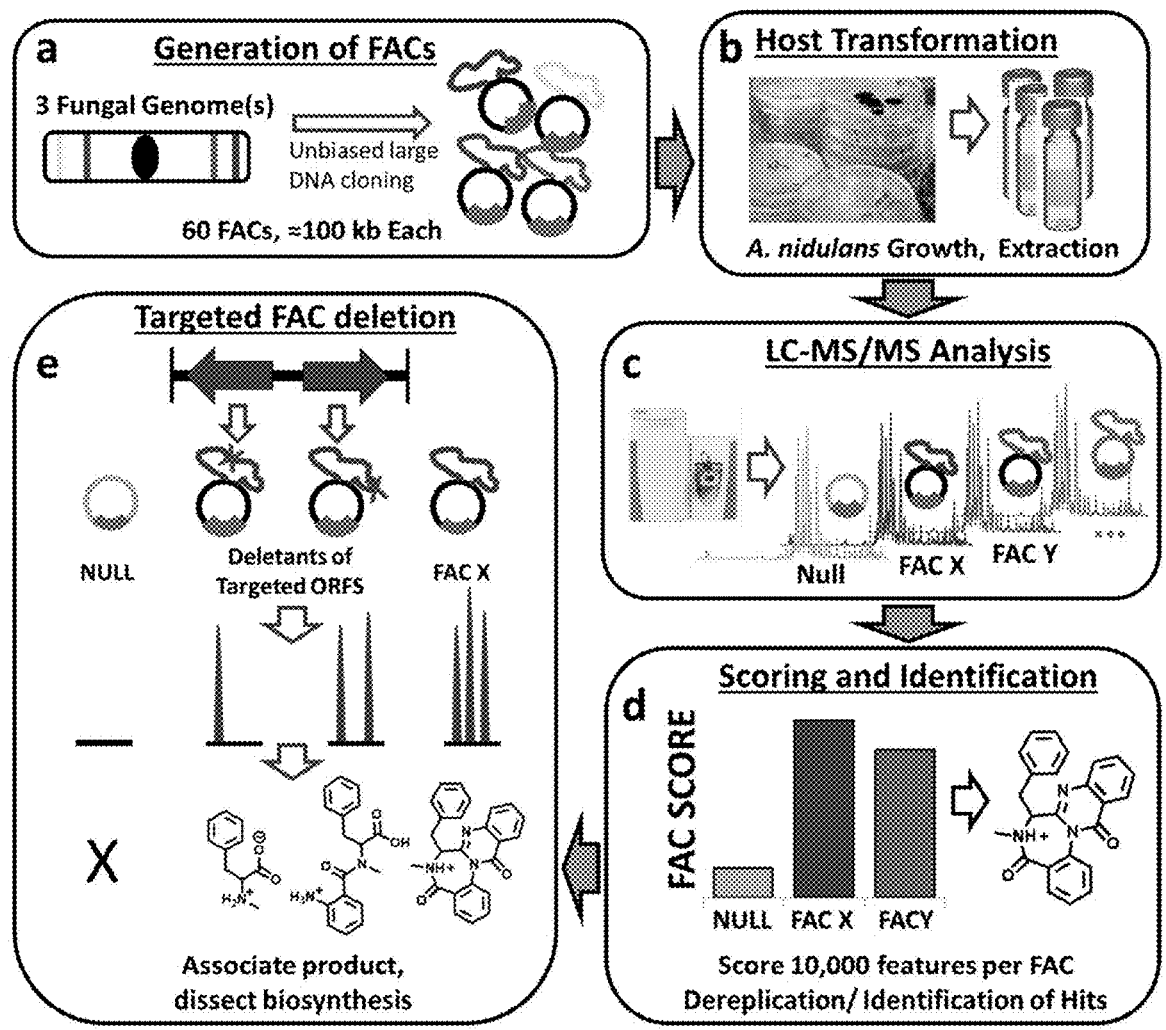
FIG. 1. (Panel A) Generation of FACs from randomly sheared genomic DNA and cloning into self-replicating *E. coli*-fungal shuttle vectors. (Panel B) Transformation into expression host, *A. nidulans*, and extraction of SMs. (Panel C) Untargeted high resolution LC-MS/MS analysis of SM extracts from each FAC. (Panel D) Feature detection, scoring, and hit identification/de-replication. (Panel E) Generation of FAC deletants, association of SMs with FAC ORFs, dissection of biosynthetic pathway.

As used herein the term "biosynthetic gene cluster" ("BGC") refers to a set of several genes that direct the synthesis of a particular metabolite (e.g., a secondary metabolite). The genes are typically located on the same stretch of a genome, often within a few thousand bases of each other. Genes of a BGC may encode proteins which are similar or unrelated in structure and/or function. The encoded proteins are typically either (i) enzymes involved in the biosynthesis of metabolites or metabolite precursors and/or (ii) are involved inter alia in regulation or transport of metabolites or metabolite precursors. Together, the genes of the BGC encode proteins that serve the purpose of the biosynthesis of the metabolite. The term "putative biosynthetic gene cluster" ("pBGC") refers to a segment of a genome that is suspected of being a BGC or is to be tested for being a BGC. A pBGC may be identified by computational genomic analysis, functional analysis of the genes in a stretch of a genome, other techniques, or combinations thereof.

As used herein, the term "primary metabolite" refers to a molecule that is directly involved in normal growth, development, and reproduction of an organism, and is present across the spectrum of cell and organism types. Common examples of primary metabolites include, but are not limited to ethanol, lactic acid, and certain amino acids.

As used herein, the term "secondary metabolite" refers to a molecule that is typically not directly involved in processes central to growth, development, and reproduction of an organism, and is present in a taxonomically restricted set of organisms or cells (e.g., plants, fungi, bacteria, or specific species or genera thereof). Examples of secondary metabolites include ergot alkaloids, antibiotics, naphthalenes, nucleosides, phenazines, quinolines, terpenoids, peptides, and growth factors.

As used herein, the term "fungal artificial chromosome" ("FAC") refers to a nucleic acid construct containing structural elements of a fungal chromosome (e.g., telomeric, centromeric, and/or origin of replication sequences) that can be genetically modified to contain a heterologous DNA sequence.

As used herein, the terms "FAC at20", "at20", and "AtFAC9J20" refer to the same fungal artificial chromosome construct.

As used herein, the term "small molecule" refers to organic or inorganic molecular species either synthesized or found in nature, generally having a molecular weight less than 10,000 grams per mole, optionally less than 5,000 grams per mole, and optionally less than 2,000 grams per mole.

DETAILED DESCRIPTION

Provided herein are systems and methods for untargeted screening of metabolite products of biosynthetic gene clusters. In particular, systems and methods are provided for the detection of secondary metabolites and the correlation off such metabolites to the biosynthetic gene clusters responsible for the biosynthesis thereof.

Experiments conducted during development of embodiments herein demonstrate systems and methods in which BGCs (or pBGCs) from multiple different species' genomes (from multiple different fungal genera) were processed into BGC-specific vectors and screened for metabolite production. Metabolites specifically produced by BGC-specific vectors were identified by analysis of the uniqueness and relative abundance of detectable features of the products of the BGC-specific vectors. In particular, fungal genomes were processed into fungal artificial chromosomes (FACs) and were screened for metabolite production using Fourier-transform mass spectrometry (FTMS). A FAC-score based on the uniqueness and relative abundance of FAC-specific features revealed the presence of new putative metabolites in a significant subset of the FACs analyzed. In a particular experiment, the systems and methods described herein rapidly identified one FAC as comprising the benzomalvin BGC nested with two others encoding an ophiobolin-like terpenoid and a new lipopeptide encoded by a PKS-NRPS assembly line.

In some embodiments, analysis of the uniqueness and relative abundance of FAC-specific features (e.g., MS peaks) are used to identify BGCs and the metabolites produced thereby. Relative abundance is a measure of the amount of a particular metabolite (e.g., based on peak size) relative to other metabolites produced by the system expressing the BGC. In some embodiments, if the BCG produces a metabolite, the abundance of that metabolite relative to other metabolites (e.g., average metabolite abundance) produced by the host system will be relatively high (e.g., >0.1, >0.25, >0.5, >0.75, >1.0, >1.25, >1.5, >1.75, >2.0, >2.5, >3.0, >4.0, >5.0, etc.). Uniqueness is a measure of the distinct presence of a particular metabolite produced by a host system expressing a BCG, relative to other control systems (e.g., same system but without BCG expression) or other systems expressing other BCGs. In some embodiments, if a particular BCG produces a metabolite, the amount of that metabolite in the system expressing the particular BCG, relative to the amount of that metabolite in other systems not expressing the particular BCG will be relatively high (e.g., >1, >2, >3, >4, >4, >5, >6, >7, >8, >9, >10, >20, >30, >40, >50, >75, >100, >200, >500, >1000, etc.).

Discovery of fungal metabolites and the BGCs responsible for the biosynthesis thereof has historically been challenging and slow, due at least in part to cryptic expression and recalcitrant genetics of fungal genomes. Recent advances in sequencing technology have spurred development of heterologous expression systems of fungal BGCs, leading to modest increases in rates of discovery of fungal metabolites. Unfortunately, the pace is still woefully inadequate to tackle the 1000s of BGCs uncovered by sequencing efforts. To meet the challenge of large-scale assignment of fungal secondary metabolites with their BGCs, provided herein are systems and methods to interrogate the secondary metabolome of fungal species using, for example mass spectrometry and associated analysis techniques. For example, in experiments conducted during development of embodiments herein the secondary metabolomes of three taxonomically diverse *Aspergillus* species were interrogated using untargeted LC-FTMS analysis of 56 FACs, each of which contained one or more orphan BGCs. These systems and methods provide for the systematic screening of large numbers (e.g., 1000, 2000, 5000, 10,000, or more) of gene clusters with a reliable hit rate. Embodiments herein have improved by at least an order of magnitude the rate at which new BGC/SM pairs are identified and correlated. Additional experiments conducted during development of embodiments herein demonstrate the utility of the systems and methods herein in the identification of metabolites and BCGs from non-*Aspergillus* fungal species, such as *Talaromyces marneffei, Fusarium solani, Pseudogymnoascus destructans*, and *Penicillium expansum*.

In some embodiments, the systems and methods herein find use in the analysis of pBGCs from filamentous fungal genomes. However, the systems and methods herein may also find use in exploring genes, gene clusters, expression products and metabolites produced therefrom, from other eukaryotes, prokaryotes, etc. In particular embodiments, pBGCs for analysis by the methods herein are from a genus selected from *Acremonium, Alternaria, Aspergillus, Cladosporium, Fusarium, Mucor, Penicillium, Rhizopus, Sryichoium, Stachybotrys, Trichoderma*, and *Trichophyton*.

Figure 4A:
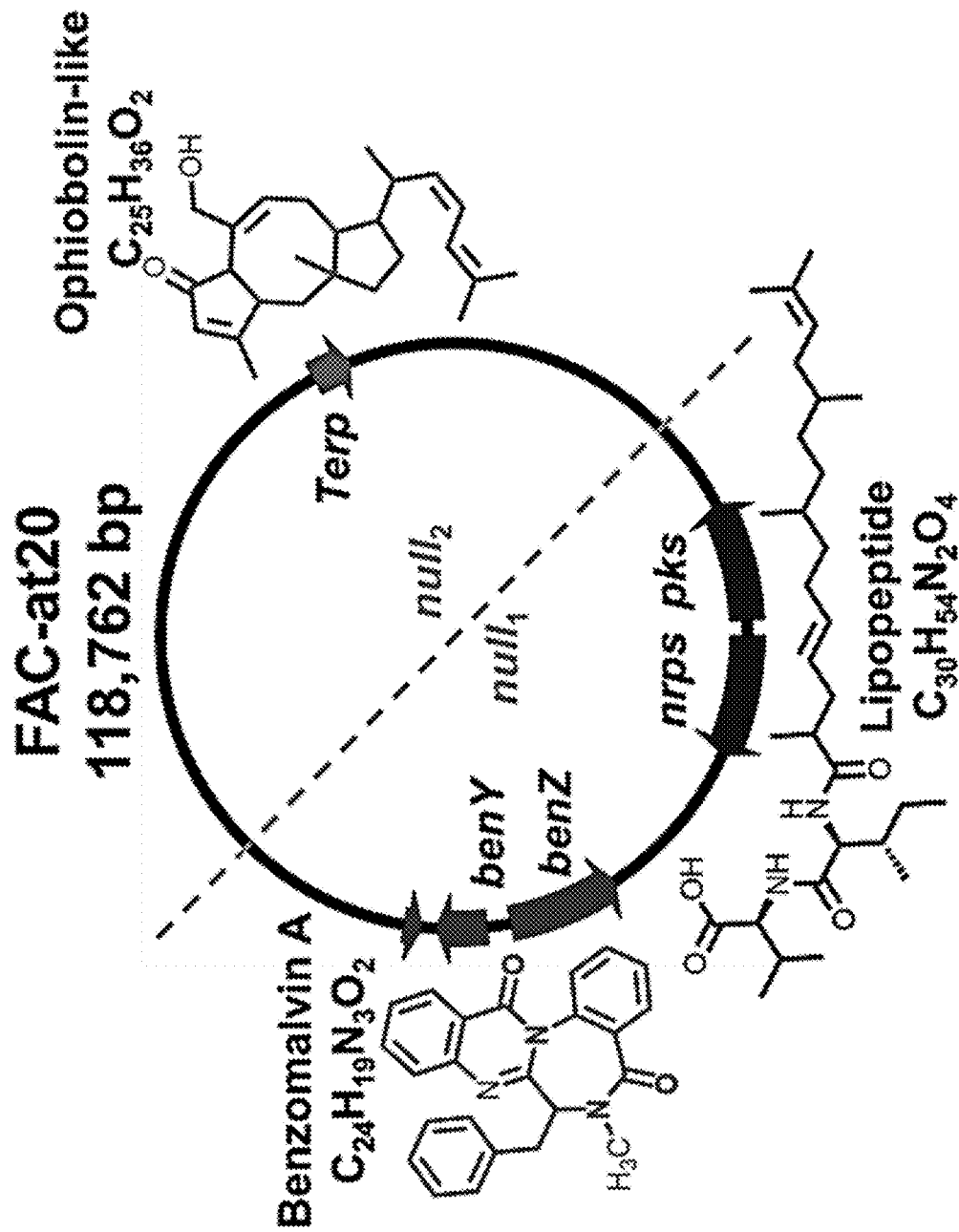
FIGS. 4A-C. FAC-MS reveals three biosynthetic gene clusters and products of AtFAC9J20. (A) Map of AtFAC9J20 construct and biosynthetic products, showing the genes identified as producing secondary metabolites, and the corresponding SMs. The PKS shares homology with the diketide synthase gene lovF. Hypothetical structure is shown based on MS2 and bioinformatic analysis. (B) Effect of backbone gene deletants on the biosynthetic products of AtFAC9J20. (C) 56 BGCs were screened from 3 species and 17 BGC products were detected, a 30% hit rate. The table estimates the number of assigned SM-BGC pairs for screening of increasing library sizes, up to 1,000 corresponding to the scale of the Department of Energy 1,000 fungal genomes project.
Figure 4B:
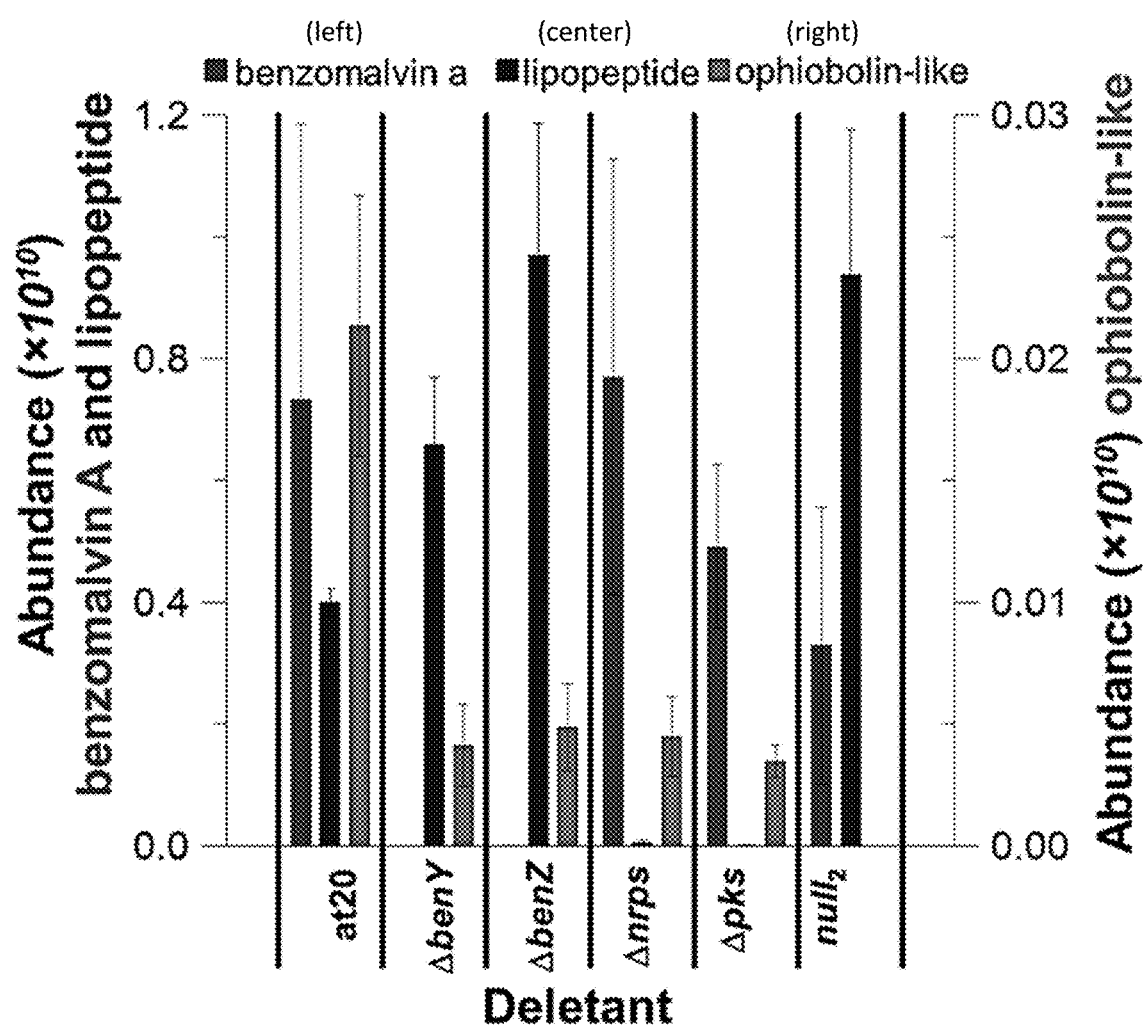
Figure 4C:
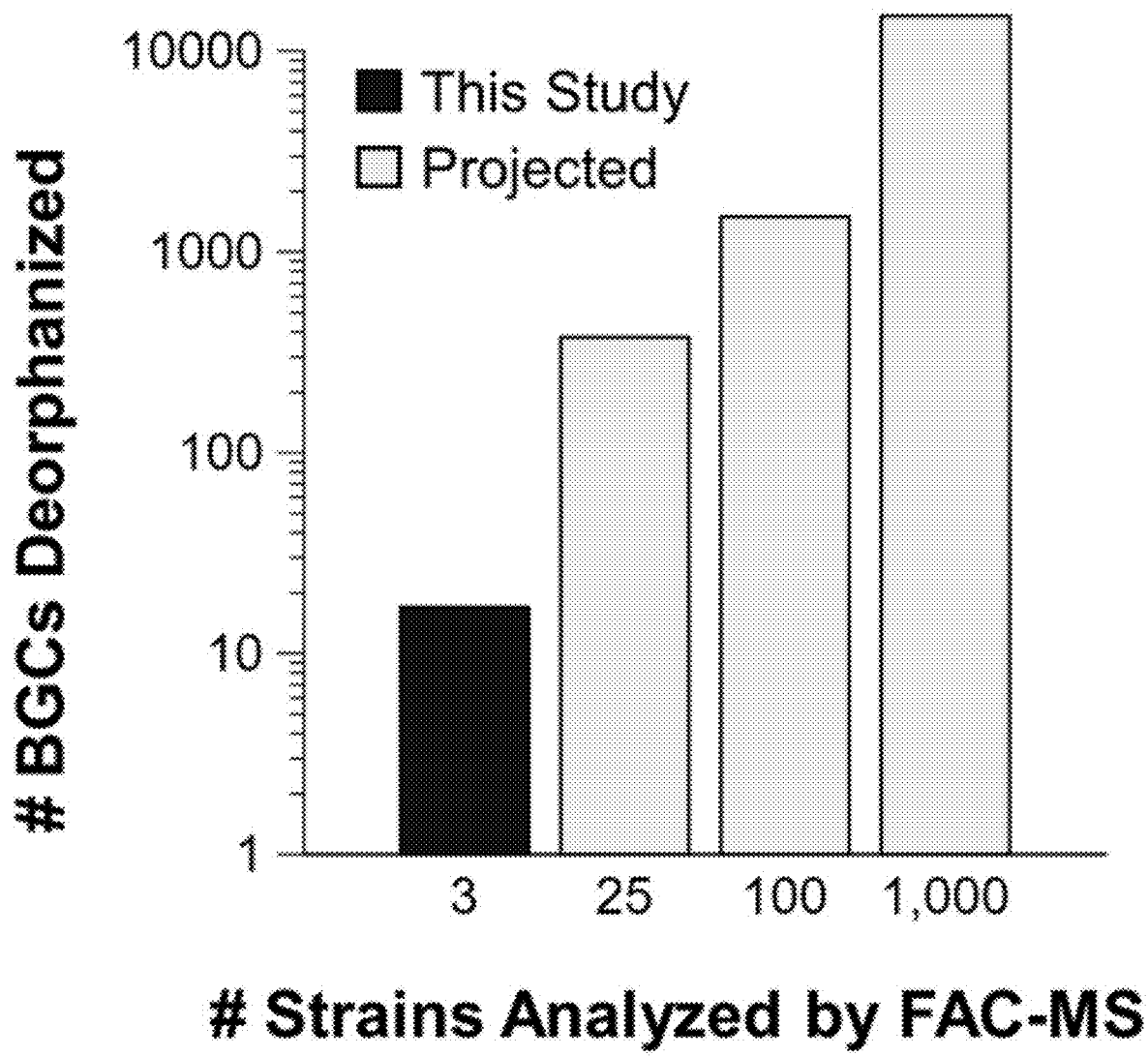

In order to search for heterologous FAC products in an unbiased method, naïve to their chemical formulas, systems and methods were developed for calculating a FAC-score that could be rapidly assigned based on features identified by bioanalytical analysis (e.g., LC-FTMS or MS2) of systems expressing the FAC detected compound. The methods herein provide rapid triage of whether or not a particular FAC likely-produces a heterologous SM (17/56 exemplary FACs tested were identified as producing an SM). Accurate mass de-replication against natural product databases quickly reveals whether the FAC are responsible for the biosynthesis of known or unknown compounds (16/17 exemplary FACs identified as producing SMs were found to produce unknown compounds). Thus, extension of this technology across numerous strain collections would be expected to reveal a large number of unknown metabolites. For instance, estimating an average of 50 BGCs per 100 *Aspergillus* species (the genus contains several 100 species) with a hit rate of 30% (as observed in the experiments conducted during development of embodiments herein) would yield about 1,500 products and correlated BGCs from this genus alone (FIG. 4C).

In some embodiments, systems and methods are provided for the detection and/or identification of an unknown molecular species (e.g., molecular species that were not known to be present in the sample prior to analysis) present in a test sample. In some embodiments, systems and methods provide for the detection/identification of an unknown molecular species that is unique to the test sample, relative to other test samples and/or control samples. In some embodiments, the unknown molecular species is present in greater abundance (e.g., 2-fold, 5, fold, 10-fold, 20-fold, 50-fold, $10^2$-fold, $10^3$-fold, $10^4$-fold, $10^5$-fold, $10^6$-fold, $10^7$-fold, or more) in the test sample relative to other test samples and/or control samples.

In some embodiments, a test sample is analyzed by a bioanalytical (e.g., biophysical and/or biochemical technique), such as a chromatographic and/or mass spectroscopic technique, along with other test and/or control samples. In some embodiments, analysis of the data generated from such bioanalytical (e.g., biophysical/biochemical) analysis identifies the presence of molecular species present in one test sample but absent or in minute concentration (e.g., relative to the one test sample) in other test samples and/or control samples.

In some embodiments, the one or more bioanalytical techniques are selected from the group consisting of mass spectrometry (MS), tandem mass spectrometry (MS2), high performance liquid chromatography (HPLC), gas chromatography, ultra-performance liquid chromatography (UPLC), supercritical fluid chromatography, nuclear magnetic resonance (NMR), liquid chromatography-mass spectrometry (LC-MS), gas chromatography-mass spectrometry (GC-MS), liquid chromatography-diode array detection (LC-DAD), capillary electrophoresis-mass spectrometry (CE-MS), imaging mass spectrometry (IMS), and liquid chromatography-tandem mass spectrometry (LC-MS2). In some embodiments, methods further comprise isolating the particular metabolite. In some embodiments, provided herein are compositions isolated by the methods herein. In some embodiments, methods further comprise identifying the particular metabolite. In some embodiments, provided herein are compositions identified by the methods herein.

In some embodiments, systems and methods are provided to allow for the identification of test samples containing unknown molecular species (e.g., molecular species that were not known to be present in the sample prior to analysis) that are unique to the test samples relative to other samples and/or control samples (or present in significantly greater amount in the test samples), and are in sufficient abundance in the test sample to indicate that the unknown molecular species could by synthesized (e.g., biosynthesized) in a useful amount using the same or similar pathways used (e.g., using BGCs that produces the molecular species in the sample).

In some embodiments, FACs or other BGC- or pBGC-containing vectors are expressed in a suitable expression system. In some embodiments, the expression system is an in vitro expression system, cell lysate, or cell. In some embodiments, the expression system is a culture of fungal cells or a fungal cell lysate.

In some embodiments, samples analyzed are extracts prepared from cultured cells, cell lysate, or in vitro expression system. In the case of cultured cells or cell lysate, the cells may be of any suitable source, including eukaryotic (e.g., animal (e.g., mammalian (e.g., human, etc.), etc.), plant, fungus, etc.) or prokaryotic cells (e.g., bacteria). In some embodiments, an extract is prepared to isolate the small molecular species from the culture, lysate, or expression system, and to exclude contaminants (e.g., proteins, cell debris, etc.). Suitable methods for the preparation of small molecule extracts (e.g., from cultures of cells) are understood in the field, and include lyophilization, pulverization, solvent extraction, column purification (e.g., exchange chromatography, size-exclusion chromatography, etc.), filtering, etc.

In some embodiments, native cells (e.g., from a particular species or strain) are cultured, small molecule extracts are prepared from the culture, and the metabolite extracts are analyzed for unique and/or abundant metabolites in comparison to other samples (e.g., extracts from other species/strains, etc.) and/or controls. In some embodiments, cells are grown under and/or exposed to a certain set of conditions and the metabolites in an extract prepared therefrom are compared to extracts prepared from cells grown under and/or exposed to other or control conditions. In some embodiments, metabolites from cells in a diseased or stressed state are compared to cells in a healthy state.

In some embodiments, extracts are prepared from engineered cells, and compared to identify unique and/or abundant metabolites produced by such engineering, compared to native cells, control cells, and/or differently engineered cells. In some embodiments, a nucleic acid vectors is introduced into host cells and/or organisms, and any unique metabolites that result from the introduction of the vector (e.g., compared to control host cells/organisms without the nucleic acid vector, compared to other host cells/organisms with different nucleic acid vectors, etc.) are detected and/or identified.

In some embodiments, a nucleic acid vector (e.g., artificial chromosome (e.g., fungal artificial chromosome), viral vector, plasmid, etc.) encoding a biosynthetic gene cluster (BGC) or putative BGC (pBGC) is introduced in host cells or organisms, cultured, and small molecule extracts are prepared for analysis by the systems and methods described herein. In some embodiments, unique and/or abundant metabolites present in the extract prepared from the culture comprising the BGC-encoding vector (or pBGC encoding vector), compared to extracts prepared from control cultures or those expressing other vectors (e.g., comprising other BGCs or pBGCs), are detected and/or identified.

In some embodiments, analysis of samples (e.g., small molecule extracts) is performed by any suitable bioanalytical (e.g., biophysical and/or biochemical) techniques. In particular embodiments, mass spectrometry is utilized for the analyses described herein. "Mass spectrometry" ("MS") encompasses any spectrometric technique or process in which molecules are ionized and separated and/or analyzed based on their respective molecular weights. Thus, as used herein, "mass spectrometry" encompasses any type of ionization method, including without limitation electrospray ionization (ESI), atmospheric-pressure chemical ionization (APCI) and other forms of atmospheric pressure ionization (API), and laser irradiation. Mass spectrometers are commonly combined with separation methods such as gas chromatography (GC) and liquid chromatography (LC). The GC or LC separates the components in a mixture, and the components are then individually introduced into the mass spectrometer; such techniques are generally called GC/MS and LC/MS, respectively. MS/MS is an analogous technique where the first-stage separation device is another mass spectrometer. In LC/MS/MS, the separation methods comprise liquid chromatography and MS. Any combination (e.g., GC/MS/MS, GC/LC/MS, GC/LC/MS/MS, etc.) of methods can be used to practice the invention. In such combinations, "MS" can refer to any form of mass spectrtometry; by way of non-limiting example, "LC/MS" encompasses LC/ESI MS and LC/MALDI-TOF MS. Also included herein, without limitation, are APCI MS; ESI MS; GC MS; MALDI-TOF MS; LC/MS combinations; LC/MS/MS combinations; MS/MS combinations; etc.

In some embodiments, tandem mass spectrometry (MS2) is employed. Tandem mass spectrometry (MS/MS or MS2) is a technique capable of differentiating large numbers of metabolites in complex biological samples. In a typical experiment, metabolites are separated via, for example, high-performance liquid chromatography (HPLC) and the separated metabolites are injected onto a tandem mass spectrometer. In such an experiment, as the metabolites elute from the liquid chromatography (LC) column, they are subjected to an ionizing voltage and are introduced into the near vacuum environment of the tandem mass spectrometer. A survey scan (e.g., a first mass spectrum or MS1) is obtained to determine the mass-to-charge ratio (m/z) of the intact metabolites that entered the tandem mass spectrometer. The ionized metabolites detected in the first mass spectrum may be referred to as precursor ions. One or more of the precursor ions in the first mass spectrum is selected, sequentially isolated, fragmented and the resulting fragment ion m/z values determined in a second mass spectrum (i.e., MS/MS or MS2). In some embodiments, only precursor ions of interest are selected for generation of the second mass spectrum. The fragment ions detected in the second mass spectrum may be referred to as product ions. This process is repeated to automatically acquire MS/MS spectra of as many of the precursor ions as desired. The charge state and mass are obtained from the first mass spectrum while the fragmentation pattern is recorded in the second mass spectrum. With this information it is possible to identify metabolites in the sample. In some embodiments, MS2 molecular networking is employed to identify metabolites from MS2 data. In a typical case, cosine similarity scores of MS2 spectra are used to identify spectra from the same analyte as being the same. In a typical case, cosine similarity scores of MS2 spectra are used to identify spectra from analytes that are chemically or biologically related as being related.

Mass spectrometry has several advantages, not the least of which is high bandwidth characterized by the ability to separate (and isolate) many molecular peaks across a broad range of mass to charge ratio (m/z). Thus mass spectrometry is intrinsically a parallel detection scheme without the need for radioactive or fluorescent labels, since every amplification product is identified by its molecular mass. Less than femtomole quantities of material can be readily analyzed by MS to afford information about the molecular contents of the sample. An accurate assessment of the molecular mass of the material can be quickly obtained, irrespective of whether the molecular weight of the sample is several hundred, or in excess of one hundred thousand atomic mass units (amu) or Daltons.

In some embodiments, intact molecular ions are generated from amplification products using one of a variety of ionization techniques to convert the sample to gas phase. These ionization methods include, but are not limited to, electrospray ionization (ES), matrix-assisted laser desorption ionization (MALDI) and fast atom bombardment (FAB). Upon ionization, several peaks are observed from one sample due to the formation of ions with different charges. Averaging the multiple readings of molecular mass obtained from a single mass spectrum affords an estimate of molecular mass of the bioagent identifying amplicon. Electrospray ionization mass spectrometry (ESI-MS) is particularly useful for very high molecular weight polymers such as proteins and nucleic acids having molecular weights greater than 10 kDa, since it yields a distribution of multiply-charged molecules of the sample without causing a significant amount of fragmentation.

The mass detectors used in the methods of the present invention include, but are not limited to, Fourier transform ion cyclotron resonance mass spectrometry (FT-ICR-MS), orbitrap, ion trap, quadrupole, magnetic sector, time of flight (TOF), Q-TOF, and triple quadrupole.

In some embodiments, samples are subjected to one or more forms of liquid chromatography (LC), including without limitation high-performance liquid chromatography (HPLC) and reverse-phase high-performance liquid chromatography (RP-HPLC), prior to and/or in conjunction with MS analysis.

HPLC is a separative and quantitative analytical tool that is generally robust, reliable and flexible. Reverse-phase (RP) is a commonly used stationary phase that is characterized by alkyl chains of specific length immobilized to a silica bead support. RP-HPLC is suitable for the separation and analysis of various types of compounds. One of the most important reasons that RP-HPLC has been the technique of choice amongst all HPLC techniques is its compatibility with electrospray ionization (ESI). During ESI, liquid samples are introduced into a mass spectrometer by a process that creates multiple charged ions (Wilm et al., Anal. Chem. 68:1, 1996).

In some embodiments, MS analysis of a sample and/or a set of samples and controls results in a mass spectrum and/or mass spectra (a plot of intensity vs. m/z (mass-to-charge ratio) of a chemical analysis). In some embodiments, methods are provided herein for the analysis of mass spectra to identify unique and/or abundant molecular species within a test sample in comparison to other test samples and/or control samples.

In some embodiments, m/z features are extracted from mass spectra. In some embodiments, each feature in the mass spectrum corresponds to a small molecule in the analyzed sample. Typical metabolomic analyses search for statistically significant differences in relative feature abundances between groups; however, embodiments herein identify features that are qualitatively present in a single sample (e.g., at high abundance), while absent from all other samples and/or controls tested. In some embodiments, these unique and abundant features represent small molecules present in sufficient quantity in the test sample, but not present in other samples. In embodiments in which multiple (e.g. a library) of BGCs and/or pBGCs are expressed in a host and extracts these cultures are analyzed. A unique and abundant feature, detected by the methods and systems herein represents a small molecule product (e.g., secondary metabolite) that is heterologously expressed by only one BGC tested.

In some embodiments, any suitable bioanalytical techniques may find use in generating metabolite-specific features for scoring in the systems and methods herein. Suitable bioanalytical techniques include, but are not limited to mass spectrometry (MS), tandem mass spectrometry (MS2), high performance liquid chromatography (HPLC), gas chromatography, ultra performance liquid chromatography (UPLC), supercritical fluid chromatography, nuclear magnetic resonance (NMR), liquid chromatography-mass spectrometry (LC-MS), gas chromatography-mass spectrometry (GC-MS), liquid chromatography-diode array detection (LC-DAD), capillary electrophoresis-mass spectrometry (CE-MS), liquid chromatography-tandem mass spectrometry (LC-MS2), and other techniques described herein or known in the field. Any technique that identifies features that allow for differentiation of metabolites and scoring thereof based on the criteria herein (e.g., relative uniqueness and relative abundance) may find use in embodiments herein.

In order to test a large number of different samples (e.g., different pBGCs) and to rapidly triage the data and highlight heterologously expressed products, a scoring system was developed to rank features based on their abundance and uniqueness. In some embodiments, compound score (e.g., BGC score (e.g., FAC score)) (i.e., indicator of uniqueness and abundance of a feature relative to other samples and controls) is generated for each feature in each sample to allow ranking of hits within each sample and identification of sample that appeared to contain unique and abundant compounds (e.g., samples highly express unique products (e.g., relative to all other samples and negative controls). In some embodiments, uniqueness is represented by a ratio determined by the abundance of a feature in a test sample (e.g., a pBGC expressed in a host (e.g., a specific FAC strain)), divided by the abundance of that feature in every other sample and/or control (e.g., extracts from hosts expressing other pBGCs or no pBGC) (Equation A).

Ratio of feature $x$ in sample $y$=(abundance of feature $x$ in sample $y$)/(average abundance of $x$ in all other samples)     Equation A:

Theoretically, a feature that is present in one sample (e.g., expressed by one BGC), but absent in all others, would have a ratio of infinity. In practice, because of noise of the system, trace carry over between samples, and/or the tendency of peak picking algorithms to assign non-zero values to noise within a retention time window where an abundant feature has previously been found for a different sample, features that are unique to a specific sample are often assigned Ratios ranging from $5\times10^1$ to $1\times10^9$. In some embodiments, in cases where this does not occur, and features were assigned an abundance of zero, leading to division by zero and a ratio of infinity, the ratio is assigned an arbitrary value (e.g., $9.99\times10^4$) to facilitate downstream analysis.

In some embodiments, to allow quick, direct comparison of features from different samples (e.g., cultures expressing different pBGCs, as well as assessment of whether specific samples contained unique/abundant metabolites (e.g., whether a BGC was likely to express a heterologous feature), the ratio and raw relative abundance of each feature in each sample were combined to create a Compound Score (e.g., BGC Score (e.g., FAC Score) (Equation B). In some embodiments, the $\log_{10}$ of abundance and ratio values are utilized to account for the large dynamic range of signals for each parameter (e.g., which may span several orders of magnitude). In some embodiments, the $\log_{10}$ abundance values are standardized to a normal distribution, allowing comparison between samples (e.g., FAC strains that globally expressed SMs at very different levels and/or were measured on different days). In some embodiments, the standardized $\log_{10}$ abundance is multiplied by the $\log_{10}$ of the ratio for each feature, after filtering out features with negative scores either for $\log_{10}$ ratios or standardized $\log_{10}$ abundances. In some embodiments, the same calculations are made with raw numbers, rather than logs.

Compound Score=(standardized log(abundance))*log (Ratio of feature $x$ in sample $y$))−Score$_{negative\ control}$   Equation B:

A positive compound Score indicates a unique compound is present in the sample in significant abundance (e.g., a pBGC expressed in the culture from which the sample was derived, expressed a unique secondary metabolite).

In some embodiments, provided herein are systems and methods for the untargeted detection and/or identification of small molecules in samples. In some embodiments, the systems and methods herein allow untargeted correlation of previously unrecognized secondary metabolites to the BGCs responsible for their biosynthesis.

EXPERIMENTAL

Example 1

Identification of Secondary Metabolites and Biosynthetic Gene Clusters

Methods
Generation of FACs from Aspergilli

Unbiased random shear FAC libraries of fungi were generated by using high molecular weight (HMW) genomics DNA of the *Aspergillus* species, BGC-containing FACs were identified by FAC end sequences aligned with their reference genomes and confirmed through PCR. Entire sets of 48 BGCs of *A. aculeatus,* 61 BGCs of *A. terreus* and 47 BGCs from *A. wentii* were captured each on individual FAC clones, 56 of 156 BGC-containing FACs were used. The methods of FAC libraries and BGC-containing FAC identification were used for capturing BGC-containing FACs from all three fungal species.

Transformation of FACs into Host Strain

FAC DNA was transformed into an *A. nidulans* host strain.

Extraction of Secondary Metabolites

Each *A. nidulans* FAC transformant was inoculated on four solid glucose minimal medium plates supplemented with pyridoxine (1 mL of 0.1% stock solution) and incubated for seven days at 37° C. Subsequently, the entire contents of the plates were collected and lyophilized for 48 hours. Samples were then pulverized with mortar and pestle prior to the addition of 10 mL of methanol. Air-dried methanol extracts were then further extracted with organic solvent (chloroform:methanol:ethylacetate 8:1:1). Organic extracts were evaporated to dryness and stored at −20° C. until analysis.

Untargeted Metabolomic Screening of FAC Extracts

Dried biological quadruplicate extracts of each *A. nidulans* FAC strain were resuspended to a concentration of 2 mg/mL by addition of 50% acetonitrile, followed by bath sonication for 10 minutes. Insoluble material was removed by centrifugation at 21,000×g for 10 minutes. The supernatant of each reconstituted extract was then transferred to an LC-MS autosampler vial and stored at 4° C. until analysis.

Samples were analyzed by high resolution HPLC-MS/MS using a Thermo Q-Exactive in line with an electrospray source and an Agilent 1200 series high performance liquid chromatography stack (HPLC) consisting of a binary pump, degasser, and autosampler, outfitted with a Phenomenex Luna C-18 column with dimensions of 2 mm×150 mm, 3 µm dp. A binary linear gradient of water and Acetonitrile balanced with 0.1% formic acid was used (Buffer A: H2O, Buffer B: acetonitrile) and 50 µg of extract (25 µL), was injected. The gradient was at 0 minutes: 2% B, 35 minutes: 70% B, and 54 minutes: 98% B, with a flow rate of 200 µL/min. A 1:4 split was used to transfer sample from the column to the electrospray source, so the flow rate into the ESI source was 50 µL/min. The capillary of the ESI source was set to 275° C., with sheath gas set to 5 arbitrary units and spray voltage set to 3.5 kV. MS1 data was collected at 70,000 resolution from 150 to 2,000 m/z. MS2 scans for the 5 most abundant ions in each MS1 scan were collected at a resolution of 35,000, with a 60 s exclusion list. Fragmentation was achieved using the higher energy collisional dissociation (HCD) cell set to NCE 30. To minimize the effect of instrumental drift over time, samples were run in a randomized queue. All FACs from a given species were analyzed together in a single sequence, along with a set of biological quadruplicates from empty FAC. Extracts from parent strains grown on the 5 media listed above were run separately from FAC extracts, in order to minimize the possibility of carry over.

Feature Detection of Untargeted Metabolomic Data

Chromatographic and m/z features were extracted and grouped using the open source metabolomics software XCMS, running in R. Raw files were converted to mzML format using the msconvert algorithm from Proteowizard, operating from the command line. FACs from the same species were analyzed together. First, all mzML files for a species (i.e. *A. terreus, A. wentii* or *A. aculeatus*) were placed in a parent directory along with the empty FAC controls they were run with. This ranged from 48 to 104 files depending on the species. Then, a subdirectory was created for each set of biological quadruplicates corresponding to a specific FAC or empty FAC negative control. XCMS was run in R using the centwave algorithm for feature detection with the following parameters: ppm=3, peakwidth=c(20, 100), snthresh=10, prefilter=c(5,10000), mzCenterFun="wMean", integrate=1, mzdiff=0.001, fitgauss=FALSE, noise=1000. Grouping was then carried out using the group command and the parameters: bw=30, minfrac=0.5, mzwid=0.01. Following grouping, retention time correction was carried out using the algorithm retcor with the parameters: family="s", plottype="m". Typical retention time deviations ranged from 0 to 100 s, with the vast majority of features having less than 10 s deviations. After retention time correction, features were re-grouped and then subjected to peak filling using the algorithm pkfill. To further annotate features, the software suite CAMERA was used in R to identify isotopically related features and features related by adduction. Results from XCMS and CAMERA were output into a .csv file. Generally, about 12,500 features were detected for each species, with the abundance of each feature in each extract and treatment being recoded. The commands used for XCMS and CAMERA are given in Figure XCMS.

Untargeted LC-FTMS screening of extracts from 29 FACs, encompassing approximately 3 Mbp of biosynthetic gene clusters was followed by automated peak picking. This lead to assignment of ≃'10,000 features to each FAC. Typical untargeted metabolomic analyses search for statistically significant differences in relative feature abundances between treatment groups; however, experiments conducted during development of embodiments herein focused on features that were qualitatively present in a single FAC strain at high abundance, while absent from all others, i.e., products that were heterologously expressed by only one FAC. Therefore, in order to rapidly triage data and highlight heterologously expressed FAC products, a scoring system was developed to rank features based on their abundance and uniqueness to each FAC.

Generation of FAC Scores

A FAC score for each feature in each FAC was generated to allow ranking of hits within each FAC and identification of FAC strains that appeared to highly express unique (relative to all other FACs and the negative control for a species) heterologous products. Uniqueness was represented by a ratio determined by the abundance of a feature in a specific FAC strain, divided by the abundance of that feature in every other FAC strain (Equation 1). Theoretically, a feature that was present in one FAC strain, but absent in all others, has a ratio of infinity. In practice, because of carry over between samples, as well as the tendency of peak picking algorithm's to assign non-zero values to noise within a retention time window where an abundant feature has previously been found for a different sample, features that are unique to a specific FAC strain are often assigned high rational values ranging from $5 \times 10^1$ to $1 \times 10^9$. In cases where this did not occur and features were assigned an abundance of zero, leading to division by zero and a ratio of infinity, the ratio was assigned an arbitrary value of $9.99 \times 10^4$ to facilitate downstream analysis.

$$\text{Ratio of feature } x \text{ in } FAC\ y = \frac{\text{Average abundance of feature } x \text{ in } FAC\ y}{\text{Average abundance of feature } x \text{ in all other } FACs} \quad \text{Equation 1}$$

To allow quick, direct comparison of features from different FACs, as well as assessment of whether specific FACs were likely to express a heterologous feature, the ratio and raw relative abundance of each feature in each FAC were combined to create a FAC score (Equation 2). The $\log_{10}$ of abundance and ratio values were utilized to account for the large dynamic range of signals for each parameter (which spanned several orders of magnitude). Then the $\log_{10}$ abundance values were standardized to a normal distribution, allowing comparison between FAC strains that globally expressed SMs at very different levels and/or were measured on different days. The standardized $\log_{10}$ abundance was then multiplied by the $\log_{10}$ of the ratio for each feature, after filtering out features with negative scores either for $\log_{10}$ ratios or standardized $\log_{10}$ abundances.

$$FAC\ \text{Score} = (\text{standardized log(abundance)} \times \text{log(ratio)}) - \text{Score}_{negative\ control} \quad \text{Equation 2}$$

The result of these calculations was a score for each feature. The highest scoring feature from empty, negative control FAC strains ranged from 3.2 to 3.8, with an average of 3.4. The average negative control score was subtracted from the score for each FAC to give the final FAC score. Thus, FACs with positive scores (29/56) were deemed likely to express heterologous BGC products. Manual analysis of these hits revealed that in 17 cases the top feature was unique only to that FAC and was not a known metabolite of the heterologous host strain (*A. nidulans*) based on dereplication using the Dictionary of Natural Products VERSION (DNP) and Antibase VERSION databases of fungal natural products.

Identification of Benzomalvin A/D

Due to its expression of an unusually high number of abundant and unique metabolites, AtFAC9J20 was selected for intensive follow. Manual analysis revealed that all of the top scoring features were adducts of the ion with m/z 382.1547 and RT of 38 and 41 min. This m/z did not match any known fungal metabolites in either DNP or Antibase. To broaden the dereplication search, the online tool MAGMA was used to search simulated MS2 data for every molecule of the same mass in pubchem against MS2 data attained for AtFAC9J20. The top three hits were synthetic compounds, however the fourth was benzomalvin A/D. Fragments were then assigned using the program Mass Frontier 7.0 (Thermo, San Jose, Calif.) and a starting hypothesis of benzomalvin A/D as the parent compound, resulting in assignment of all major fragments.

Sequence Analysis of the AtFAC9J20(Chr.4: 2,151, 734~Telomeric End)

Figure 8:
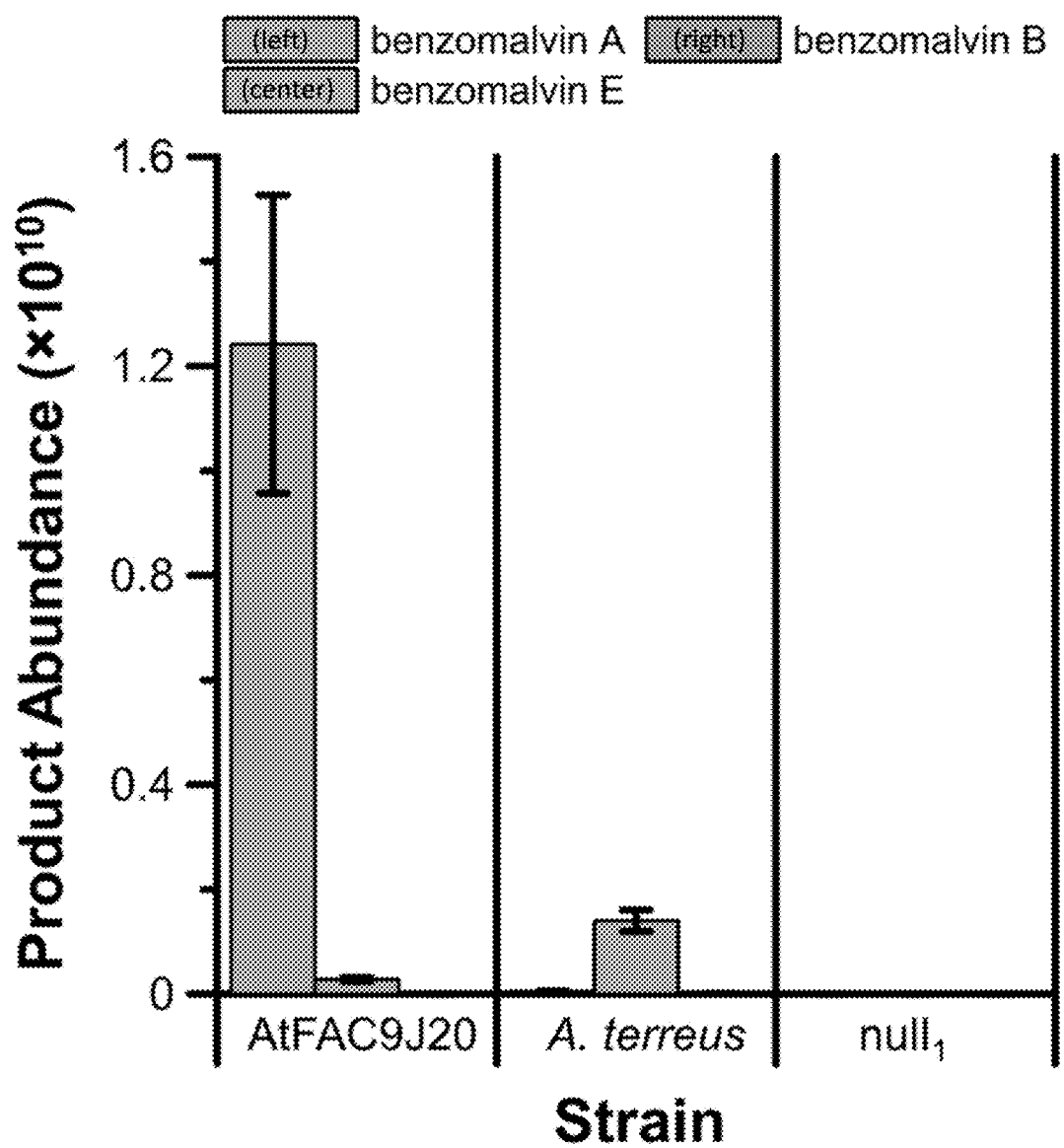
FIG. 8. Abundance of benzomalvins in AtFAC9J20-transformed strain. Amount of benzomalvins A+D, E, and B produced by AtFAC9J20, *A. terreus*, and AtFAC9J20-null1.

The insert of AtFAC9J20 was sequenced to identify genes involved in benzomalvin production. Interestingly, 17 ORFs, eight of which are missing in the genome data of *A. terreus* NIH 2624 (Table FAC ORF), were detected. The eight unique ORFs included two predicted NRPS enzymes, benY and benZ, with domain structures of A-T-C and A1-T1-C1-A2-T2-C2, respectively. The extracted 10 amino acid A domain signatures for both the A domain of benY and the A1 domain of benZ match the distinct signature expected for Anth-encoding A-domains (ref). The A2 domain of benZ is predicted to encode a Phe, NmPhe, or Tyr residue. In addition to benY and benZ, the gene benX was discovered, which encodes a predicted SAM-binding N-methyl transferase enzyme and is the only standalone methyl transferase in AtFAC9J20. Additionally, ORFs encoding a predicted PKS, a third NRPS enzyme, and an isoprenoid synthase enzyme were found on the FAC and annotated (FIG. 8).

Synthesis and LC-MS/MS Analysis of Benzomalvin A/D

Synthesis of Benzomalvin A/D was carried out to confirm the identity of the AtFAC9J20 ion with m/z 382.1547 as follows. N-desmethylbenzomalvin A/D was synthesized following the methodology presented in (ref) replacing Pd/C, H2 nitro reduction with Zn/AcOH, RT 12 h. N-desmethylbenzomalvin A/D was methylated with LiHMDS (1.1 eq) and methyl iodide (1.2 eq) in THF to give crude benzomalvin A/D. An analytical sample for LC-MS/MS was prepared by preparative HPLC using a Higgins Analytical 250×10 mm TARGA C18 5 μm column eluted with buffers A (water 0.1% TFA) and B (acetonitrile 0.1% TFA) at 7.5 ml/min. The gradient was ramped from 95% A to 95% B over 12 mins followed by re-equilibration. 1H NMR (500 MHz, Acetone-d6) δ 8.23 (dd, J=7.9, 1.5 Hz, 1H), 7.90 (ddd, J=8.5, 7.0, 1.5 Hz, 1H), 7.85 (dd, J=8.1, 1.3 Hz, 1H), 7.83 (dd, J=7.7, 1.7 Hz, 1H), 7.70-7.67 (m, 1H), 7.67-7.62 (m, 1H), 7.59 (dddd, J=7.2, 5.5, 4.2, 1.4 Hz, 2H), 7.37 (d, J=6.8 Hz, 1H), 7.32-7.20 (m, 3H), 7.19-7.13 (m, 1H), 5.08 (t, J=7.4 Hz, 1H), 3.77 (dd, J=14.6, 7.4 Hz, 1H), 3.55 (dd, J=14.6, 7.5 Hz, 1H), 3.03 (s, 3H). 13C NMR (126 MHz, Acetone-d6) δ 161.85, 153.72, 138.42, 135.60, 134.21, 132.97, 131.30, 130.26, 130.03, 129.93, 129.71, 129.46, 129.35, 129.04, 128.53, 128.24, 127.86, 127.47, 122.82, 59.29, 33.74, 27.91.

Synthetic benzomalvin A/D was then analyzed by LC-MS/MS as described for FAC extracts above, and its selected ion chromatogram (SIC) for benzomalvin A/D was compared to the SIC for m/z 382.1547 in extract from *A. terreus* and AtFAC9J20, confirming the identification of the unknown compound as benzomalvin A/D

Production of FAC Deletants

FAC deletants, FACs lacking a portion of the BGC, were produced for further analysis.

Analysis of FAC Deletants

FAC deletant extracts were resuspended and analyzed by HPLC-MS/MS as described above in blocks of biological quadruplicates with two blanks run in between each biological treatment to minimize sample carry over. The integrated total ion current (TIC) was determined for each feature, as well as the integrated peak area for each feature of interest based on a 4 minute retention time window and a 10 ppm m/z window. The resulting values were used to calculate the fraction of TIC accounted for by each feature (fracTIC). Values from biological quadruplicates were averaged and error bars were generated by standard deviation. FAC-at20 normalized abundances for features of interest were determined by dividing the fracTIC of a feature from a given deletant by the fracTIC for AtFAC9J20. Error bars for AtFAC9J20 normalized values were generated through propagation of error using the standard deviation for each value.

Results

A standardized collection of FACs was created by capturing ~100 kilobase inserts of random shear libraries of genomic DNA from *A. wentii*, *A. terreus*, and *A. aculeatus* (FIG. 1 Panel a), three *Aspergillus* species from diverse taxa in this genus (e.g. sections Cremei, Terrei and Nigri respectively). We hypothesized we would capture more distinct BGCs in this manner as *Aspergillus* sections are based in part on differences in their chemical repertoire (ref). The FAC libraries were screened by FAC end-sequencing and reference genome alignment, leading to confirmation of 156 FACs each encoding a predicted BGC of *A. wentii*, *A. terreus*, or *A. aculeatus* (note that each organism has a sequenced or reference genome available). The backbone of the FAC vector allows self-propagation in both *A. nidulans* and *E. coli*, making amplification, manipulation, and heterologous expression of secondary metabolites facile at all stages (FIG. 1, vide infra). Fifty-six distinct FACs, each containing one or more orphan BGCs, were selected due to their lack of homology with characterized systems and transformed into *A. nidulans* for growth and extraction of metabolites (FIG. 1 Panel b).

Figure 2:
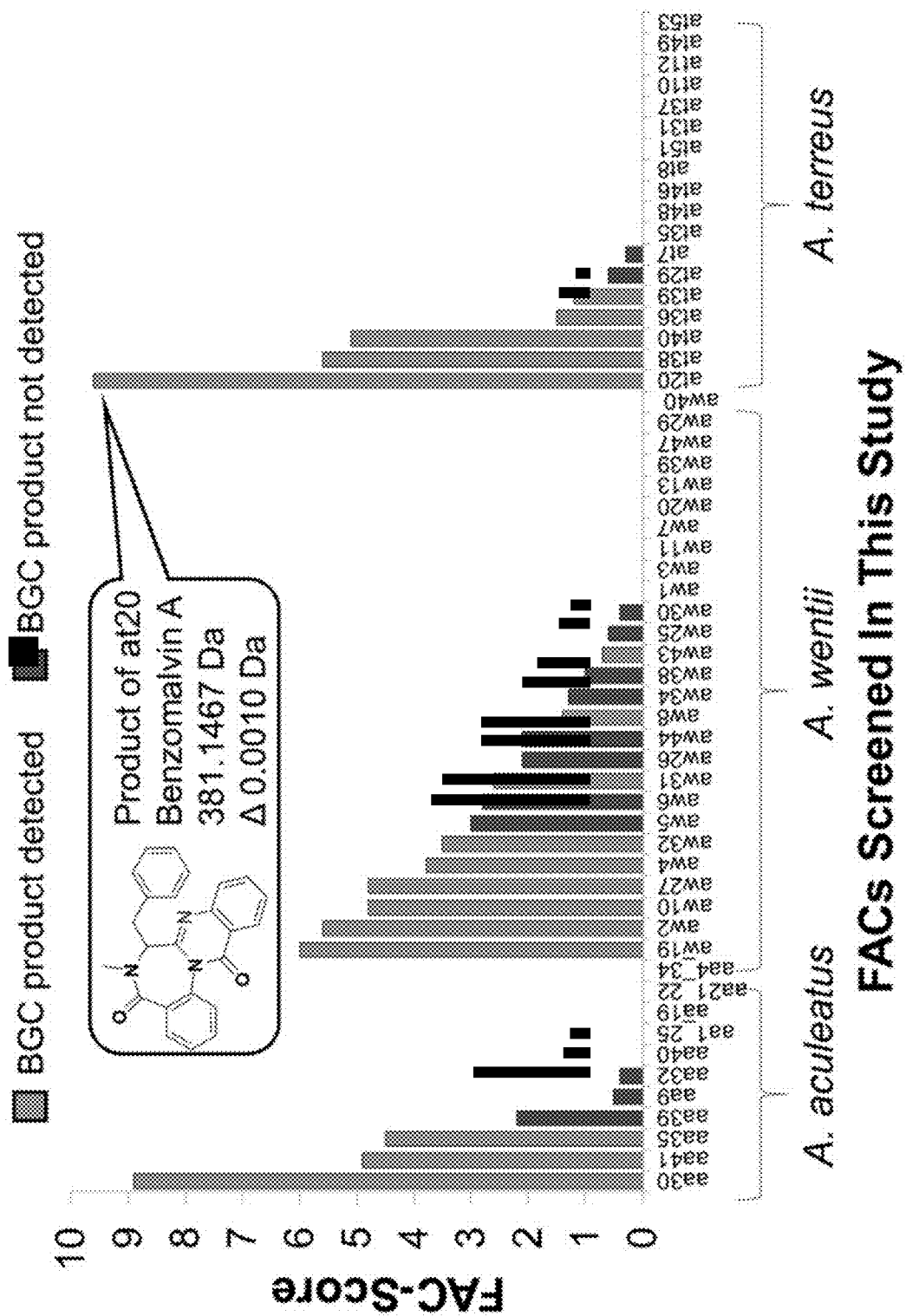
FIG. 2. Bars show score of top spectral feature from each FAC. Black bars indicate FACs which products were not detected. Gray bars represent FACs which BGC products were detected. FACs without visible bars lacked spectral features with positive scores.

Extracts from the 56 FAC-transformed strains (each grown in biological quadruplicate, repeated from the step of transformation) were subjected to LC-MS and feature detection (FIG. 1 Panel c). After data workup, we applied the scoring routine developed for FAC-MS (see Online Methods). All individual features were scored for a given FAC; and the final strain-representative FAC-score was taken as the highest scoring metabolite from a given extract minus the average FAC-score from a set of 12 negative controls (i.e., extracts from *A. nidulans* containing a FAC backbone with no insert). FAC-scores for each feature in the entire study ranged from −1.9 to 9.6, where values >0 represented FACs where heterologous BGC products were possibly detected. Study-wide, 29/56 FACs received scores >0. Manual analysis of these hits revealed that the top scoring product from 17 different FAC-strains were likely to be unique to a given FAC and its encoded BGC (FIG. 2, FIG. 17, Table 1), while 12 appeared to express products which were detected in other FAC strains or the negative controls at lower levels (red bars, FIG. 2), indicating they were not FAC-encoded or resulted from cross contamination.

TABLE 1

FAC Hits

| Species | FAC | FAC Score | Product m/z | Deletant validated? |
|---|---|---|---|---|
| A. wentii | aw19 | 6 | 423.1790 | |
| A. wentii | aw2 | 5.6 | 988.5568 | |
| A. wentii | aw10 | 4.8 | 680.3561 | |
| A. wentii | aw27 | 4.8 | 542.3566 | |

TABLE 1-continued

FAC Hits

| Species | FAC | FAC Score | Product m/z | Deletant validated? |
|---|---|---|---|---|
| A. wentii | aw4 | 3.8 | 577.3177 | |
| A. wentii | aw32 | 3.5 | 718.4080 | |
| A. wentii | aw31 | 2.6 | 736.2050 | |
| A. wentii | aw8 | 1.4 | 542.3857 | |
| A. wentii | aw43 | 0.7 | 402.2614 | |
| A. aculeatus | aa30 | 8.9 | 403.2026 | |
| A. aculeatus | aa41 | 4.9 | 443.1906 | |
| A. aculeatus | aa35 | 4.5 | 274.0357 | |
| A. terreus | at20 | 9.6 | 382.1543 | Yes |
| A. terreus | at40 | 5.1 | 674.2699 | |
| A. terreus | at36 | 1.5 | 610.9250 | |
| A. terreus | at39 | 1.2 | 278.2110 | |

In order to distinguish known vs. novel compounds, the 17 unique products were subjected to dereplication against the exact masses of ~280,000 known natural products, as well as through comparison of their observed MS2 spectra to computationally predicted MS2 spectra of compounds in PUBCHEM. 16/17 FAC products could not be matched in this manner to known molecules. The 17th product, from AtFAC9J20, was found to express the orphan benzodiazepine molecule benzomalvin A, which had no reported BGC, but is expected to be biosynthesized through incorporation of anthranilate, based on its structure. AtFAC9J20 also expressed several other high scoring spectral features which appeared unrelated to benzomalvin A based on MS2.

Figure 5:
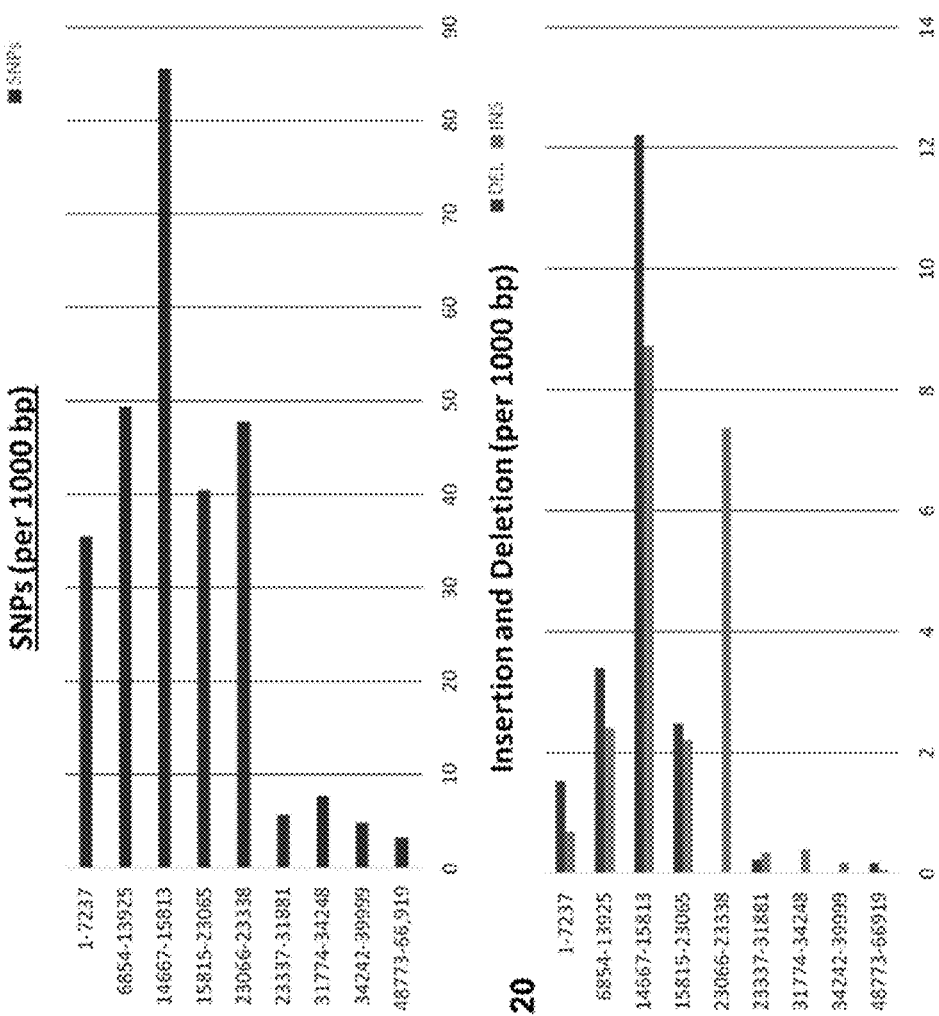
FIG. 5. Distribution of genetic variations of AtFAC9J20 vs. reference genome sequence.

AtFAC9J20 was derived from an unsequenced strain of *A. terreus* ATCC 20542 (Chr. 4: 2,151,734~telomeric end) and contained an insert of 102,722 bp that was resequenced and annotated (Table 3 and FIG. 5). The FAC sequence also contained ~36 kb missing sequence as well as many other types of genomic variation not found in the sequenced *A. terreus* NIH 2624 strain (Table 3 and FIG. 5). To physically map the backbone genes to their BGC and resultant metabolites, deletants of each predicted backbone gene from AtFAC9J20 were produced (Table 3).

TABLE 2

AtFAC9J20 Deletants.

| Deletant Name | Genes Deleted | Benzomalvin A/D Detected? | Terpenoid Detected? | Lipopeptide Detected? |
|---|---|---|---|---|
| Null | benX, benY, benZ, nrps 3, pks | No | Yes | No |
| ΔbenX | benX | Yes | Yes | Yes |
| ΔbenY | benY | No | Yes | Yes |
| Δbenz | benZ | No | Yes | Yes |
| Δnrps3 | nrps3 | Yes | Yes | No |
| Δpks | pks | Yes | Yes | No |
| Δterp | Terpene synthase, adjacent ORFs | Yes | No | Yes |

After deletants were generated, they were transformed into *A. nidulans*, grown, extracted, screened by LC-MS, and scored as before to assign genes to metabolites and dissect BGC biosynthetic pathways (FIG. 1 Panel e).

TABLE 3

AtFAC9J20 re-sequencing alignment
Alignment of AtFAC9J20 and the ref genome sequence (NIH strain)

| AtFAC9J20 | NIH Ref-genome | Large Variations | Location |
|---|---|---|---|
| 102,551-102,702 (Telo) | no data | NA | NA |
| 66,920-102,550 | no data | NA | NA |
| 48,773-66,919 | 42,395-60,545 | 10bp duplication in this strain | intergenic |
| 40,000-48,772 | missing | (+)8,773 bp | intergenic |
| 34,242-39,999 | 36,648-42,404 | | |
| missing | 36,304-36,647 | (−)344bp | intergenic |
| 31,774-34,248 | 33,830-36,303 | 7bp duplication in the NIH strain | |
| missing | 33,724-33,829 | (−)106bp | intergenic |
| 23,337-31,881 | 25,175-33,723 | 2bp duplication in this strain | intergenic |
| missing | 24,806-25,174 | (−)369bp | intergenic |
| 23,066-23,338 | 24,805-24,541 | 265bp inversion | intergenic |
| missing | 24,445-24,540 | (−)96bp | intergenic |
| 15,815-23,065 | 17,183-24,444 | | |
| missing | 15,332-17,182 | (+)2bp and (−)1,851bp | intergenic |
| 14,667-15,813 | 14,166-15,331 | | |
| 13,926-14,666 | missing | (+)741bp and (−)8bp | A10(14,101-14,925) |
| 6854-13925 | 7072-14159 | 207 or 225bp duplication in the NIH strain | A11(7,736-6,762) |
| 1-7237 | 1-7248 | | |

AtFAC9J20—Cluster #1: Benzomalvin A/D and its Biosynthetic Genes (FAC-Score of 9.6)

Figure 7A:
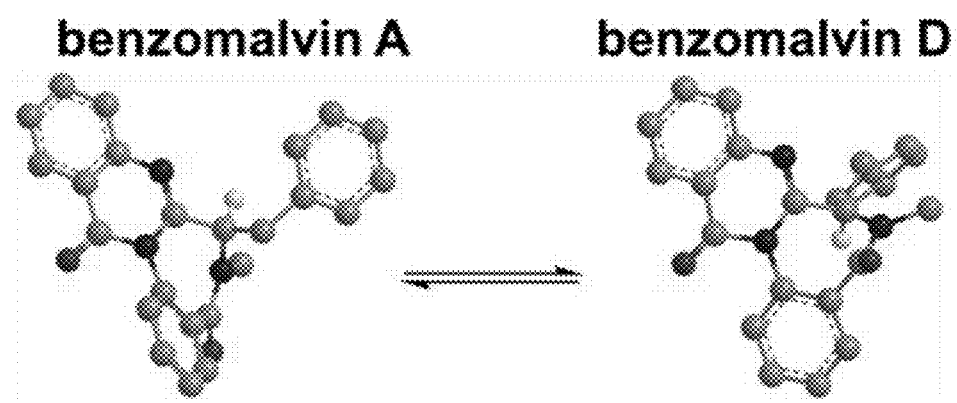
FIGS. 7A-B. AtFAC9J20 produces benzomalvin A/D and atropisomer benzomalvin D. (A) Benzomalvin A/D is in equilibrium with its atropisomer, benzomalvin D. (B) Peaks corresponding to each atropisomer are shown a 38 and 41 minutes. Based on relative peak abundance, it is expected that benzomalvin A/D is the peak at 38 min and benzomalvin D at 41 min.
Figure 7B:
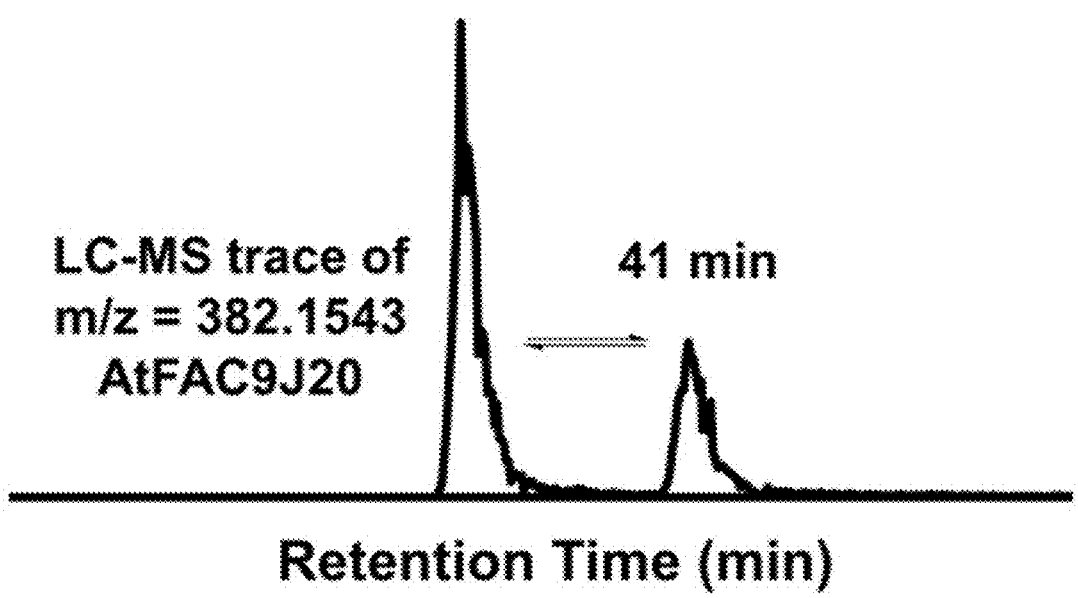

The highest scoring feature of AtFAC9J20, dereplicated as benzomalvin A, showed an ion feature with m/z=382.1547 with two different retention times of 38 and 41 min. Prediction of chemical formulae from the accurate mass gave C24H19N3O2 (observed: 381.1474, theoretical: 381.1477 Da, error −1 ppm), matching the formula of protonated benzomalvin A. This identification was also consistent with the observation of two chromatographic peaks, since benzomalvin A is known to undergo a spontaneous conformation change to form a mixture of benzomalvin A and its atropisomer benzomalvin D, which has a different retention time when separated by reverse phase chromatography, but identical atomic connectivity (FIG. 7). The identity of the compound was unambiguously confirmed by total synthesis of an LC-MS standard for benzomalvin A/D and direct comparison to the observed product of AtFAC9J20.

Figure 6A:
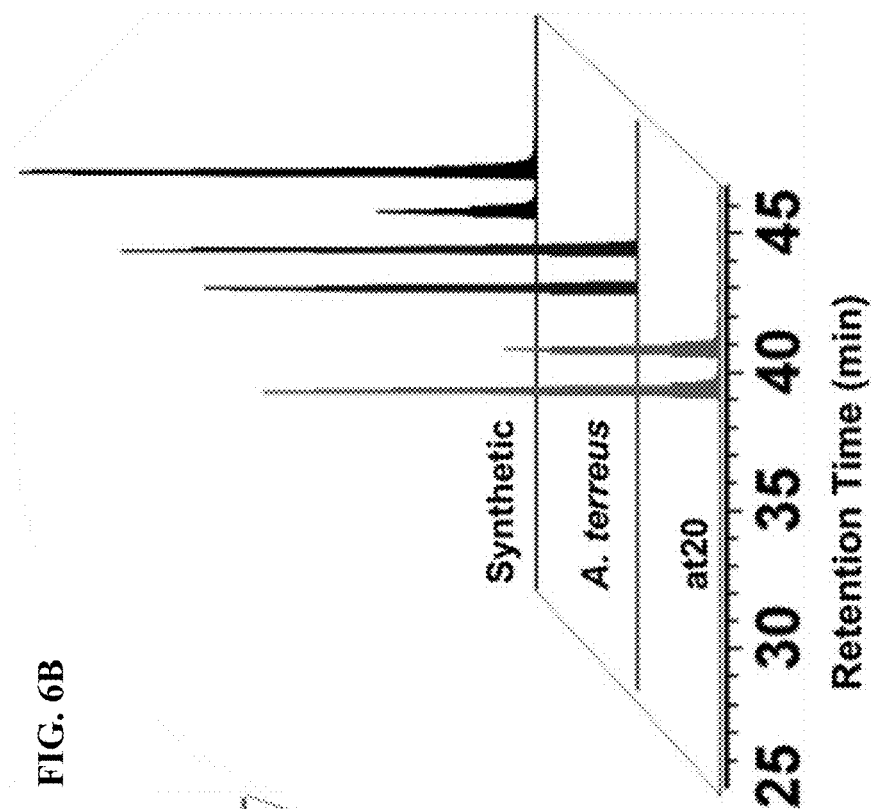
FIGS. 6A-C. AtFAC9J20 encodes BGC for benzomalvin A/D. (A) Selected ion chromatograms of 382.1545±5 ppm reveal an unknown, highly abundant ion unique to extracts from AtFAC9J20. (B) Benzomalvin A/D was synthesized as previously described and analyzed by LC-MS/MS. Retention time and m/z of the synthetic standard matches the ion detected at 382.1545, found in both AtFAC9J20 extract and extract from *A. terreus* ATCC20524. (C) MS2 of ion at m/z=382.1545 of the synthetic standard matches that of AtFAC9J20, together with coelution, confirming the identity of the unknown ion as Benzomalvin A/D.
Figure 6B:
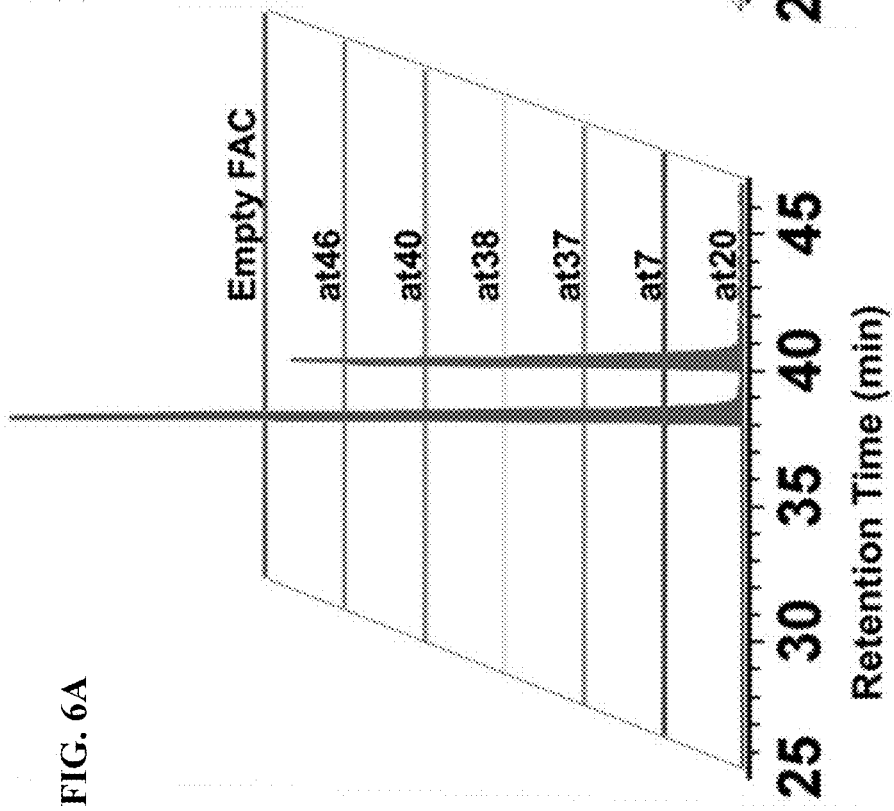
Figure 6C:
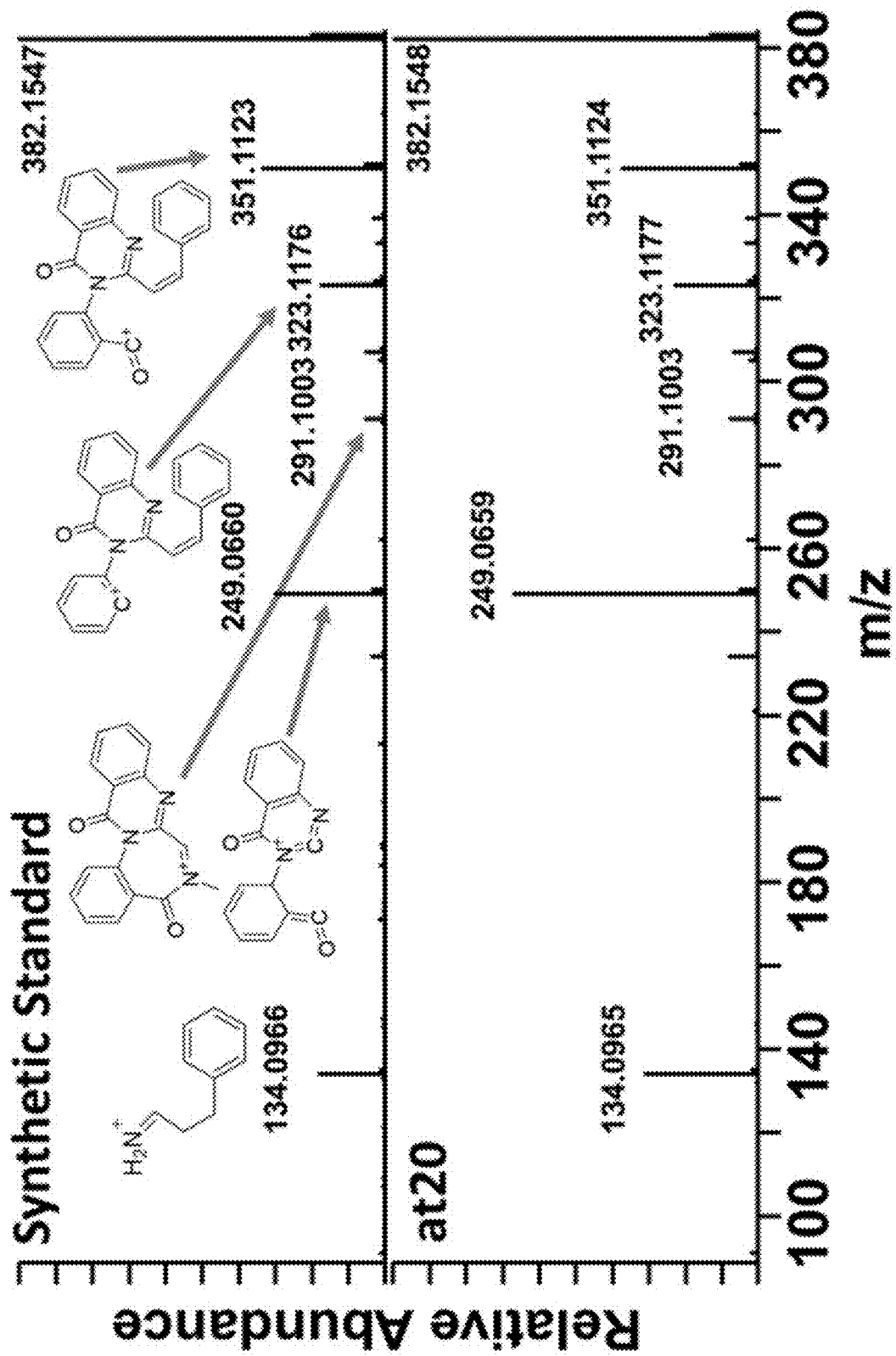

Extracts from the parent *A. terreus* strain (ATCC 20542), also contained benzomalvin A/D based on matching retention times, accurate mass, and MS2 data (FIG. 6), though at ~350-fold lower abundance (FIG. 8). By contrast, benzomalvin A/D was not detected in the sequenced reference strain of *A. terreus*, strain NIH 2624. Additionally, two other known benzomalvins, benzomalvins E and B, were also detected in AtFAC9J20 and the parent *A. terreus* ATCC 20524 strain based on accurate mass and MS2 data. The biosynthetic gene cluster of benzomalvin has not been previously reported, however benzomalvins have bioactivity against the human proteins 2,3-indoleamine dioxygenase and the substance P receptor NK1.

Figure 3A:
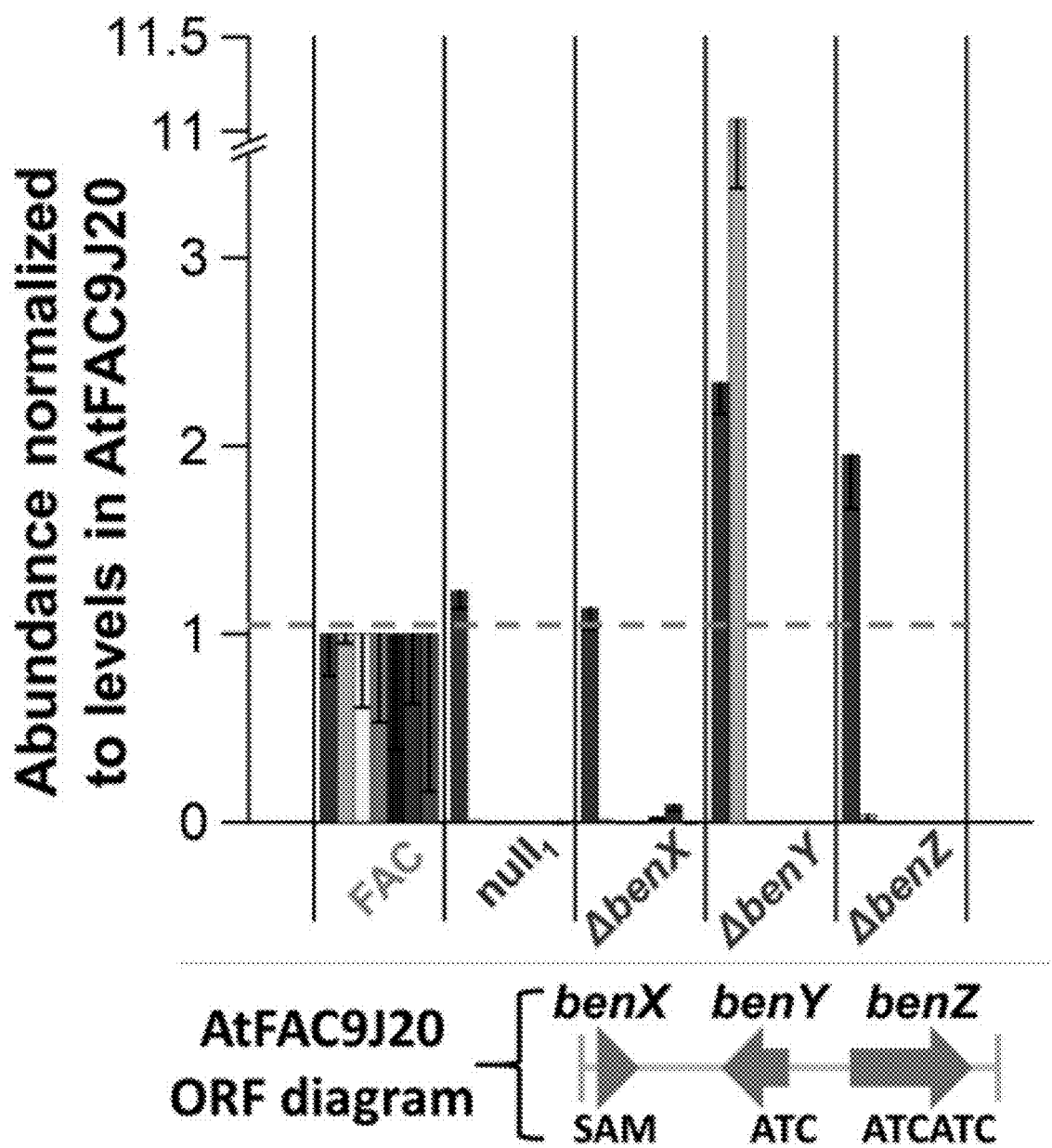
FIGS. 3A-B. Analysis of benzomalvin A/D biosynthesis. (A) The abundance of each predicted benzomalvin precursor and product is shown for AtFAC9J20, null1, AtFAC9J20ΔbenX, AtFAC9J20ΔbenY, and AtFAC9J20ΔbenZ, normalized to abundance in AtFAC9J20, which is signified by the horizontal dashed line (at unity). Deletants of benY, and benZ both abolish the signal of every intermediate and product, with the exception of the monomeric NmPhe precursor, and the dipeptide Anth-NmPhe in the case of benY. Deletion of benX substantially decreases, but does not eliminate the levels of each product and intermediate, consistent with the presence of host methyl transferase activity. Notably, NmPhe levels are not affected by deletion of benY or benZ, but are significantly decreased by deletion of benX, demonstrating that benX generates NmPhe. (B) Based on the deletant data, the biosynthesis of benzomalvin A/D is proposed by the enzymes benX, benY, and benZ, followed by the production of benzomalvin E and B at low levels either through a host enzyme (benzomalvin E) or through spontaneous elimination of water (benzomalvin B).
Figure 10:
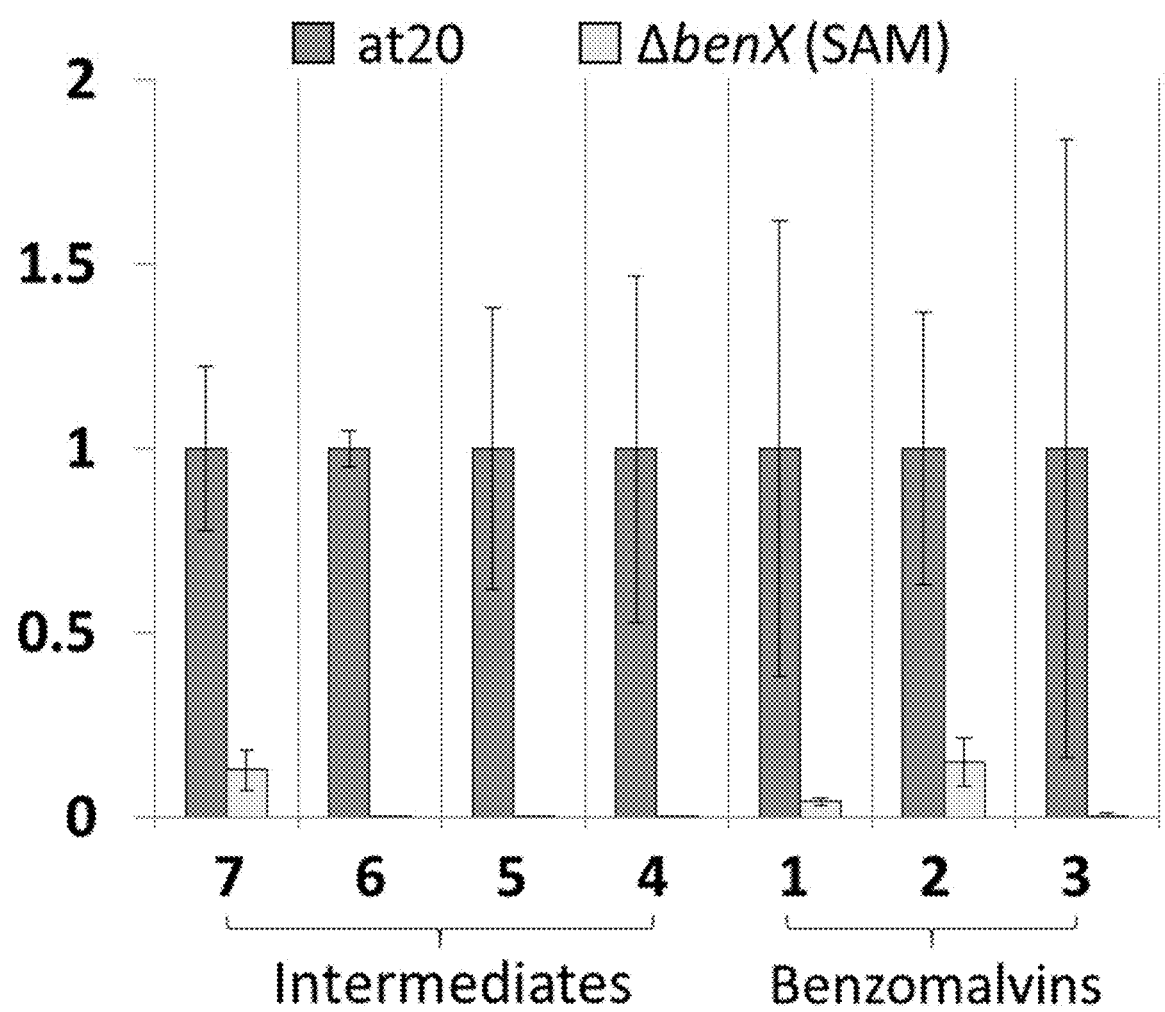
FIG. 10. Effect of deletion of AtFAC9J20 predicted methyltransferase benX. The level of each predicted benzomalvin biosynthetic intermediate and product (normalized to the levels observed in AtFAC9J20) is shown for AtFAC9J20 and the predicted methyltransferase deletant, ΔbenX. Deletion of benX reduces the levels of all intermediates and products, including NmPhe (7). Low levels of each intermediate and product are likely still observed because of activity by a host N-methyltransferase enzyme.
Figure 11:
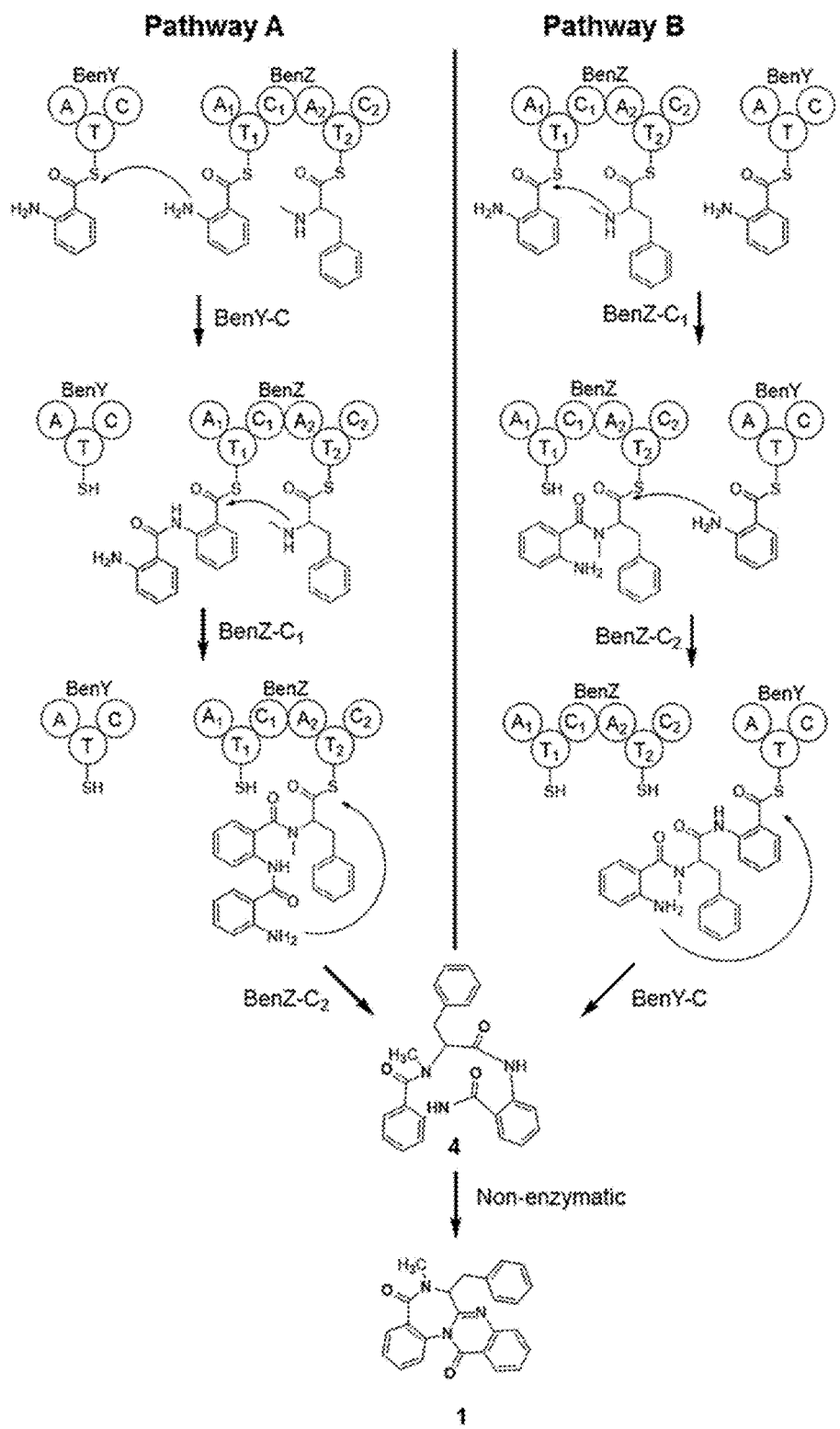
FIG. 11. Models of benzomalvin biosynthesis.

Two putative NRPS genes identified in AtFAC9J20 were predicted to encode Anth-incorporating A domains, but were absent from the sequenced strain of *A. terreus* NIH 2624. FIG. 3a shows that deletion of the half of the AtFAC9J20 insert encoding the two putative Anth-incorporating NRPS proteins, the predicted methyltransferase, a third NRPS, and a predicted PKS eliminated all significant benzomalvin A/D signal (deletant labeled as null1, FIG. 4a). Meanwhile, deletion of the opposite half of the insert (deletant labeled as null2, FIG. 4a) had no significant effect on benzomalvin A/D levels. Individual gene deletions were then performed for each of the 3 predicted NRPS genes, the predicted methyltransferase gene, and the predicted PKS gene. Only deletion of two of the NRPS genes (noted benY and benZ) and the predicted methyltransferase (benX) had any significant effect on benzomalvin A/D production with the former abolishing it entirely and the latter decreasing it ten-fold (FIG. 3a). Interestingly, deletion of benY led to accumulation of the predicted benzomalvin A/D dipeptide precursor, Anth-NmPhe, while deletion of benZ eliminated the dipeptide precursor, suggesting the bimodular benZ is responsible for production of this dipeptide (FIG. 3a). Deletion of the predicted SAM-binding methyltransferase gene benX lead to a ten-fold decrease in benzomalvin A/D level, but not its complete removal (FIG. 3a and FIG. 10). It is contemplated that this is due to activity of a promiscuous host methyltransferase enzyme partially rescuing the benX deletant.

TABLE 4

Extracted A Domain Signatures of NRPS genes encoded by AtFAC9J20

| Domain | SEQ ID NO: | Extracted A-domain Signature | SEQ ID NO: | Predicted Amino Acid |
|---|---|---|---|---|
| BenY-ATC | 1 | GMFIVGLGMK | 4 | Anth |
| BenZ-ATCATC | 2 | GINFIGAGTK | 5 | Anth |
| BenZ-ATCATC | 2 | DMNVMGGVTK | 6 | Phe, NmPhe, Tyr |
| NRPS3-CATCATC | 3 | DALLLGITIK | 7 | Branched Aliphatic |
| NRPS3-CATCATC | 3 | DLGFSGPIIK | 8 | Branched Aliphatic |

Figure 9A:
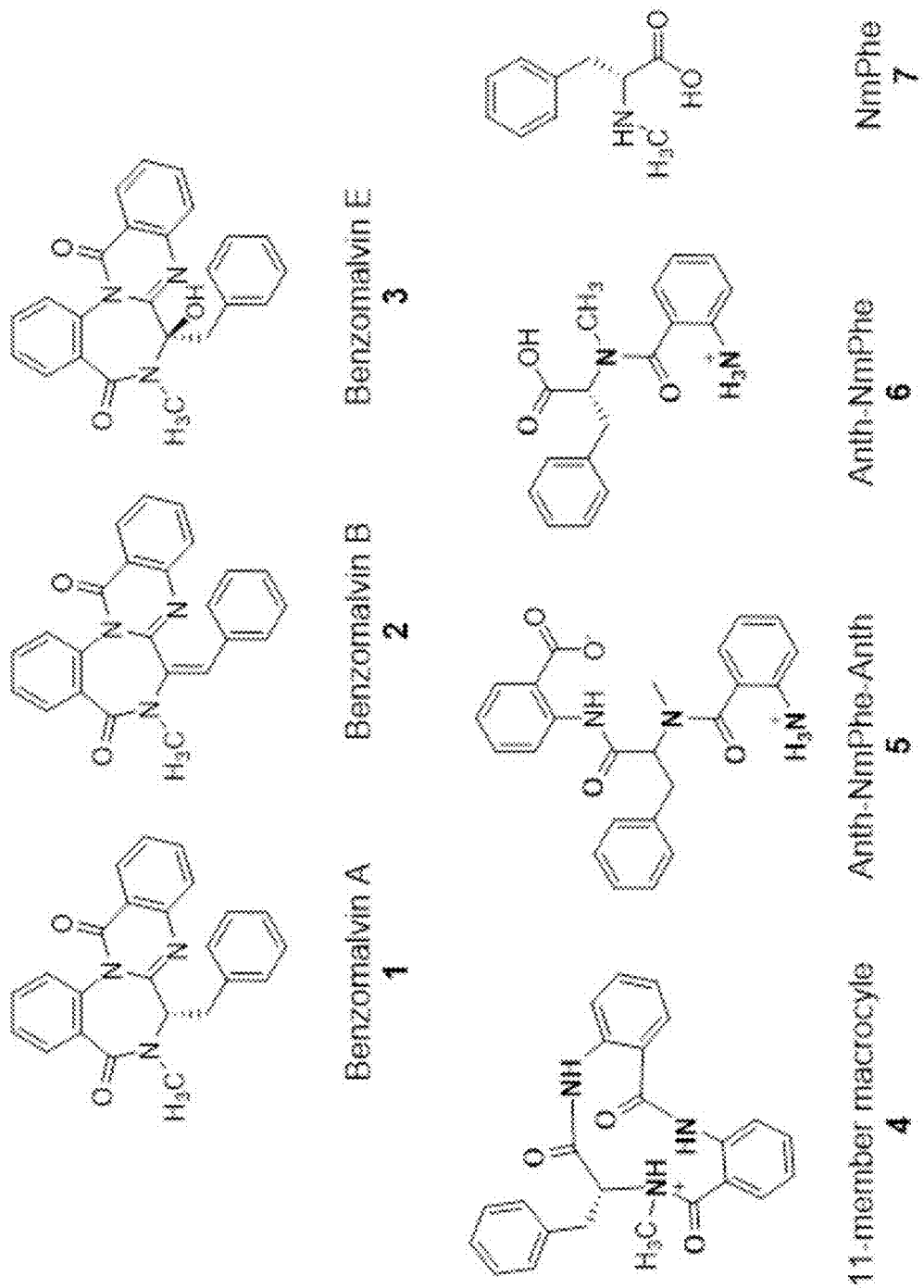
FIG. 9A-B. The Benzomalvin family of benzodiazepenes and related molecules. Variations from Benzomalvin A/D are shown in blue. Benzomalvin A is in equilibrium with atropisomer Benzomalvin D, shown in FIG. 7. Compounds 4-7 are observed biosynthetic intermediates of benzomalvin, while compounds 8-12 are intermediates which were tested for, but were not detected.
Figure 9B:
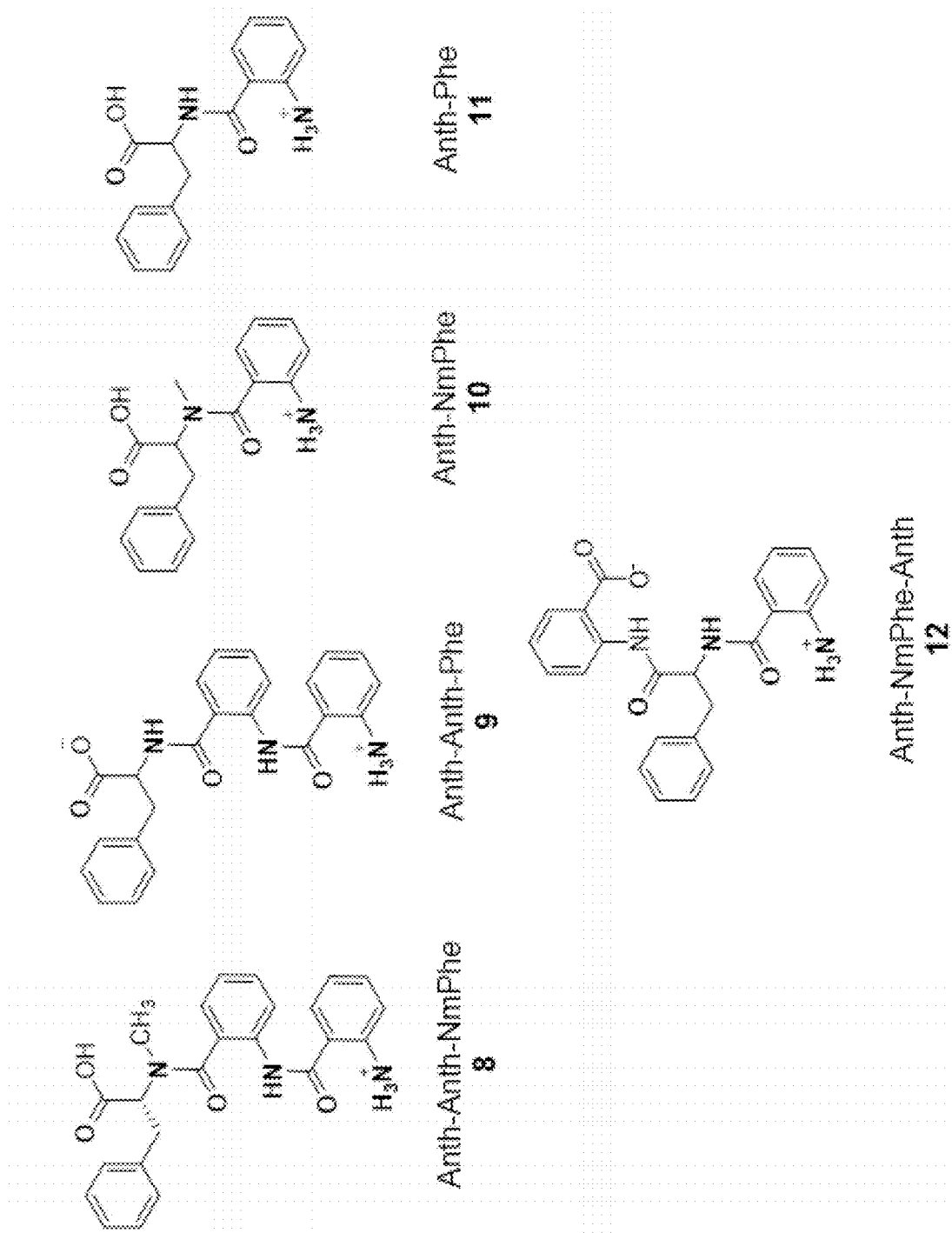

To characterize the biosynthesis of benzomalvin A/D further, hypothetical biosynthetic intermediates and precursors of benzomalvin A/D were synthesized and compared to observed ions with the same m/z values in extracts from AtFAC9J20 by LC-MS/MS (FIG. 9). This confirmed the presence of the dipeptide Anth-NmPhe and tripeptide Anth-NmPhe-Anth, as well as the free amino acid NmPhe in extracts of AtFAC9J20. FIG. 3a shows the levels of these precursors, along with the levels of the predicted 11-member macrocyclic intermediate, benzomalvin A/D, benzomalvin E, and benzomalvin B in six different deletants. In general, each predicted intermediate was found to decrease in parallel with benzomalvin A/D, consistent with their expected positions in the biosynthetic pathway.

Figure 3B:
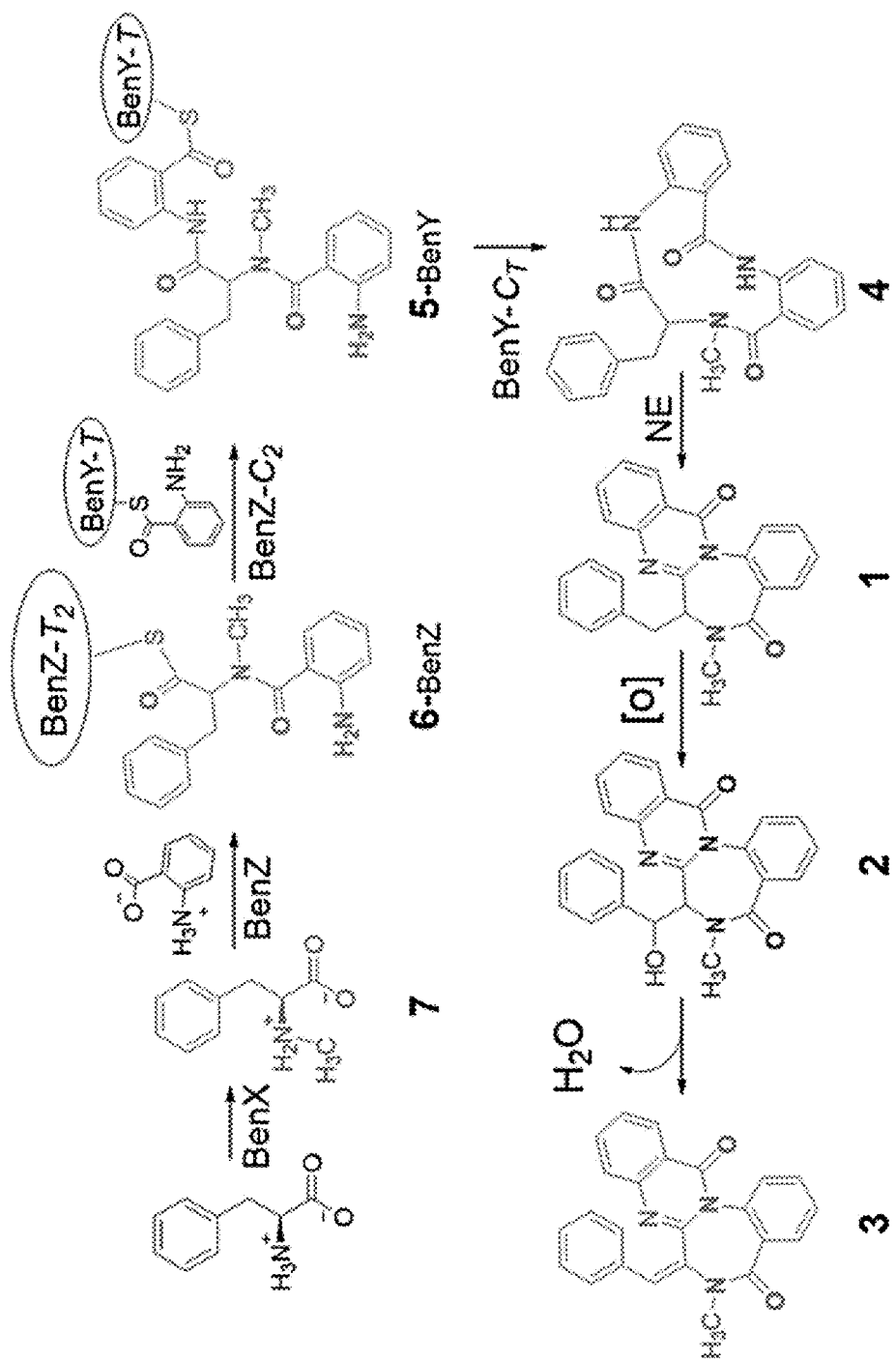

Deletant data and bioinformatic analyses were used to generate the following model of benzomalvin A/D biosynthesis (FIG. 3b). The pathway begins with the loading of amino acid precursors onto the A domains of BenY and BenZ. BenY and the A1 domain of BenZ are loaded with Anth, while the A2 domain of BenZ is loaded with NmPhe. NmPhe is likely generated through conversion of free Phe to NmPhe by the stand alone predicted SAM binding methyltransferase enzyme, BenX. Alternatively, it is possible that Phe is incorporated by the A2 domain of BenZ and is then methylated by BenX while attached to the T2 domain of BenZ. Given the observation of free NmPhe in solution, and the standalone nature of BenX, we propose direct incorporation of NmPhe. Condensation of Anth with the secondary amine of NmPhe is then catalyzed by the C1 domain of BenZ. This is followed by in trans condensation of the Anth-NmPhe dipeptide with Anth bound to the T domain of BenY by the C2 domain of BenZ to form the tripeptide Anth-NmPhe-Anth. Cyclization and release of the tripeptide is then catalyzed by the CT domain of BenY and the resulting 11-member macrocyclic intermediate is likely to spontaneously collapse to form the benzodiazepine core, as previously reported for the anthranilate containing tripeptide secondary metabolite, asperlicin (ref).

No genes were identified for specific oxidation of benzo-malvin A/D to benzomalvin E or dehydration of benzomalvin E to benzomalvin B in AtFAC9J20. The relative abundance of these products differed significantly between $A.$ $terreus$ and AtFAC9J20 extracts, and benzomalvin E was by far the most abundant form in $A.$ $terreus$ ATCC 20524 (FIG. 8). This indicated that ordinarily an $A.$ $terreus$ enzyme acts in trans to synthesize benzomalvin E and in the absence of this enzyme, which is not found in AtFAC9J20, a P450 monooxygenase enzyme from the heterologous host is able to act on benzomalvin A/D to produce benzomalvin E. This is followed by spontaneous elimination of water to form benzomalvin B. Given the low abundance of benzomalvin B in $A.$ $terreus$, it seems likely that $A.$ $terreus$ does not possess an enzyme dedicated to this final transformation.

AtFAC9J20—Cluster #2: Analysis of Ophiobolin-Like Product (FAC Score of 5.6)

Figure 12A:
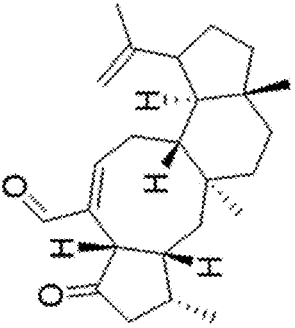
FIGS. 12A-B. Structures of ophiobolin-like compounds. A) Potential structures of unknown compound with m/z=369.2776. Identical substructure is shown in blue. B) Ophiobolin H, which is identified by exact mass, clusters with the ophiobolin-like compound.
Figure 12A:
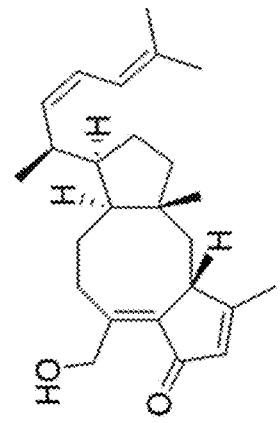
Figure 12A:
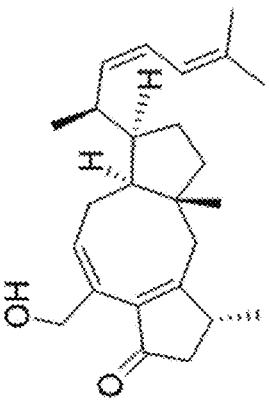
Figure 12A:
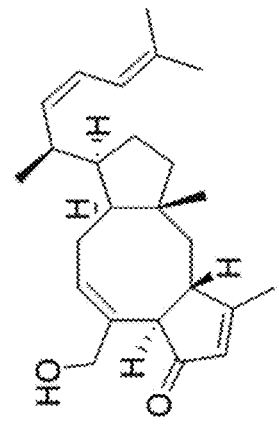
Figure 12A:
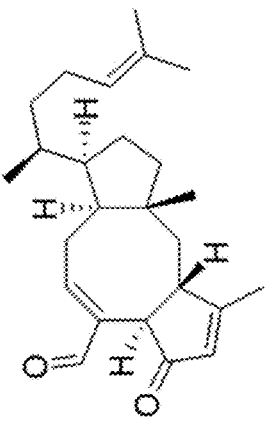
Figure 12B:
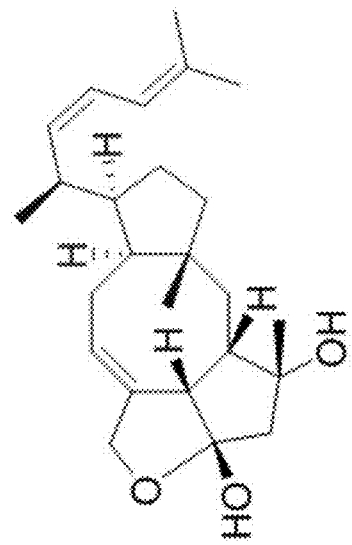
Figure 13A:
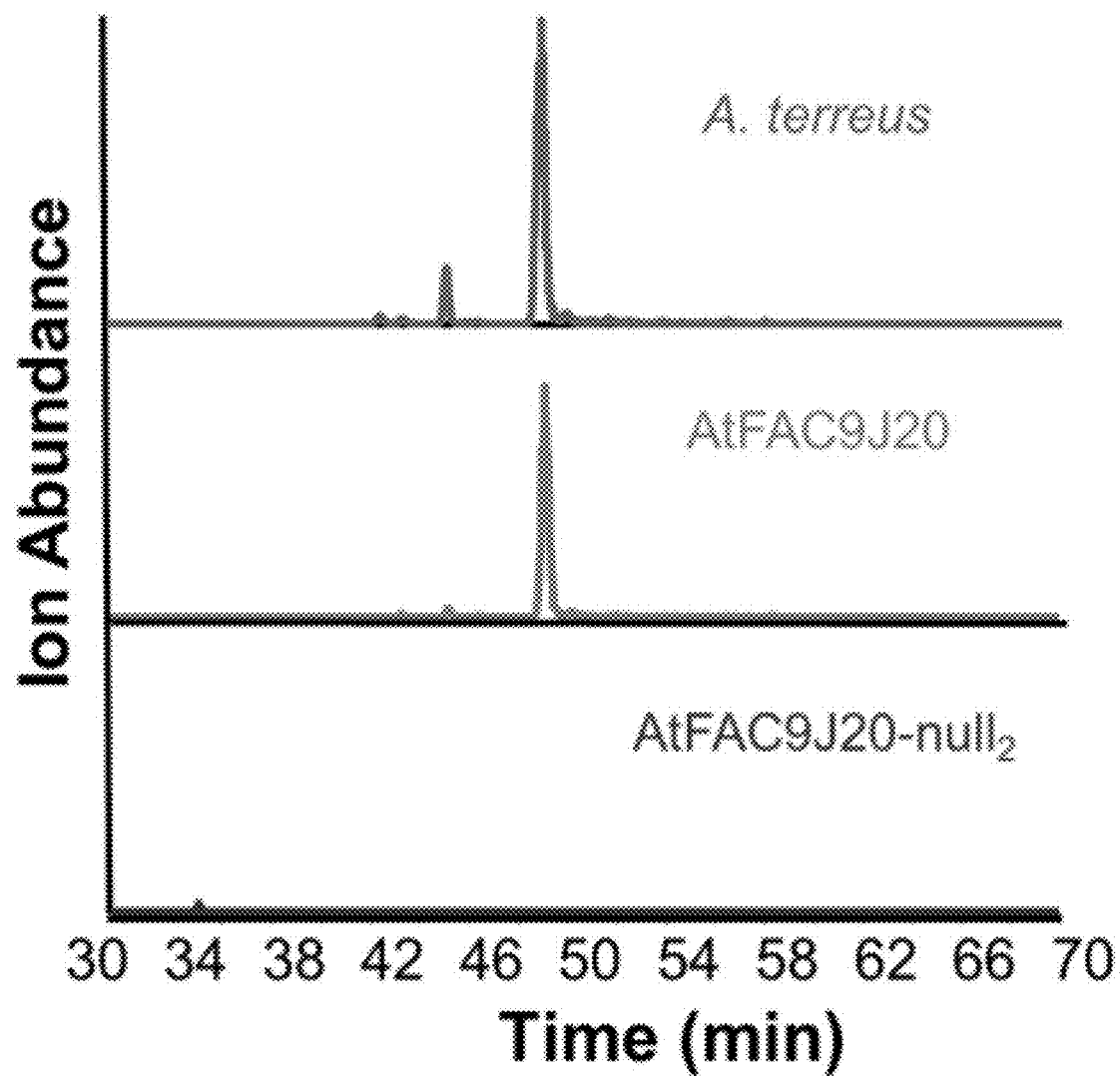
FIGS. 13A-C. Identification of ophiobolin-like terpendoid product. A) The ion with m/z=369.2783 is present in extracts of A. terreus, AtFAC9J20, but not in the null2 deletant. B) The simulated formula C25H37O2 matches the observed MS1 spectrum within 4 ppm. C) Nodes are labeled with m/z values for ions. Ions shown are related by MS2 cosine similarity clustering. An ion with m/z=387.290 dereplicates to ophiobolin H by exact mass and is related to the unknown ophiobolin-like compound.
Figure 13B:
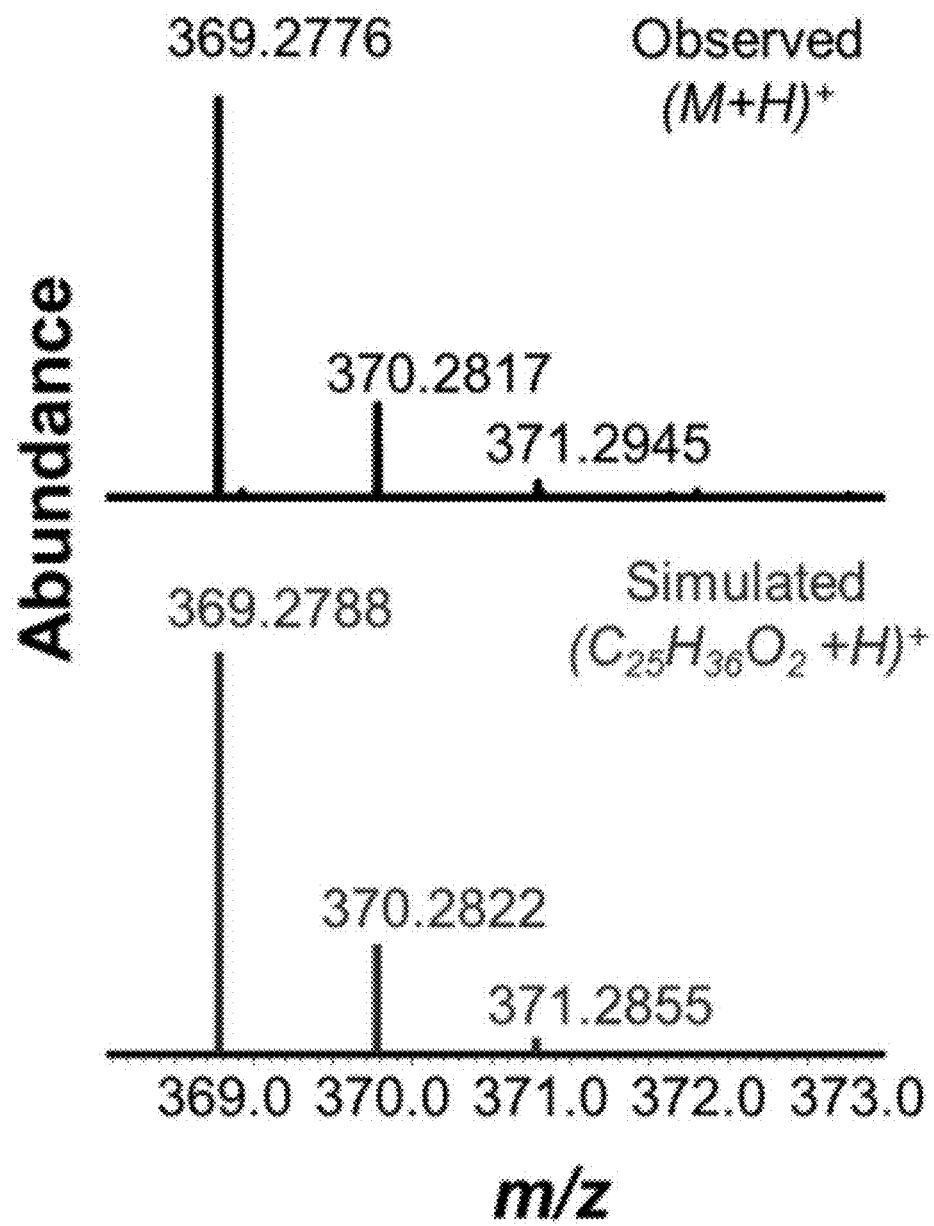
Figure 13C:
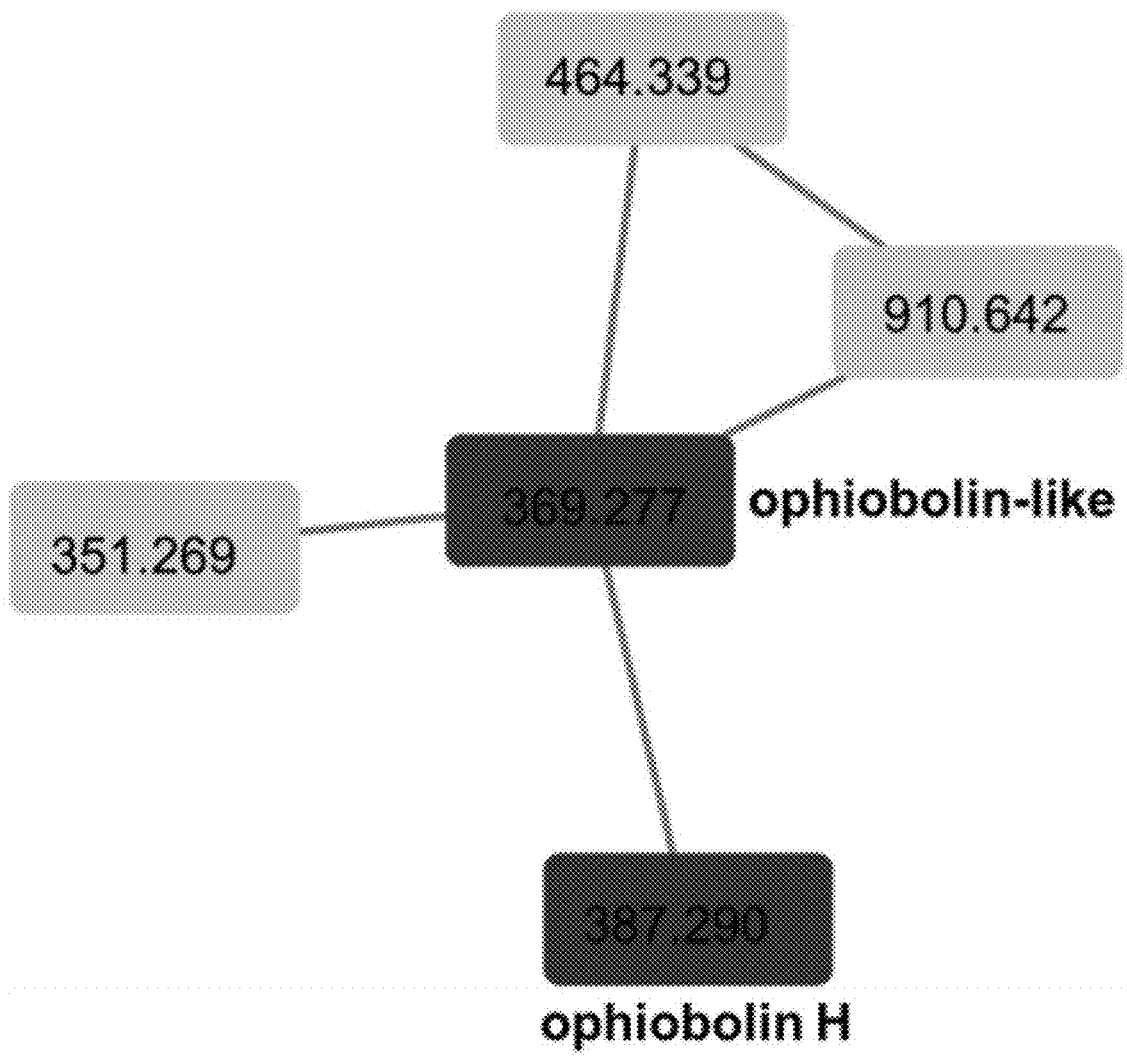
Figure 14:
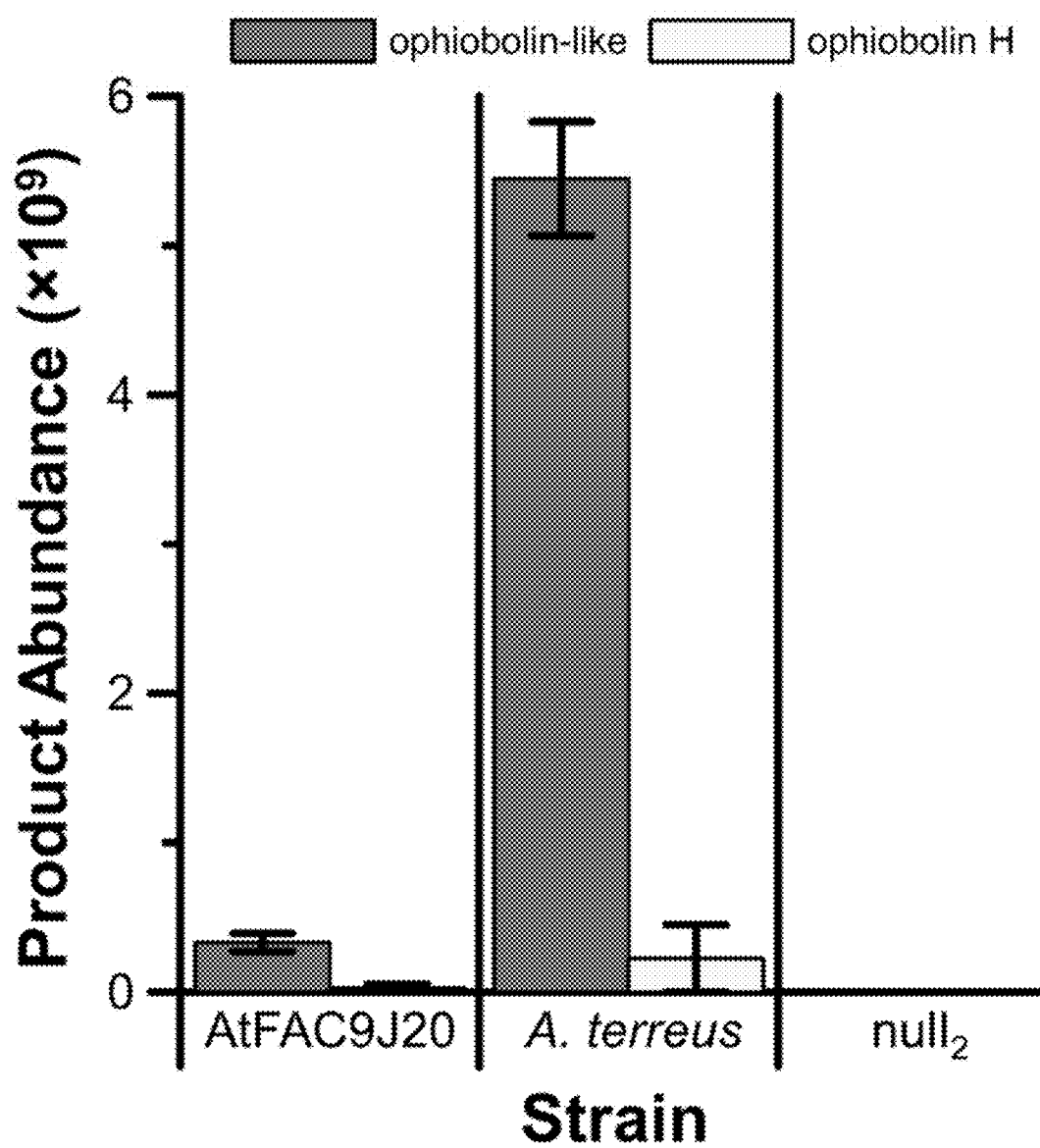
FIG. 14. Amount of ophiobolin-like and ophiobolin H products produced by AtFAC9J20, A. terreus ATCC 20524, and AtFAC9J20-null2.

AtFAC9J20 produced an unusually large number of high scoring features, raising the prospect that a single FAC might be able to express multiple intact BGCs, increasing the flexibility of FAC-MS. Analysis of the top scoring compounds, after eliminating those which were associated with benzomalvin A/D based on retention time profiles and fragmentation patterns, led to identification of a compound with FAC-score=5.6. The ion feature had a molecular cation with m/z=369.2783 and a molecular formula of $C_{25}H_{36}O_2$ (observed: 368.2710 Da, theoretical: 368.2715 Da) (FIG. 13). This formula has been reported for four closely related members of the ophiobolin family of sesterpenoid natural products from $A.$ $ustus$, as well as the structurally similar sesterpenoid variecolin from $A.$ $variecolor$ (FIG. 12a) (ref). To determine if other molecules related to the ophiobolin-like compound were observed in FACAt9J20, MS2 data from the FAC was subjected to cosine similarity clustering to identify closely related compounds. This lead to identification of a related molecule which dereplicated as ophiobolin H by accurate mass, m/z=387.2894 and molecular formula of $C_{25}H_{38}O_3$ (observed: 386.2821 Da, theoretical: 386.2821) (FIG. 13b). Finally, a BLAST search of proteins in Swiss-Prot against the sequence of the predicted terpene synthase gene from FACat9J20 revealed the closest related annotated protein was Ophiobolin Synthase F from $A.$ $clavatus$ (33% amino acid identity, E-value=2×10-103). The predicted terpene synthase was then deleted in AtFAC9J20Δterp (FIG. 4b), eliminating the ophiobolin-like compound. The gene was also deleted in null2, with resultant loss of the compound (FIG. 4a-b). Together these observations demonstrate that FACAt9J20 encodes a member of the ophiobolin family of compounds, independent of the benzomalvin A/D BGC.

AtFAC9J20—Cluster #3: Analysis of Hybrid PKS-NRPS Lipopeptide Using benY Deletant (FAC Score of 23.6)

Figure 15:
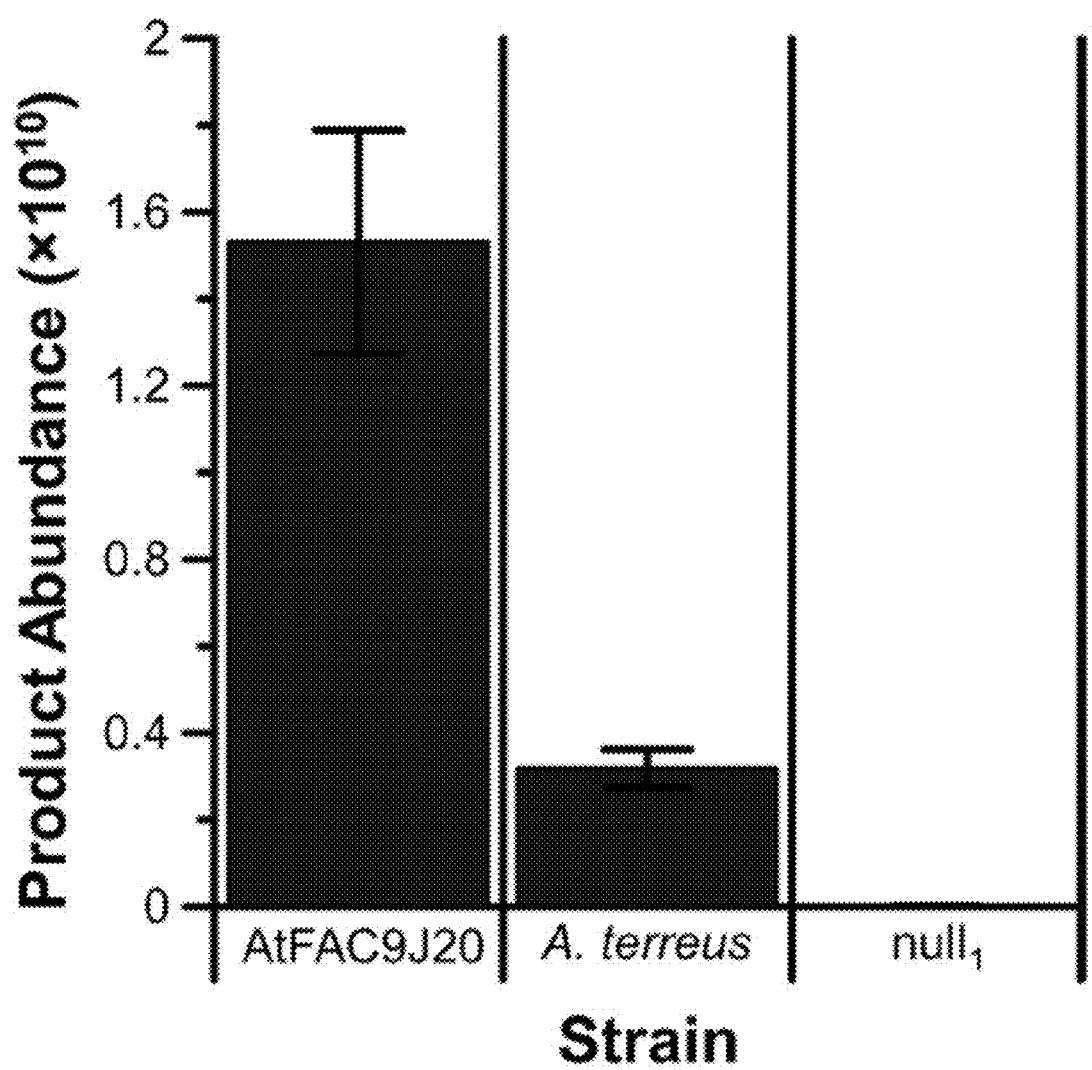
FIG. 15. Amount of lipopeptide product produced by AtFAC9J20, A. terreus parent strain, and AtFAC9J20-null1.
Figure 16A:
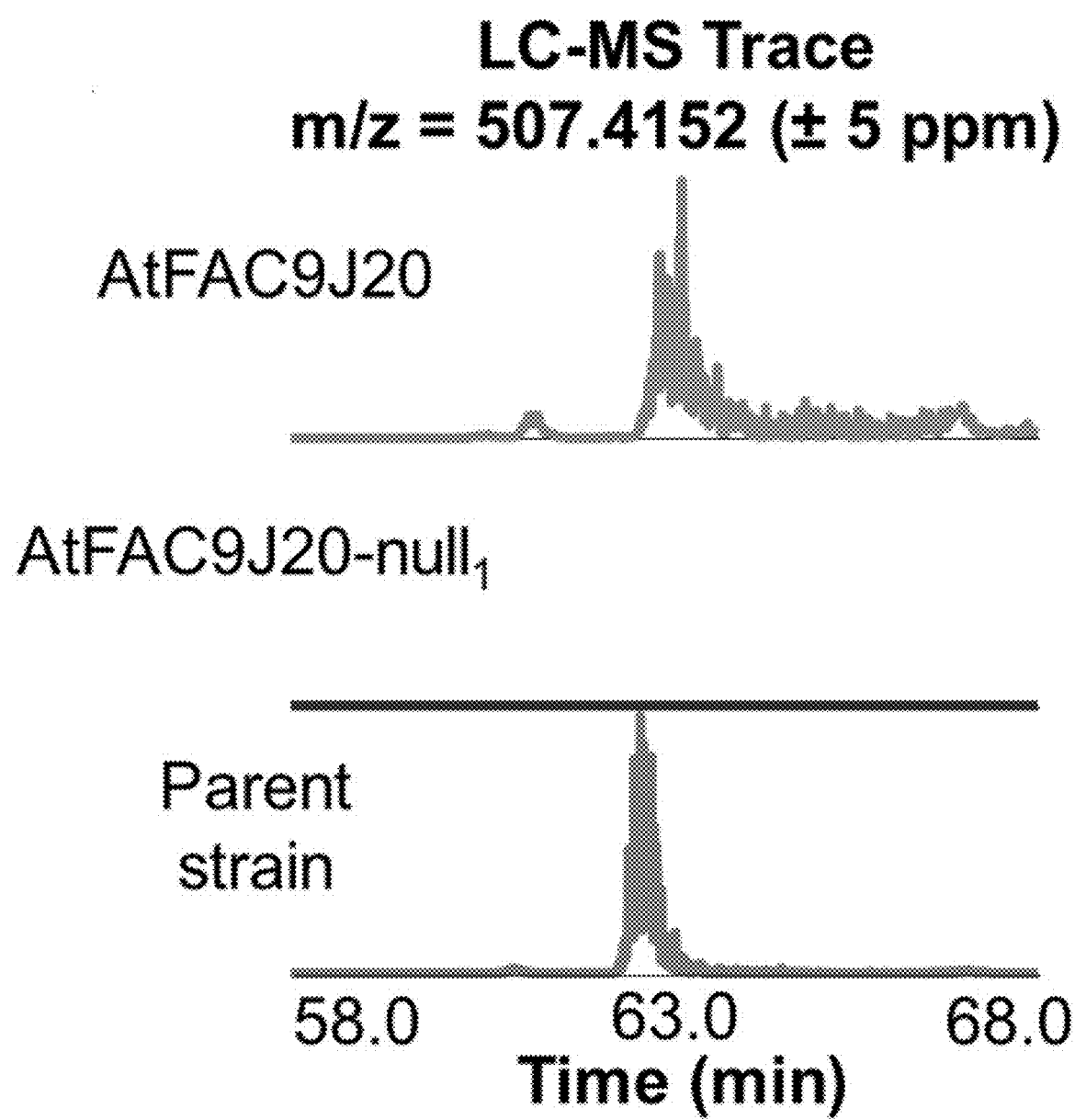
FIGS. 16A-B. Lipopeptide produced by AtFAC9J20. A) Ion with m/z=507.4152 was detected in extracts from AtFAC9J20 and A. terreus parent strain, but not AtFAC9J20-null1 in which half of the insert is deleted. B) The MS 2 spectrum reveals immonium ions consistent with Val (obs. m/z=72.0815) and either Ile or Leu residues (obs. m/z=86.0972). Also an ion characteristic of a dipeptide of Ile and/or Leu was observed (obs. m/z=185.165).
Figure 16B:
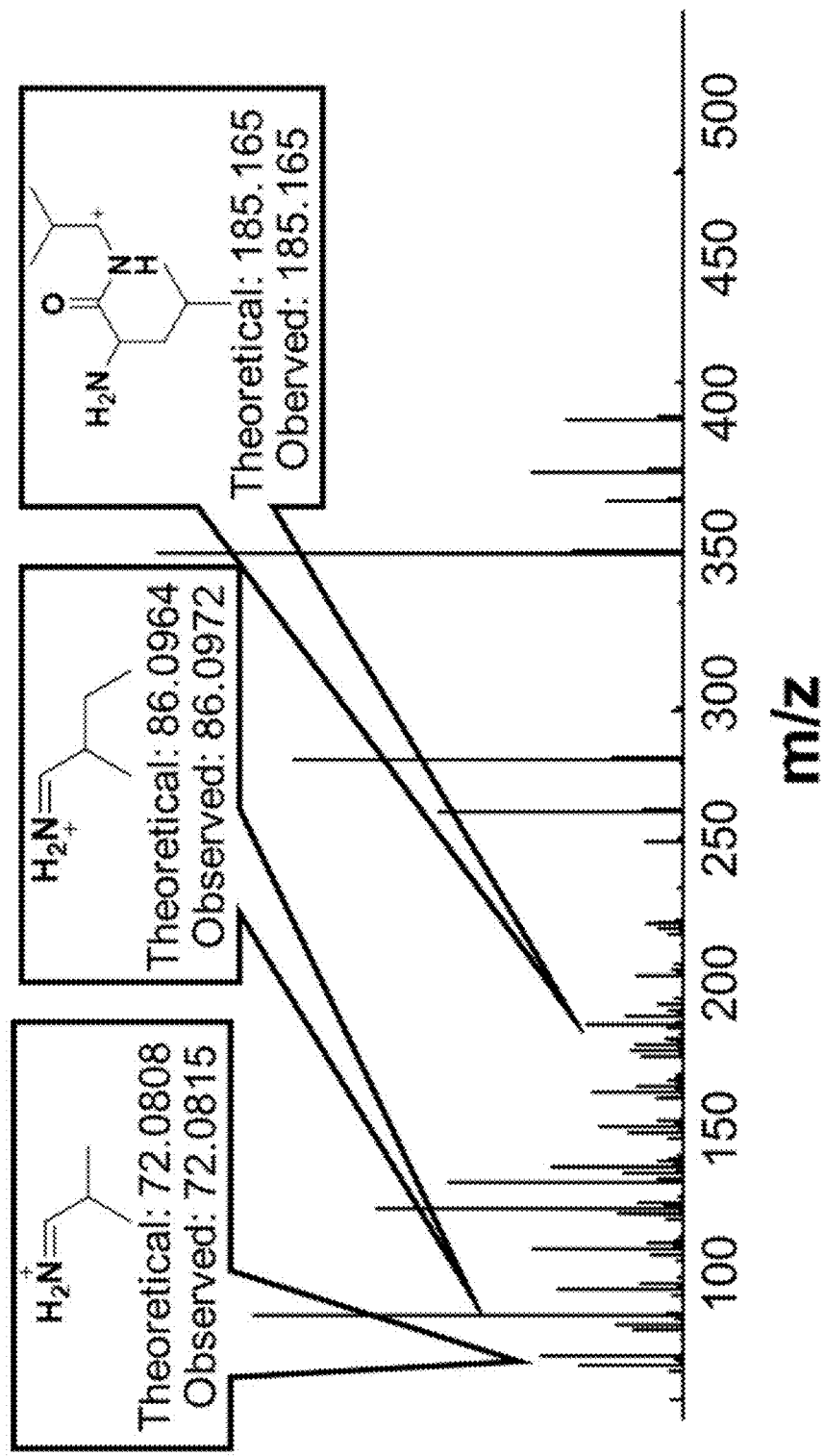
Figure 17A:
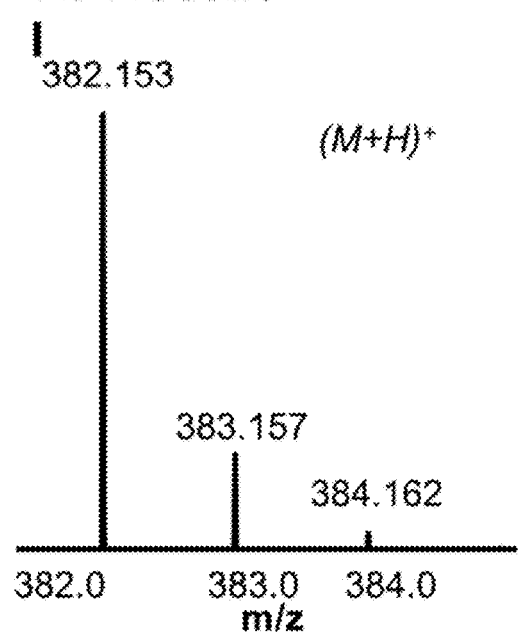
FIG. 17A-I. FACs expressing unique small molecule products. (i) MS1 of heterologous FAC product and (ii) Overlain selected ion chromatograms the corresponding ion from the FAC, the negative control, and the parent strain used to generate the FAC insert.
Figure 17A:
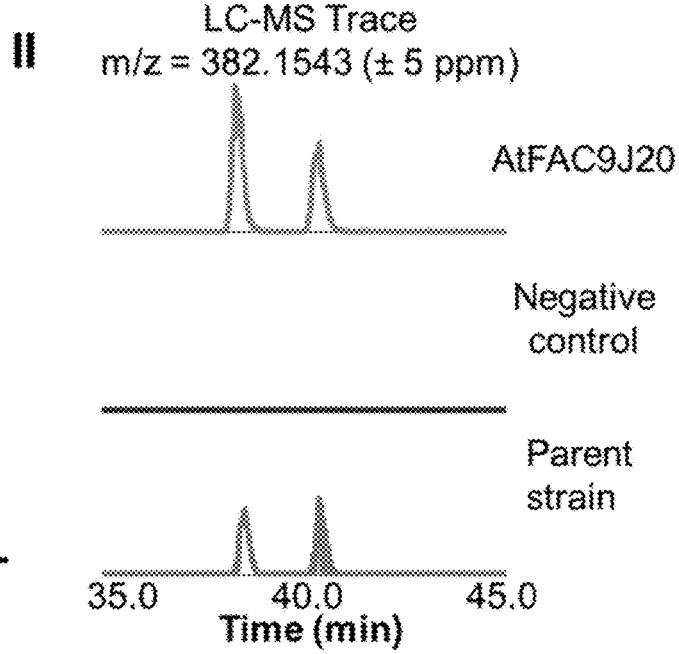
Figure 17A:
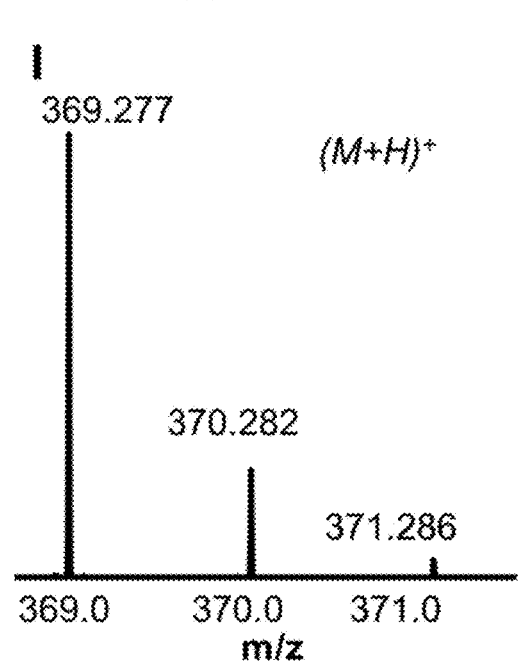
Figure 17A:
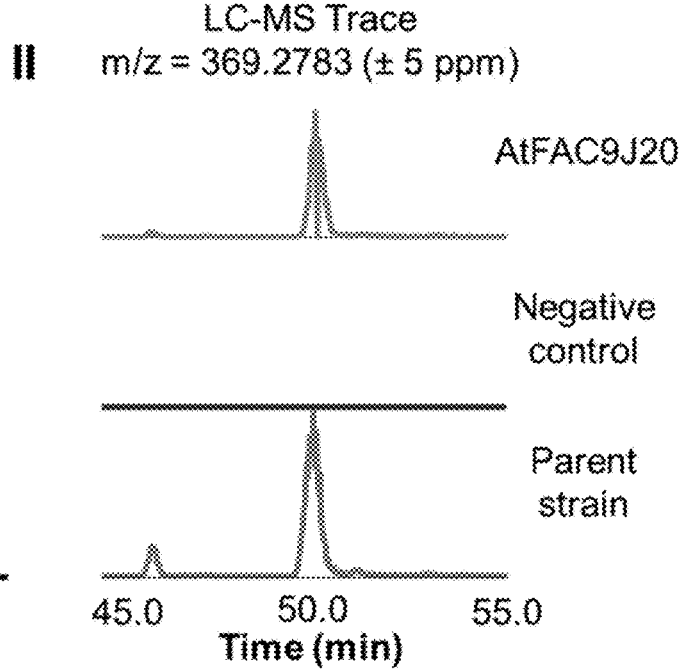
Figure 17B:
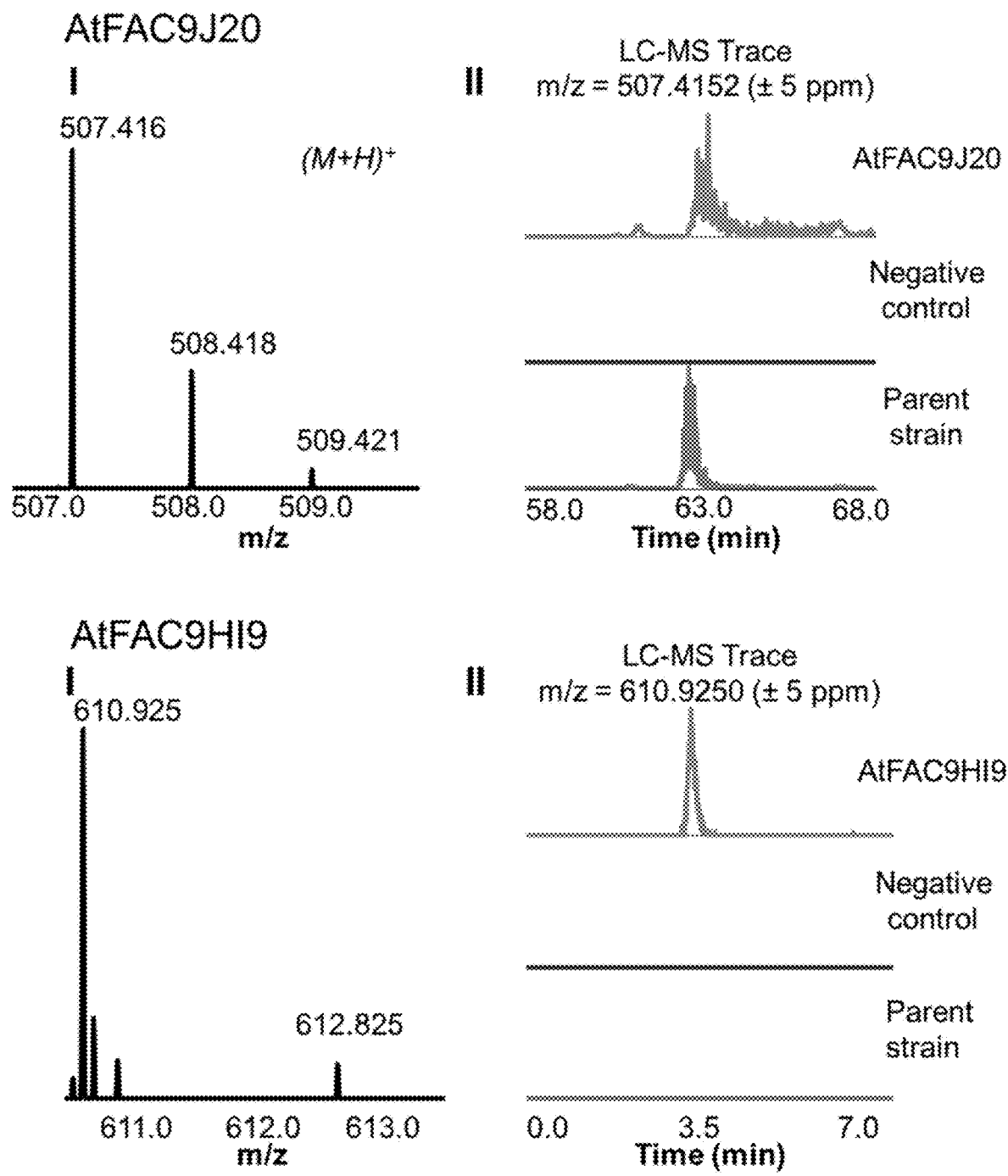
Figure 17C:
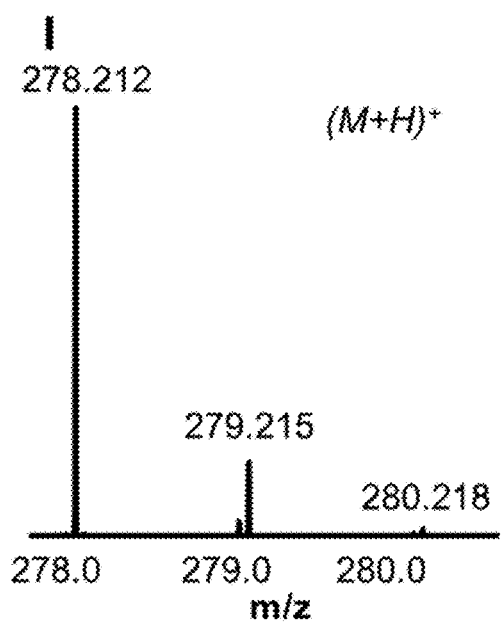
Figure 17C:
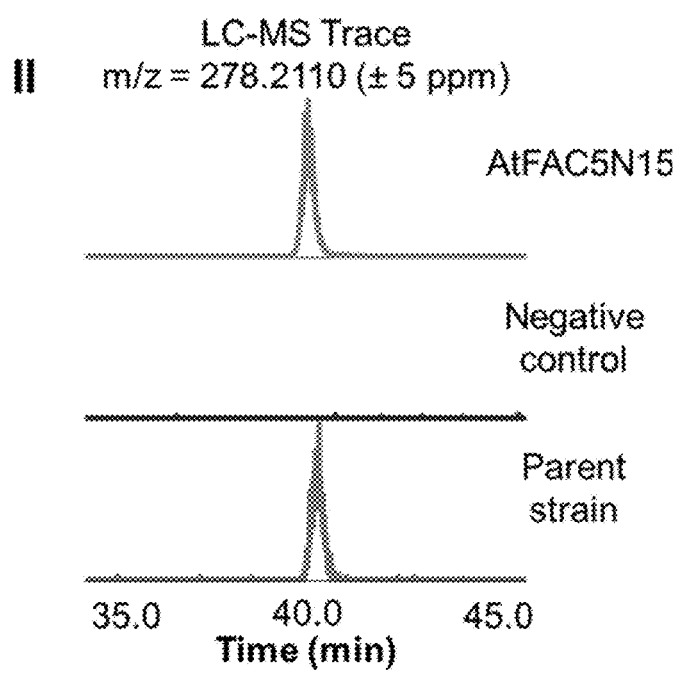
Figure 17C:
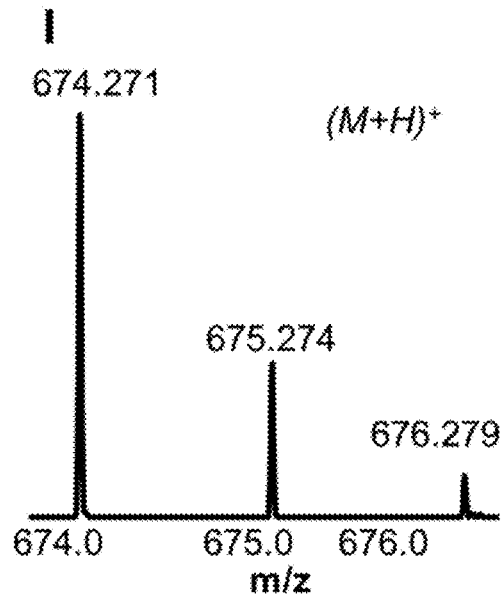
Figure 17C:
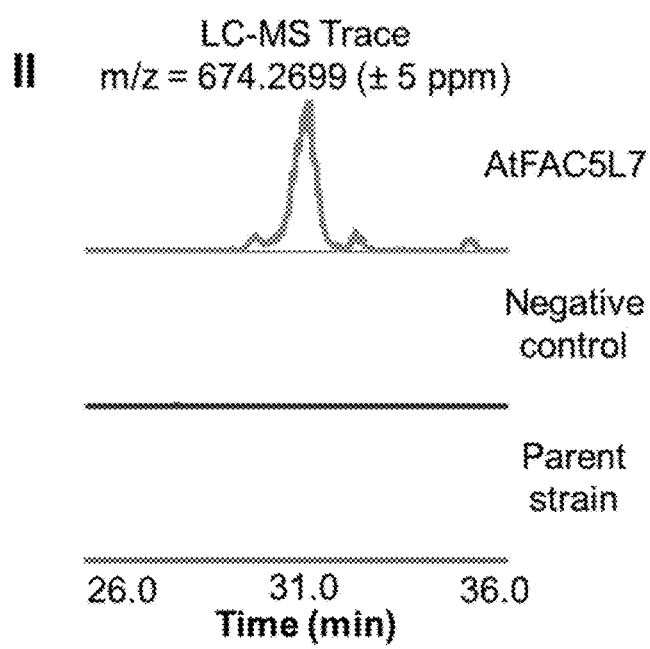
Figure 17D:
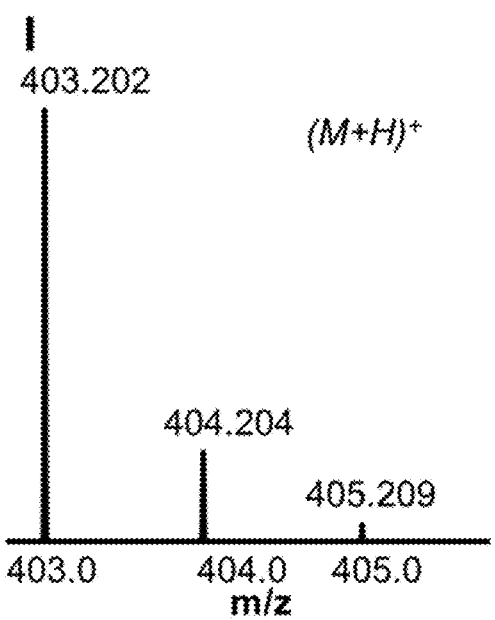
Figure 17D:
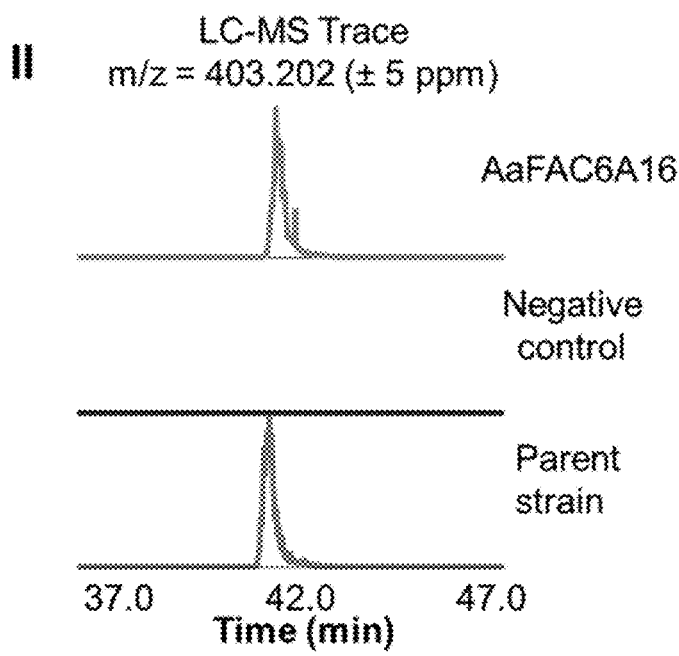
Figure 17D:
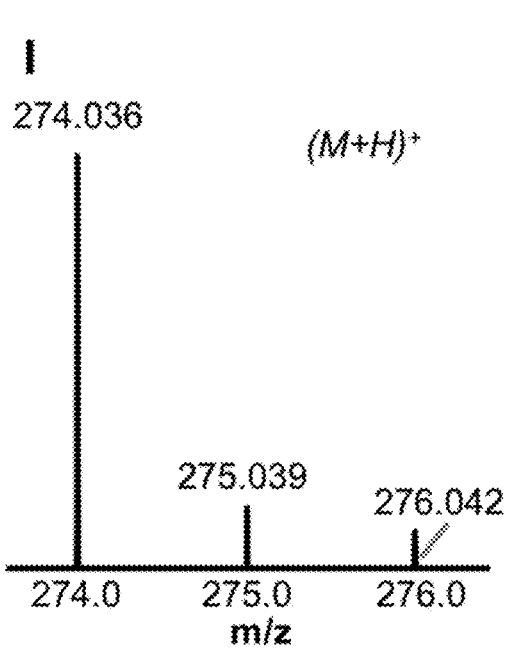
Figure 17D:
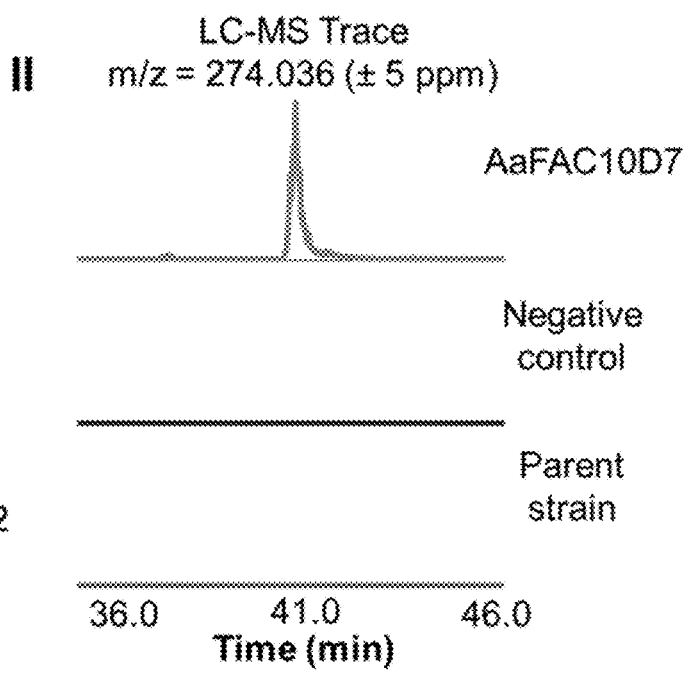
Figure 17E:
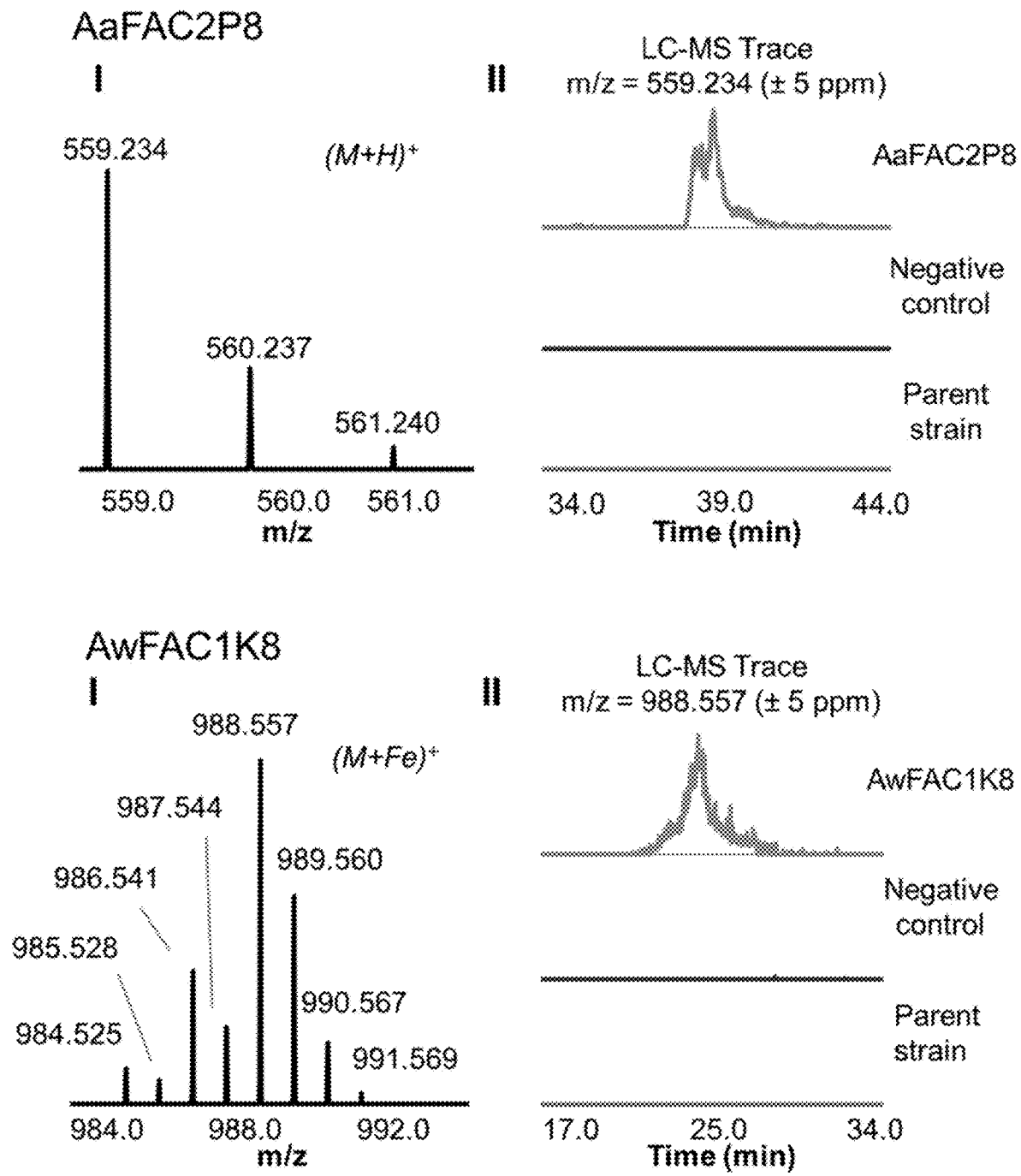
Figure 17F:
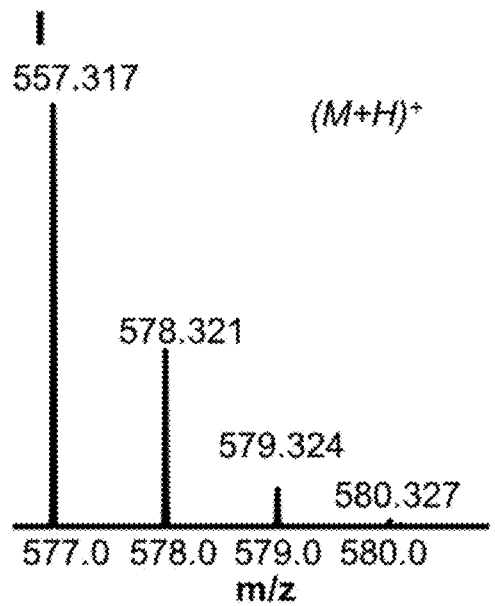
Figure 17F:
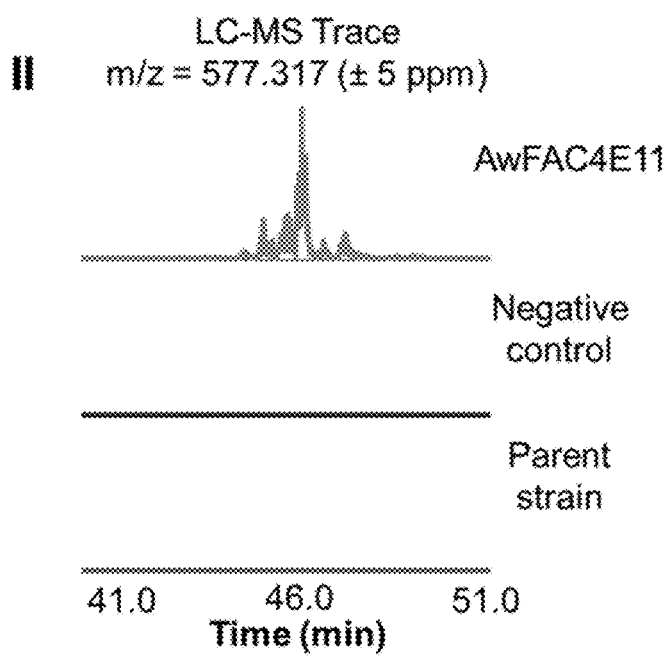
Figure 17F:
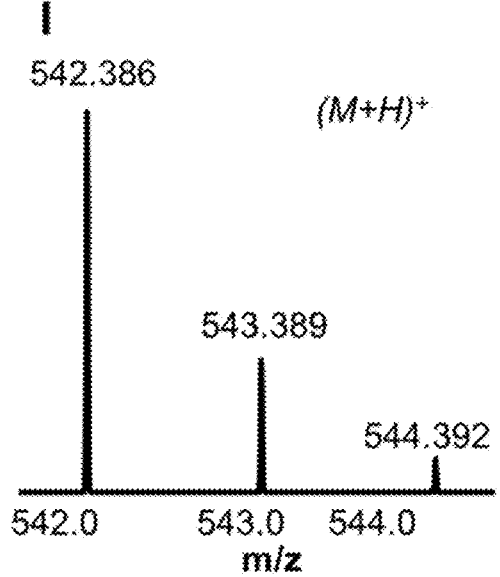
Figure 17F:
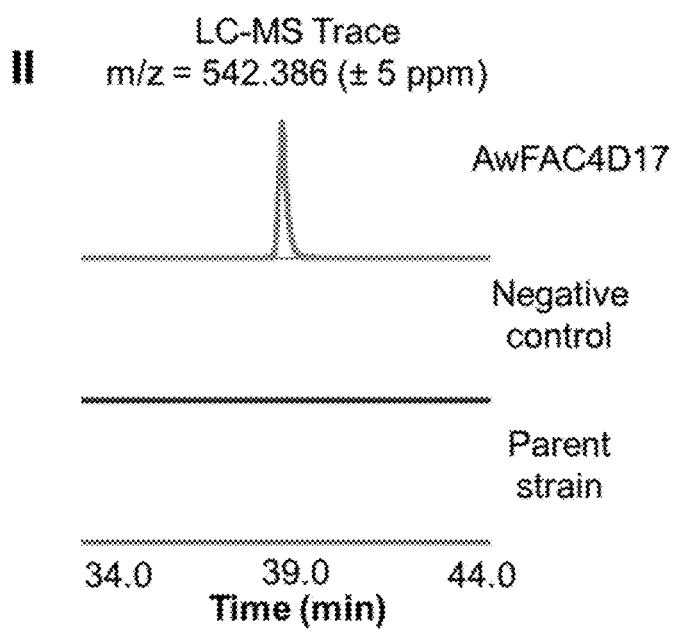
Figure 17G:
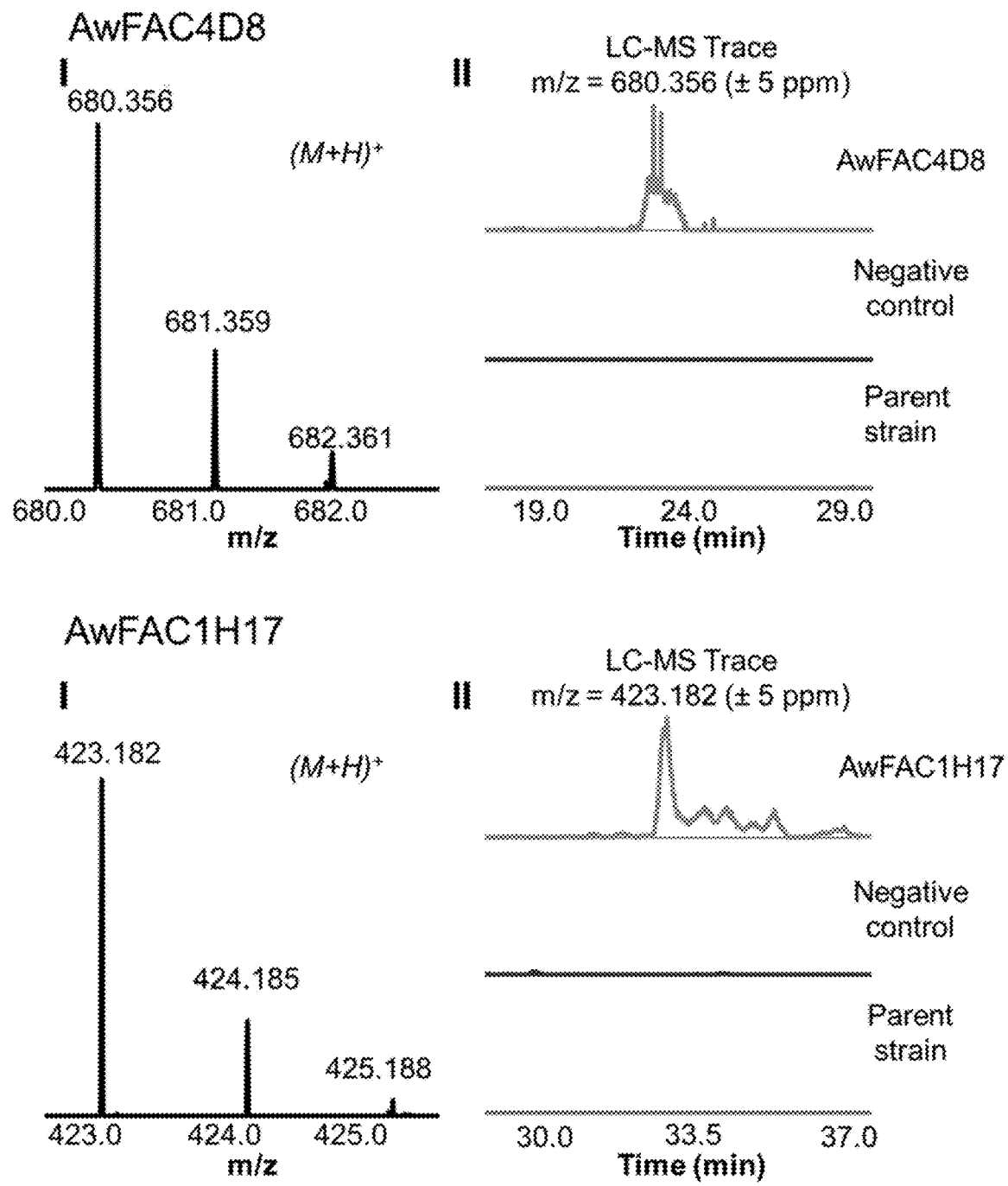
Figure 17H:
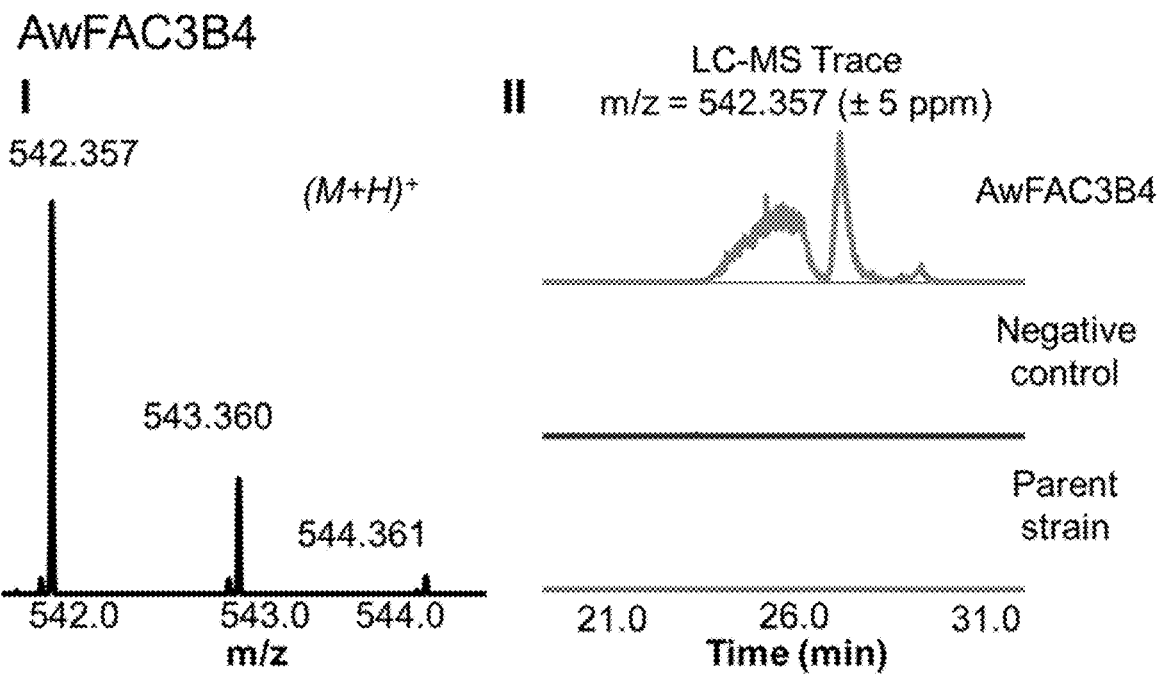
Figure 17H:
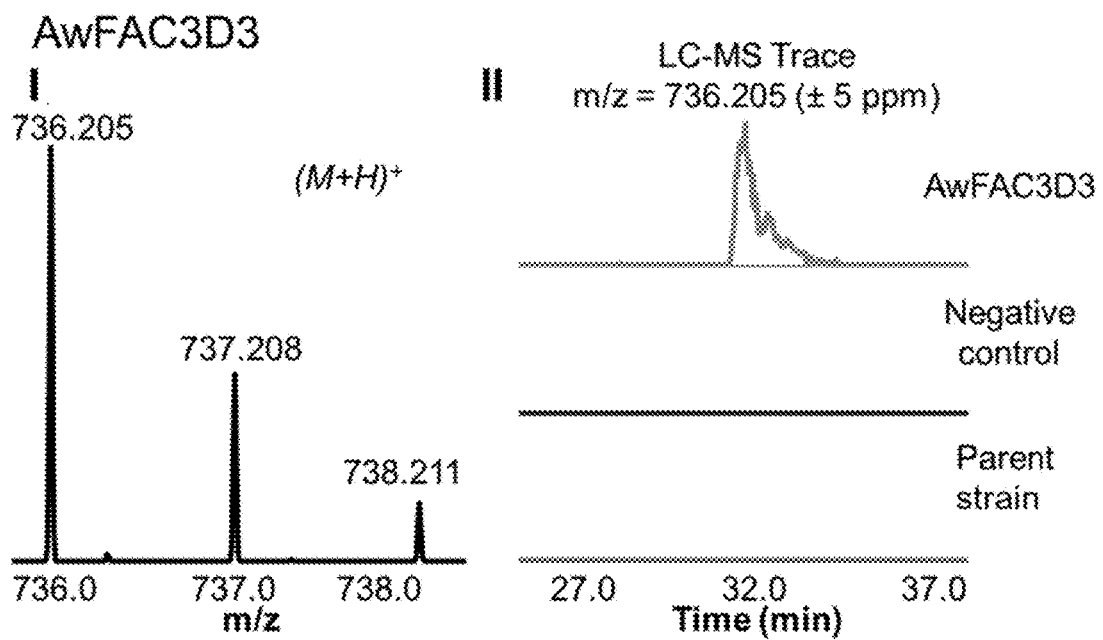
Figure 17I:
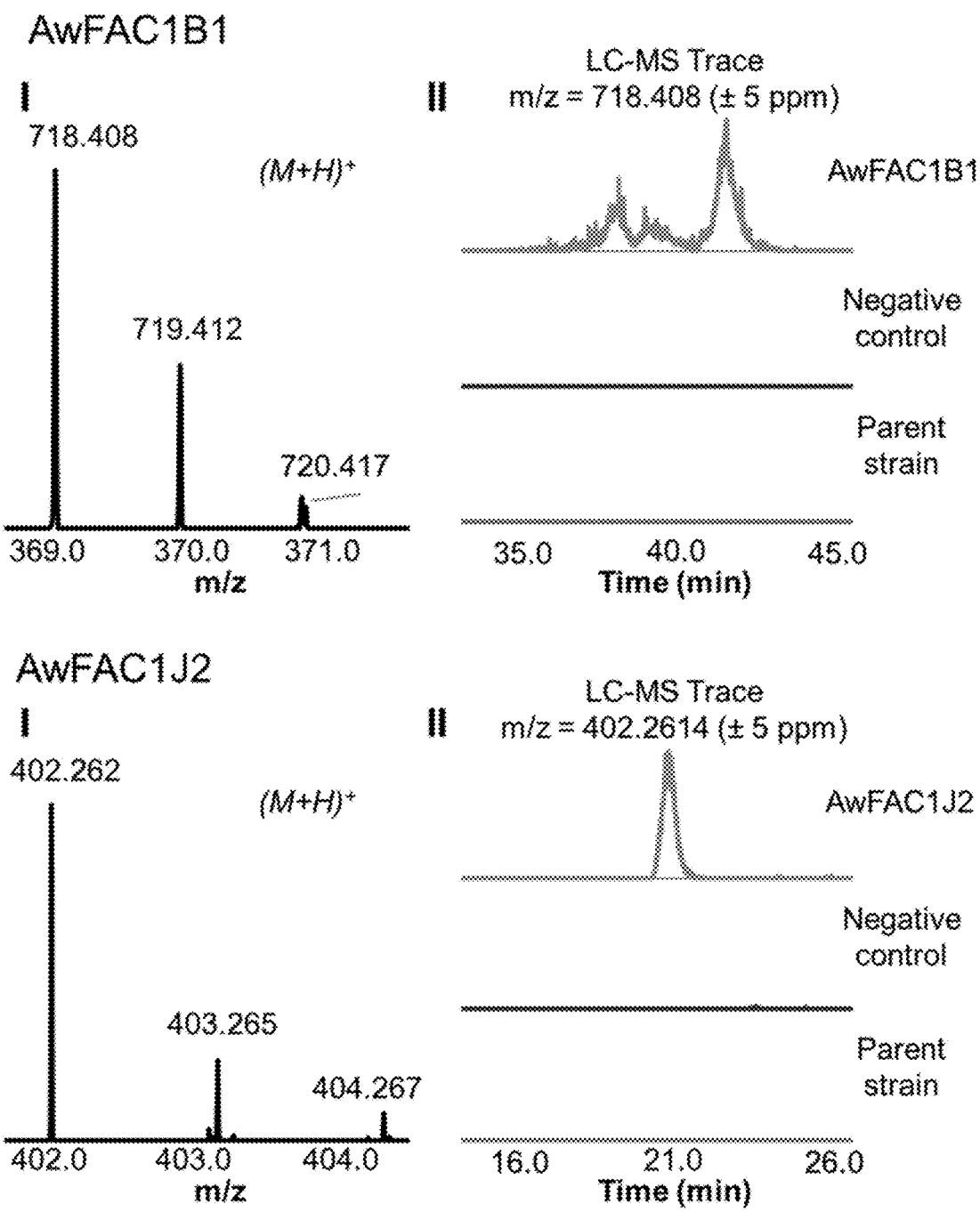

To determine if either the PKS or NRPS proteins adjacent to the benzomalvin BGC were able to produce a product, AtFAC9J20ΔbenY was subjected to the FAC scoring pipeline. Strikingly, the top ion received a score of 23.6, with an m/z of 507.4152 and a predicted molecular formula of $C_{30}H_{54}N_2O_4$ (observed: 506.4079 Da, expected: 506.4084 Da) (FIG. 16). The ion was also present in extracts from $A.$ $terreus$ strain NIH2624 (FIG. 15). Deletion of either the NRPS or PKS protein eliminated this compound (FIG. 4).

Analysis of MS2 data revealed immonium ions and neutral losses matching Val and Ile/Leu, consistent with the prediction that the two A domains would incorporate branched aliphatic amino acids based on their extracted A domain signatures (Table 4, FIG. 16). A BLAST search of the PKS enzyme revealed that its closest annotated match was the $A.$ $terreus$ lovastatin diketide synthase, LovF, which produces α-methyl butyrate (31% amino acid identity and E-value=0.0).

Example 2

MS2 Analysis and Scoring

In some embodiments, FAC scoring based on MS1 and/or HPLC-MS relies on the intact mass of the metabolite and/or its HPLC retention time. However, drift of HPLC retention times over time and mass/charge-overlap of metabolites may complicate MS1 identification of large metabolites and/or the use of such methods for large data sets. In some embodiments, the use of MS2 structural data (e.g., MS analysis before and after metabolite fragmentation) provides improved FAC scoring, allows for analysis of much larger datasets, and provides for distinction between large/similar metabolites.

Figure 18:
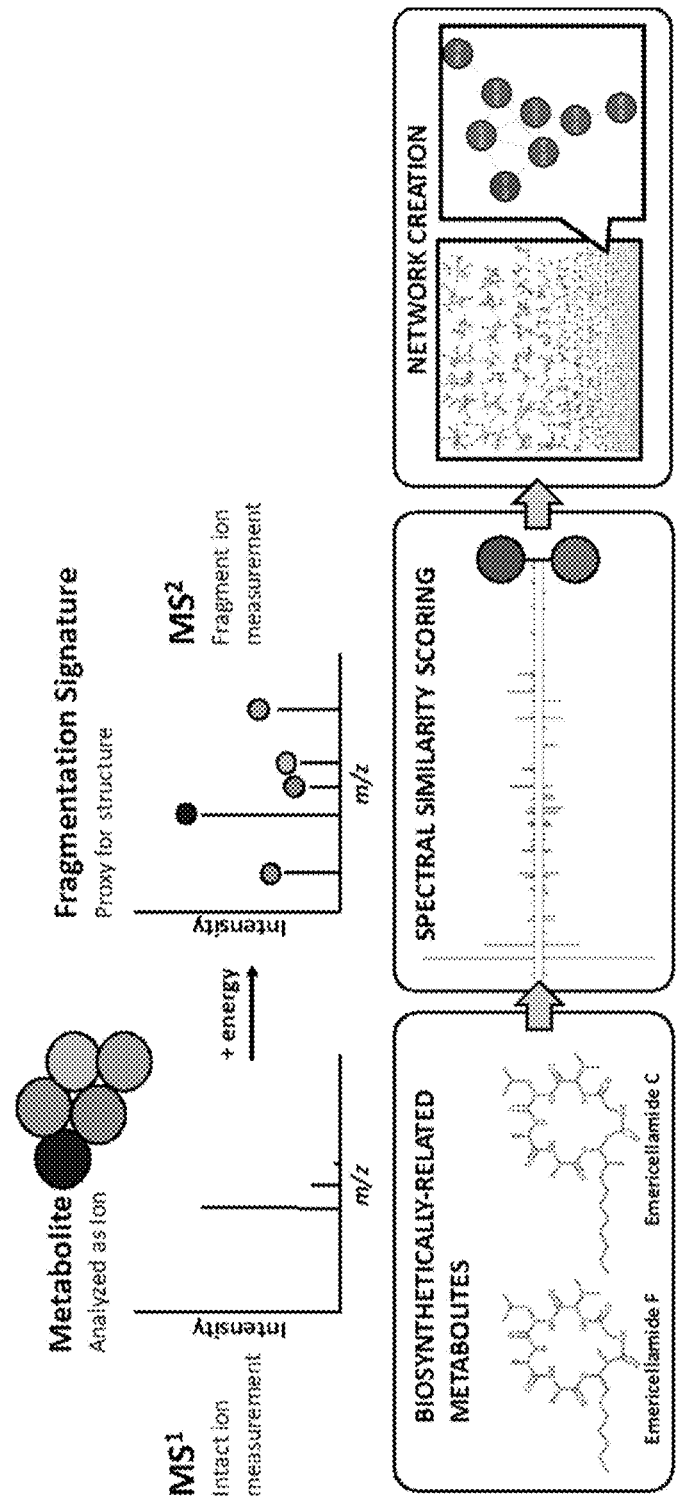
FIG. 18. Schematic depicting an exemplary procedure for MS2 screening and data analysis.
Figure 19:
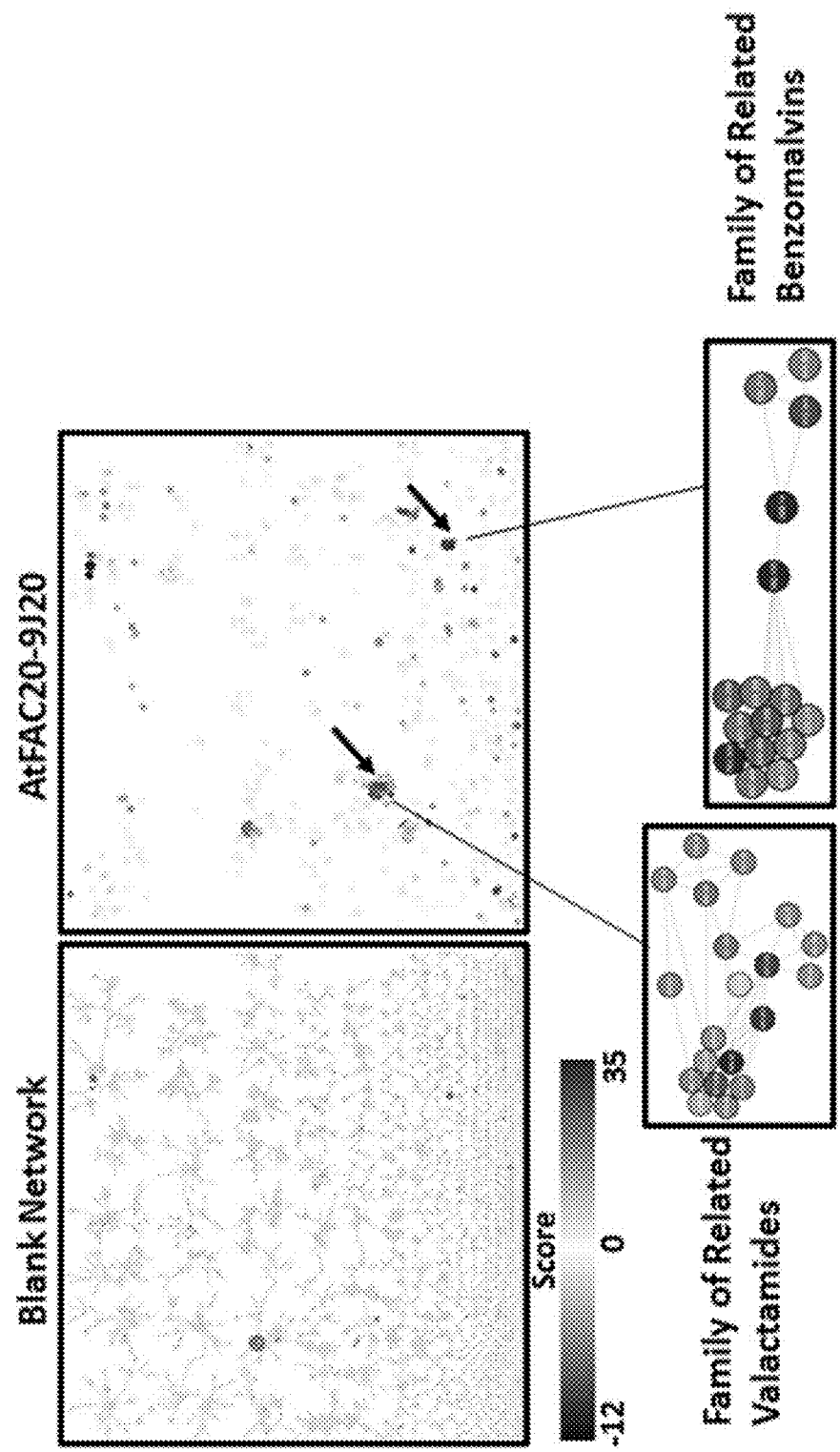
FIG. 19. Exemplary FAC scoring network for the AtFAC9J20 fungal construct.

An exemplary MS2 analysis (See, e.g., FIG. 18) involves first measurement of the intact mass to charge ratio of a metabolite. Once an intact mass measurement is made, an ion is isolated and collided with a gas to cause it to fragment. The way an ion fragments yields its "MS2 fingerprint." Using automated software, MS2 fingerprints are compared and organized into clusters of related metabolites that can be visualized as a network (FIG. 19). These networks have been successfully created from >1000 mass spectrometry files from multiple years of FAC-MS data collection, including every FAC expression strain analyzed during development of embodiments herein.

Figure 20:
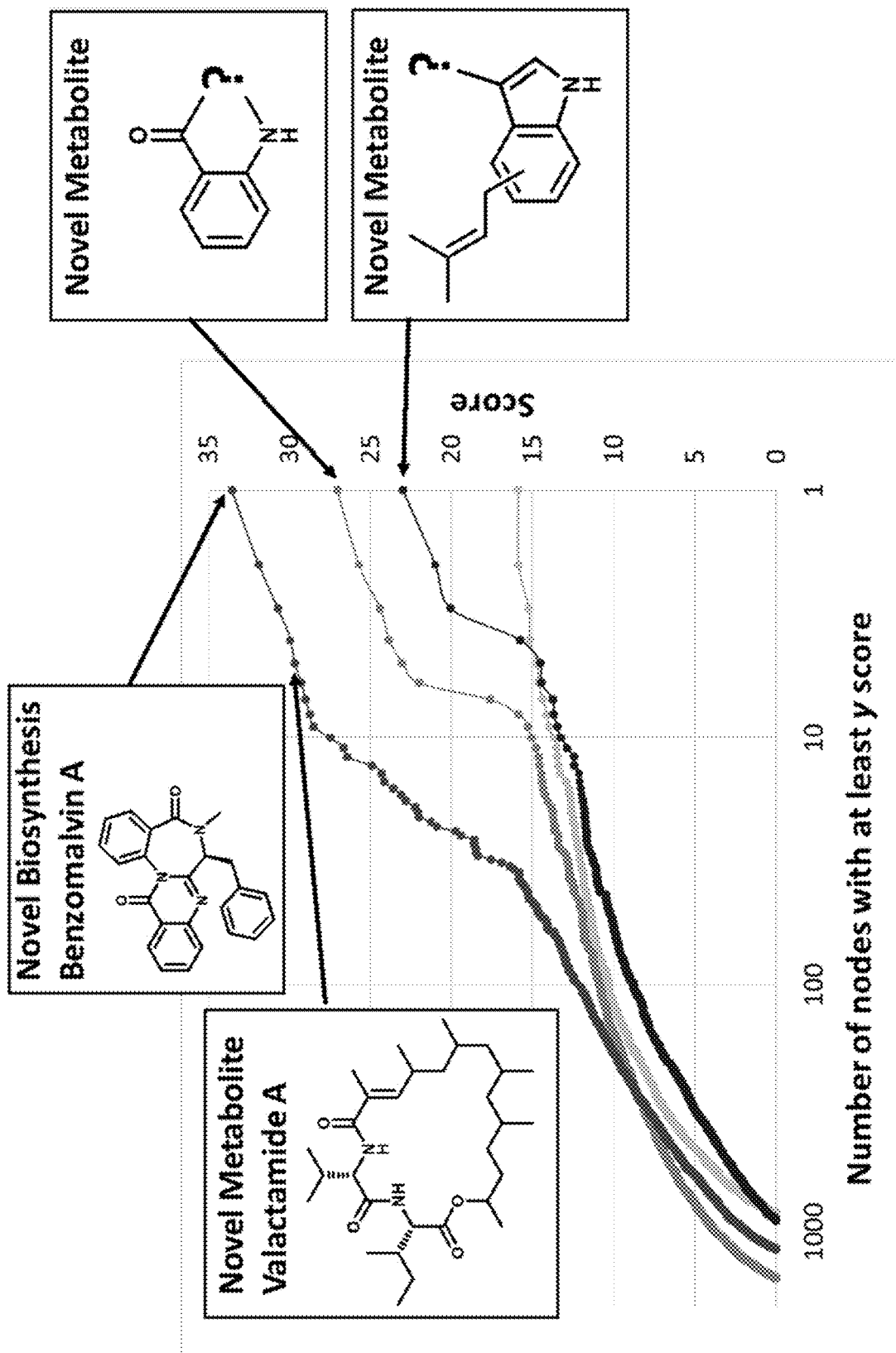
FIG. 20. Graph depicting FAC-score network analysis to identify metabolites produced by a BGC using the methods described herein.

Using an equation similar to the FAC score equation above (e.g., log [abundance]×log [ratio]−negative control), ions from each FAC are scored based on uniqueness and abundance. These scores are mapped onto the whole-dataset network to determine which clusters of related metabolites are produced by each FAC. Network analysis provides for identification of highly unique and abundant metabolites produced by various BGCs analyzed (FIG. 20). A major value of the MS2-based scoring system is that is provides analysis of very large datasets, enabling high-throughput natural product discovery; provides higher confidence in "hit" metabolites because multiple highly-scoring related metabolites are identified, rather than just one, and because these metabolites are unique across a much larger dataset; and provides structural insights about each metabolite present in MS2 fragmentation data.

Example 3

Analysis of FACs from Additional Species and Genera

Experiments were conducted during development of embodiments herein 58 FACs from comprising pBGCs from *Talaromyces marneffei, Fusarium solani, Pseudogymnoascus destructans*, and *Penicillium expansum* using the LC-MS screening, FAC-score analysis, and deletion validation. Metabolites were identified and pBGCs confirmed as being BGCs from from *F. solani* (Fs), *P. expansum* (Pe), and T *marneffei* (Tm) (Table 5). This analysis yielded an approximately 9% hit rate.

TABLE 5

Metabolite identification from non-*Aspergillus* fungal species

| FAC Strain | Validated Hit? | m/z | Formula |
|---|---|---|---|
| Fs10 | Yes | 728.348 | Unknown |
| Pe21 | Yes | 291.062 | $C_{13}H_{11}N_2O_6$ |
| Pe22 | Yes | 381.166 | $C_{18}H_{25}O_7N_2$ |
| Tm10 | Yes | 306.117 | $C_{12}H_{20}O_8N$ |
| Tm2 | Yes | 485.219 | $C_{27}H_{33}O_8$ |

The invention claimed is:

1. A method of screening for metabolites comprising:
   (a) expressing a test putative biosynthetic gene cluster (pBGC) in a host system;
   (b) untargeted screening of metabolites produced by the host system by one or more bioanalytical techniques to identify metabolite features produced by the test pBGC;
   (c) scoring a metabolite feature based on a combination of uniqueness and abundance, wherein a score is calculated by:
      (i) comparing the abundance of the metabolite feature in a test sample from the host system expressing the test pBGC to the abundance of the metabolite feature in multiple samples from the host system lacking the test pBGC to determine the uniqueness of the metabolite feature among samples, and
      (ii) combining the uniqueness of the metabolite feature with the relative abundance of the metabolite feature in the test sample to generate a compound score; and
   (d) identifying:
      (i) the test pBGC as a biosynthetic gene cluster (BGC), and/or
      (ii) a particular metabolite as being produced by the test pBGC, if the compound score identifies the metabolite feature as being unique and abundant relative to other scored metabolite features
   (e) validating the identification made in step (d) by repeating steps (a) and (b) with a validation pBGC comprising a deletion within the test pBGC, wherein the validation confirms that the test pBGC is a BGC that produces the metabolite if the deletion reduces or eliminates production of the metabolite by the host system.

2. The method of claim 1, wherein the test pBGC comprises a sequence derived from genomic DNA of a fungus of interest.

3. The method of claim 2, wherein the test pBGC has been inserted into a fungal artificial chromosome (FAC).

4. The method of claim 1, wherein the host system is a fungal cell.

5. The method of claim 4, wherein the fungal cell is selected from the group consisting of *Ashbya gossypii, Aspergillus nidulans, Coprinus cinereus, Cryptococcus neoformans, Neurospora crassa, Saccharomyces cerevisiae, Schizophyllum commune, Schizosaccharomyces pombe*, and *Ustilago maydis*.

6. The method of claim 1, wherein the host system is a fungal cell lysate.

7. The method of claim 1, wherein the host system is an in vitro expression system.

8. The method of claim 1, wherein screening comprises subjecting the host system or test sample derived therefrom to the one or more bioanalytical techniques to identify bioanalytical features that correlate to metabolites produced by the host system expressing the test pBGC.

9. The method of claim 8, wherein scoring comprises calculating a numerical score or otherwise ranking the features obtained in the screening based on a combination of uniqueness and abundance.

10. The method of claim 9, wherein abundance is a measure of the size of a feature and/or amount of a metabolite, relative to other features and/or metabolites produced by the host system expressing the test pBGC.

11. The method of claim 10, wherein uniqueness is a measure of the relative rarity of a feature and/or metabolite, relative to other features and/or metabolites produced by similar host systems expressing other BGCs or pBGCs.

12. The method of claim 1, wherein the one or more bioanalytical techniques are selected from the group consisting of mass spectrometry (MS), tandem mass spectrometry (MS2), high performance liquid chromatography (HPLC), gas chromatography, ultra performance liquid chromatography (UPLC), supercritical fluid chromatography, nuclear magnetic resonance (NMR), liquid chromatography-mass spectrometry (LC-MS), gas chromatography-mass spectrometry (GC-MS), liquid chromatography-diode array detection (LC-DAD), capillary electrophoresis-mass spectrometry (CE-MS), and liquid chromatography-tandem mass spectrometry (LC-MS2).

13. The method of claim 1, further comprising isolating the particular metabolite.

14. The method of claim 1, further comprising identifying the particular metabolite.

15. The method of claim 1, wherein comparing the abundance of the metabolite feature in a test sample to abundance of the metabolite feature in one or more control samples comprises dividing the abundance of the metabolite feature in the test sample by the average abundance of the metabolite feature in the one or more control samples.

16. The method of claim 15, wherein combining the uniqueness of the metabolite feature with the relative abundance of the metabolite feature comprises multiplying the uniqueness of the metabolite feature among samples tested by the abundance of the metabolite feature in the test sample.

17. The method of claim 1, wherein samples comprising the host system lacking the test pBGC include host systems lacking a pBGC and/or host systems expressing other pBGCs.

* * * * *

UNITED STATES PATENT AND TRADEMARK OFFICE
CERTIFICATE OF CORRECTION

| | |
|---|---|
| PATENT NO. | : 10,808,256 B2 |
| APPLICATION NO. | : 15/602917 |
| DATED | : October 20, 2020 |
| INVENTOR(S) | : Neil L. Kelleher et al. |

It is certified that error appears in the above-identified patent and that said Letters Patent is hereby corrected as shown below:

In the Specification

In Column 1, Line 14, please correct the government funding statement to read:
-- This invention was made with government support under grant number R44 AI094885 awarded by the National Institutes of Health. The government has certain rights in the invention. --

Signed and Sealed this
Twenty-eighth Day of November, 2023

Katherine Kelly Vidal
*Director of the United States Patent and Trademark Office*